(12) United States Patent
Kley et al.

(10) Patent No.: US 9,073,954 B2
(45) Date of Patent: Jul. 7, 2015

(54) 5-SUBSTITUTED BENZIMIDAZOLIUM COMPOUNDS

(71) Applicants: Joerg Kley, Mittelbiberach (DE); Sara Frattini, Castelleone (IT); Dieter Hamprecht, Pozzolengo (IT); Armin Heckel, Biberach an der Riss (DE)

(72) Inventors: Joerg Kley, Mittelbiberach (DE); Sara Frattini, Castelleone (IT); Dieter Hamprecht, Pozzolengo (IT); Armin Heckel, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/330,017

(22) Filed: Jul. 14, 2014

(65) Prior Publication Data
US 2015/0018313 A1 Jan. 15, 2015

(30) Foreign Application Priority Data
Jul. 15, 2013 (EP) .................... 13176490

(51) Int. Cl.
*C07D 403/12* (2006.01)
*C07D 403/14* (2006.01)
*C07D 493/04* (2006.01)
*C07F 9/6509* (2006.01)
*A61K 31/675* (2006.01)
*A61K 45/06* (2006.01)
*A61K 31/497* (2006.01)
*A61K 31/683* (2006.01)
*A61K 31/5377* (2006.01)

(52) U.S. Cl.
CPC ......... *C07F 9/650964* (2013.01); *A61K 31/675* (2013.01); *A61K 45/06* (2013.01); *C07D 403/12* (2013.01); *A61K 31/497* (2013.01); *C07D 493/04* (2013.01); *A61K 31/683* (2013.01); *C07D 403/14* (2013.01); *A61K 31/5377* (2013.01)

(58) Field of Classification Search
CPC ... C07D 403/12; C07D 403/14; C07D 493/04
USPC .......................................................... 544/405
See application file for complete search history.

(56) References Cited

U.S. PATENT DOCUMENTS

2015/0018314 A1 1/2015 Kley
2015/0018315 A1 1/2015 Kley et al.

FOREIGN PATENT DOCUMENTS

WO 2011079087 A1 6/2011

OTHER PUBLICATIONS

U.S. Appl. No. 14/589,013, filed Jan. 5, 2015, Inventor Armin Heckel.

*Primary Examiner* — Brian McDowell
(74) *Attorney, Agent, or Firm* — Michael P. Morris; Edward S. Lazer

(57) ABSTRACT

The present invention relates to compounds of general formula (I)

(I)

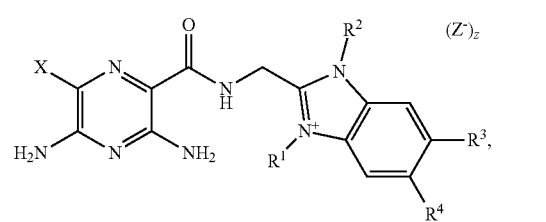

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

11 Claims, No Drawings

5-SUBSTITUTED BENZIMIDAZOLIUM COMPOUNDS

1. FIELD OF THE INVENTION

The present invention relates to compounds of general formula (I)

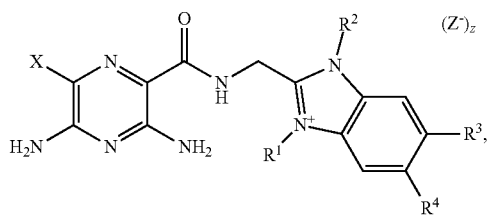

and the tautomers and the salts thereof, particularly the pharmaceutically acceptable salts thereof with inorganic or organic acids including zwitterions, which have valuable pharmacological properties, particularly an inhibitory effect on epithelial sodium channels, the use thereof for the treatment of diseases, particularly diseases of the lungs and airways.

2. BACKGROUND TO THE INVENTION

WO2011079087 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways. The new compounds of the present invention exhibit a reduced permeability being beneficial for topical lung treatment.

3. DETAILED DESCRIPTION OF THE INVENTION

It has surprisingly been found that the problem mentioned above is solved by compounds of formula (I) of the present invention.

The present invention therefore relates to a compound of formula (I)

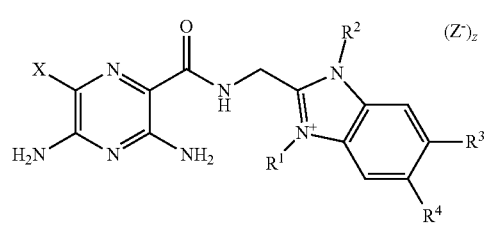

characterized in that
X denotes Cl or Br,
$R^1$ and $R^2$ denote independently $C_{1-4}$-alkyl-, $CH_3$—O—$C_{2-4}$-alkylene-, HO—$(CH_2)_n$—O—$C_{2-3}$-alkylene- or HO—$C_{2-6}$-alkylene-,
$R^3$ denotes HO—, (HO—$C_{2-3}$-alkylene)$_2$N—, ($R^5$O—) ($R^6$O—)P(O)—$(CH_2)_n$—O—, (HO—)(($CH_3$)$_3$N$^+$—$(CH_2)_n$—)P(O)—O—$(CH_2)_n$—O—, ($R^5$O—)($C_{1-3}$-alkyl-)P(O)—O—$(CH_2)_n$—O—, $R^7R^8$N—C(O)—$C_{1-2}$-alkylene-O—, $R^9R^{10}$N—$(CH_2)_n$—O—, ($CH_3$)$_3$N$^+$—$(CH_2)_n$—O—, $R^9R^{11}$N—$(CH_2)_n$—O—, $CH_3$—(O—$CH_2$—$CH_2$)$_m$—O—, H—(O—$CH_2$—$CH_2$)$_n$—O—, morpholino-C(O)—, $R^9R^{10}$N—$CH_2$—, ($CH_3$)$_3$N$^+$—$CH_2$—, 9-fluorenylmethyl-O—C(O)—NR$^9$—$CH_2$—, $R^9R^{10}$N—$CH_2$—C(O)—NR$^9$—$CH_2$—, ($CH_3$)$_3$N$^+$—$CH_2$—C(O)—NR$^9$—$CH_2$—, $R^9$—O—C(O)—$CH_2$—NR$^9$—$CH_2$—, ($R^9R^{10}$N-cyclohexyl-NR$^9$—C(O)-)$_2$phenyl-O—$CH_2$—C(O)—NR$^9$—$CH_2$—, tetrahydropyranyl-O— or
$R^3$ denotes a substituent selected from the group consisting of formula (cae)

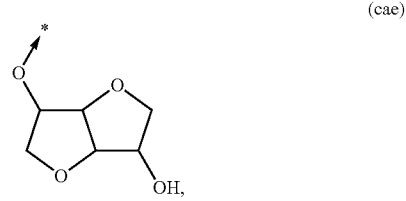

$R^4$ denotes H, halogen or ($C_{1-4}$-alkyl-)NH—C(O)—,
$R^5$ denotes H or $C_{1-3}$-alkyl-,
$R^6$ denotes H, $C_{1-3}$-alkyl-, $CH_3$—O—$(CH_2)_n$—, tetrahydrofuryl-$CH_2$— or ($CH_3$)$_3$N$^+$—$(CH_2)_n$—,
$R^7$ and $R^8$ denote independently H, $C_{1-4}$-alkyl-, ($CH_3$)$_2$P(O)—$CH_2$—O—$(CH_2)_n$— or,
$R^7$ and $R^8$ together with the nitrogen atom they are attached to form a 5- or 6-membered heterocycle from the group consisting of pyrrolidine, morpholine, piperazine, piperazinone, N-methylpiperazine, N-methylpiperazinone, N—BOC-piperazine, thiomorpholine, thiomorpholine-S-oxide or thiomorpholine sulfone,
$R^9$ and $R^{10}$ denote independently H or methyl,
$R^{11}$ denotes $C_{1-4}$-alkyl-O—C(O)—, $NH_2$—C(NH)—, $R^9R^{10}$N—$CH_2$—C(O)—, ($CH_3$)$_3$N$^+$—$CH_2$—C(O)— or $R^9$—O—C(O)—$CH_2$—,
m denotes 1, 2 or 3,
n denotes 2 or 3,
$Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate or p-toluenesulfonate,
z denotes 0 for negatively charged substituents $R^1$-$R^4$, 1 for uncharged substituents $R^1$-$R^4$ or 2 for positively charged substituents $R^1$-$R^4$,
and tautomers and optionally the pharmacologically acceptable acid addition salts thereof.

The present invention further relates to a compound of formula (I),

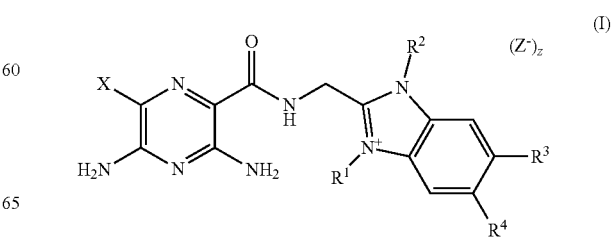

wherein

X denotes Cl or Br, $R^1$, $R^2$ denote independently $C_{1-4}$-alkyl-, $CH_3$—O—$C_{2-4}$-alkylene-, HO—$(CH_2)_n$—O—$C_{2-3}$-alkylene- or HO—$C_{2-6}$-alkylene-, $R^3$ denotes HO—, (HO—$C_{2-3}$-alkylene)$_2$N—, ($R^5$O—)($R^6$O—)P(O)—$(CH_2)_n$—O—, (HO—)(($CH_3$)$_3$N$^+$—$(CH_2)_n$—)P(O)—O—$(CH_2)_n$—O—, ($R^5$O—)($C_{1-3}$-alkyl-)P(O)—O—$(CH_2)_n$—O—, $R^7R^8$N—C(O)—$C_{1-2}$-alkylene-O—, $R^9R^{10}$N—$(CH_2)_n$—O—, $(CH_3)_3$N$^+$—$(CH_2)_n$—O—, $R^9R^{11}$N—$(CH_2)_n$—O—, $CH_3$—(O—$CH_2$—$CH_2)_m$—O—, H—(O—$CH_2$—$CH_2)_m$—O—, morpholino-C(O)—, $R^9R^{10}$N—$CH_2$—, $(CH_3)_3$N$^+$—$CH_2$—, 9-fluorenylmethyl-O—C(O)—NR$^9$—$CH_2$—, $R^9R^{10}$N—$CH_2$—C(O)—NR$^9$—$CH_2$—, $(CH_3)_3$N$^+$—$CH_2$—C(O)—NR$^9$—$CH_2$—, $R^9$—O—C(O)—$CH_2$—NR$^9$—$CH_2$—, ($R^9R^{10}$N-cyclohexyl-NR$^9$—C(O)-)$_2$phenyl-O—$CH_2$—C(O)—NR$^9$—$CH_2$—, tetrahydropyranyl-O— or $R^3$ denotes a substituent selected from the group consisting of formula (cae)

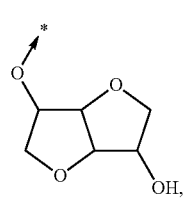

(cae)

$R^4$ denotes H, halogen, or ($C_{1-4}$-alkyl-)NH—C(O)—, $R^5$ denotes H or $C_{1-3}$-alkyl-, $R^6$ denotes H, $CH_3$—O—$(CH_2)_n$—, tetrahydrofuryl-$CH_2$— or $(CH_3)_3$N$^+$—$(CH_2)_n$—, $R^7$ and $R^8$ denote independently H, $C_{1-4}$-alkyl-, $(CH_3)_2$P(O)—$CH_2$—O—$(CH_2)_n$— or, $R^7$ and $R^8$ together with the nitrogen atom they are attached to form a 5- or 6-membered heterocycle from the group consisting of pyrrolidine, morpholine, piperazine, piperazinone, N-methylpiperazine, N-methylpiperazinone, thiomorpholine, thiomorpholine-S-oxide or thiomorpholine sulfone, $R^9$ and $R^{10}$ denote independently H or methyl, $R^{11}$ denotes $C_{1-4}$-alkyl-O—C(O)—, $NH_2$—C(NH)—, $R^9R^{10}$N—$CH_2$—C(O)—, $(CH_3)_3$N$^+$—$CH_2$—C(O)— or $R^9$—O—C(O)—$CH_2$—, m denotes 1, 2 or 3, n denotes 2 or 3, Z$^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate or p-toluenesulfonate, z denotes 0 for negatively charged substituents $R^1$-$R^4$, 1 for uncharged substituents $R^1$-$R^4$ or 2 for positively charged substituents $R^1$-$R^4$, and tautomers and optionally the pharmacologically acceptable acid addition salts thereof.

Preferred compounds of formula (I) are those wherein $R^1$ and $R^2$ denote independently $C_{1-3}$-alkyl-, —$CH_3$—O—$C_{2-3}$-alkylene- or HO—$C_{2-6}$-alkylene-.

Particularly preferred are compounds of formula (I) wherein $R^1$ denotes $C_{1-3}$-alkyl- or $CH_3$—O—$C_{2-3}$-alkylene-.

Also particularly preferred are compounds of formula (I) wherein $R^2$ denotes $C_{1-3}$-alkyl- or HO—$C_{2-6}$-alkylene-.

Also particularly preferred are compounds of formula (I) wherein $R^3$ denotes HO—, (HO—$C_{2-3}$-alkylene)$_2$N—, ($R^5$O—)($R^6$O—)P(O)—$(CH_2)_n$—O—, (HO—)(($CH_3$)$_3$N$^+$—$(CH_2)_3$—)P(O)—O—$(CH_2)_n$—O—, $R^7R^8$N—C(O)—$C_{1-2}$-alkylene-O—, $R^9R^{10}$N—$(CH_2)_n$—O—, $(CH_3)_3$N$^+$—$(CH_2)_2$—O—, $R^9R^{11}$N—$(CH_2)_n$—O—, $CH_3$—(O—$CH_2$—$CH_2)_n$—O—, morpholino-C(O)—, $R^3R^{10}$N—$CH_2$—, $(CH_3)_3$N$^+$—$CH_2$—, 9-fluorenylmethyl-O—C(O)—NH—$CH_2$—, $R^9R^{10}$N—$CH_2$—C(O)—NH—$CH_2$—, $(CH_3)_3$N$^+$—$CH_2$—C(O)—NH—$CH_2$—, $R^9$—O—C(O)—$CH_2$—NH—$CH_2$— or $R^3$ denotes a substituent selected from the group consisting of formula (cae)-(caf)

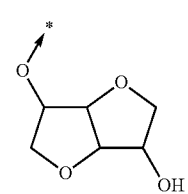

(cae)

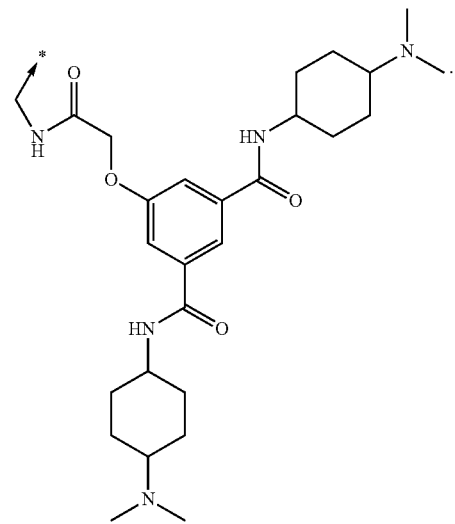

(caf)

$R^5$ denotes H or $C_{1-3}$-alkyl- $R^6$ denotes H, $C_{1-3}$-alkyl- or $(CH_3)_3$N$^+$—$(CH_2)_n$—, $R^7$ and $R^8$ denote independently H, $C_{1-4}$-alkyl- or $R^7$ and $R^8$ together with the nitrogen atom they are attached to form a piperazinone, $R^9$ and $R^{10}$ denote independently H or methyl, $R^{11}$ denotes $C_{1-4}$-alkyl-O—C(O)—, $NH_2$—C(NH)—, $R^9R^{10}$N—$CH_2$—C(O)—, $(CH_3)_3$N$^+$—$CH_2$—C(O)— or $R^9$—O—C(O)—$CH_2$—, m denotes 1, 2 or 3, n denotes 2 or 3.

Also particularly preferred are compounds of formula (I) wherein $R^1$ denotes methyl-, ethyl- or a substituent of formula (aa)

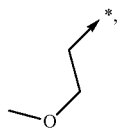
(aa)

$R^2$ denotes ethyl-, 2-propyl- or a substituent of formula (ba)

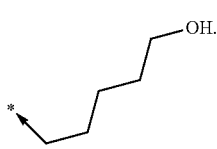
(ba)

Also particularly preferred are compounds of formula (I) wherein $R^3$ denotes HO— or $R^3$ denotes a substituent selected from the group consisting of formula (ca)-(cad)

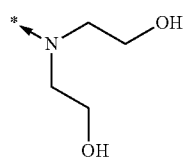
(ca)

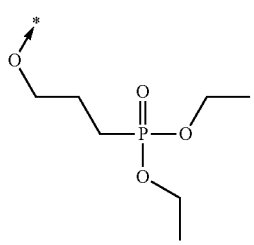
(cb)

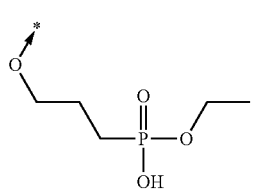
(cc)

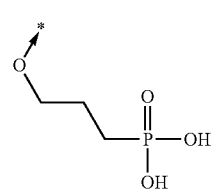
(cd)

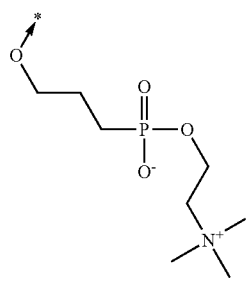
(ce)

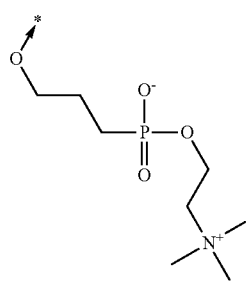
(cf)

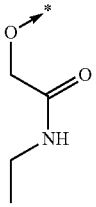
(cg)

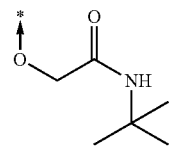
(ch)

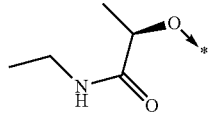
(ci)

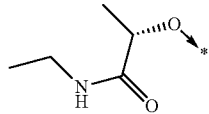
(cj)

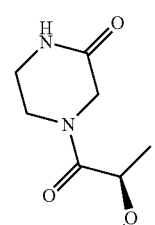
(ck)

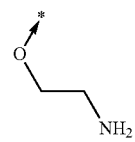
(cl)

| | | |
|---|---|---|
| (cm) | 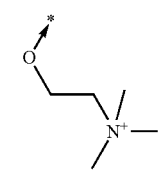 | |
| (cn) | 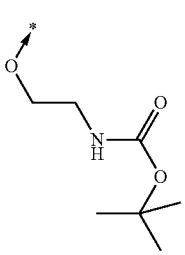 | |
| (co) | 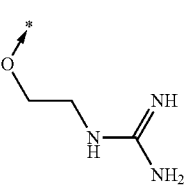 | |
| (cp) | 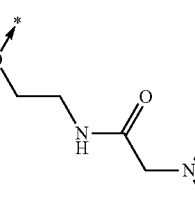 | |
| (cq) | 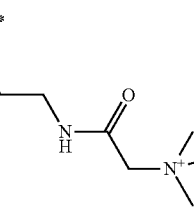 | |
| (cr) | 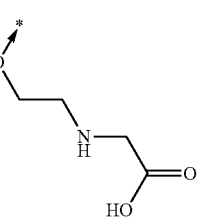 | |
| (cs) | 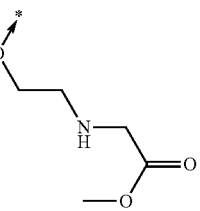 | |
| | | |
|---|---|---|
| (ct) | 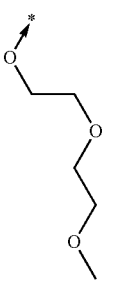 | |
| (cu) | 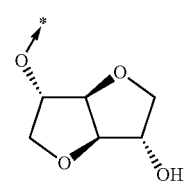 | |
| (cv) | 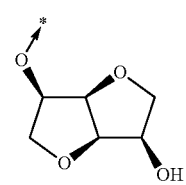 | |
| (cw) | 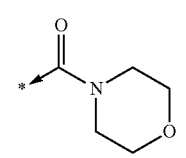 | |
| (cx) | 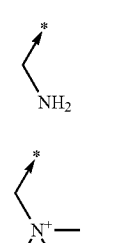 | |
| (cy) | 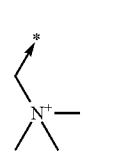 | |
| (cz) | 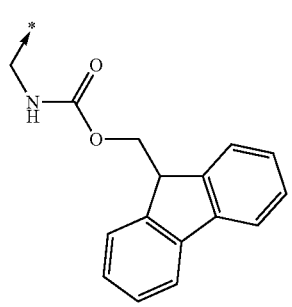 | |
| (caa) | 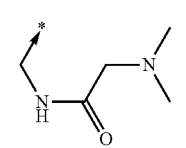 | |

-continued

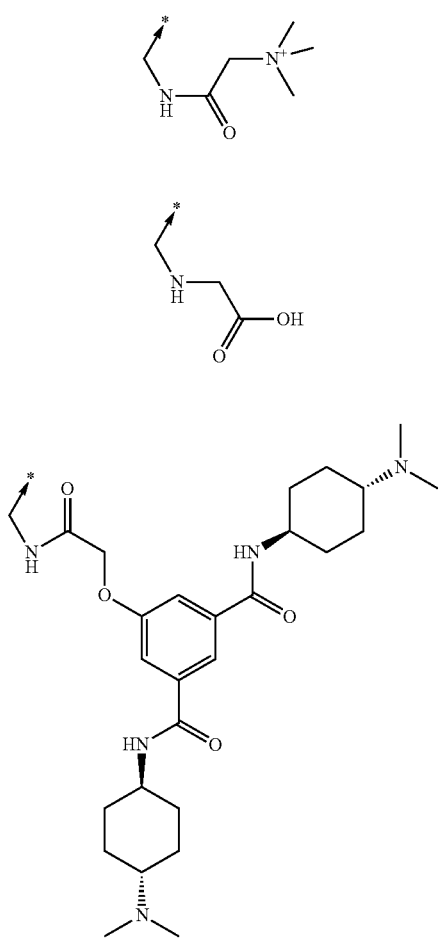

Also particularly preferred are compounds of formula (I) wherein
R⁴ denotes H, F or Cl.
especially preferred are compounds of formula (I)

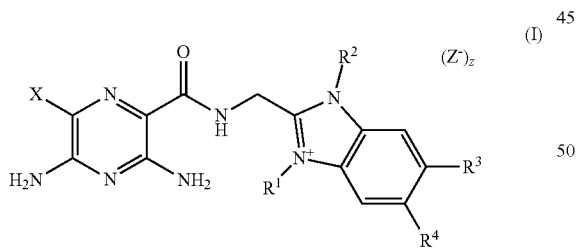

wherein
X denotes Cl or Br,
R¹ denotes methyl-, ethyl- or a substituent of formula (aa)

R² denotes ethyl-, 2-propyl- or a substituent of formula (ba)

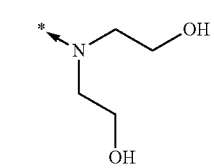

R³ denotes HO— or
R³ denotes a substituent selected from the group consisting of formula (ca)-(cad)

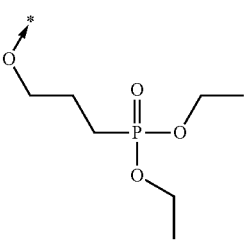

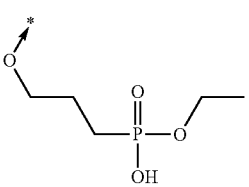

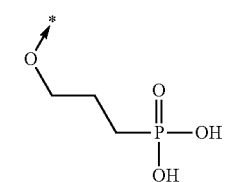

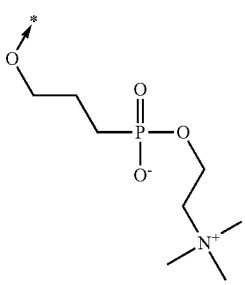

-continued
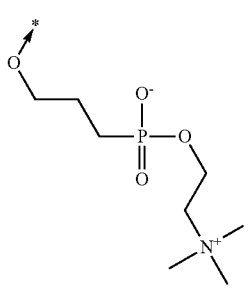
(cf)
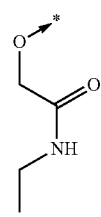
(cg)
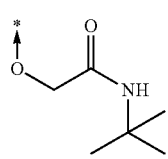
(ch)
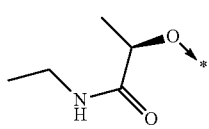
(ci)
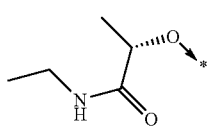
(cj)
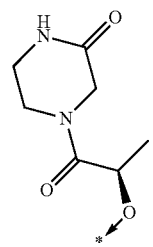
(ck)
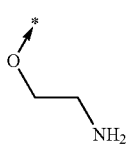
(cl)
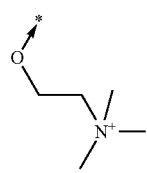
(cm)
-continued
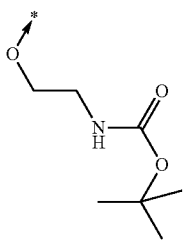
(cn)
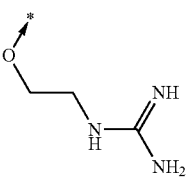
(co)
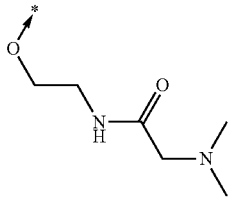
(cp)
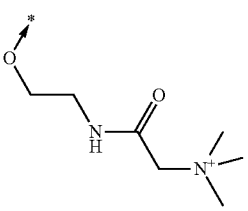
(cq)
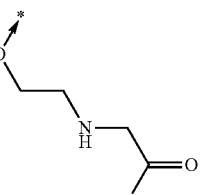
(cr)
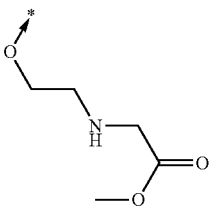
(cs)
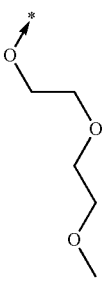
(ct)

-continued (cu)

(cv)

(cw)

(cx)

(cy)

(cz)

(caa)

(cab)

(cac)

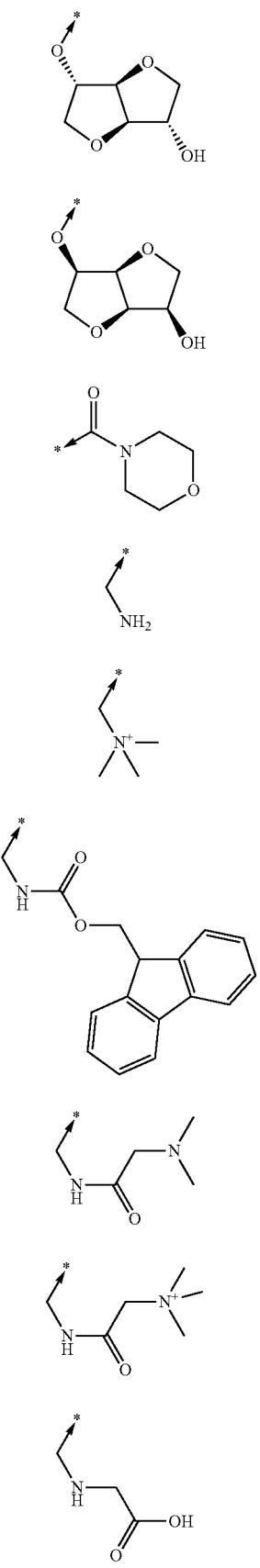

-continued (cad)

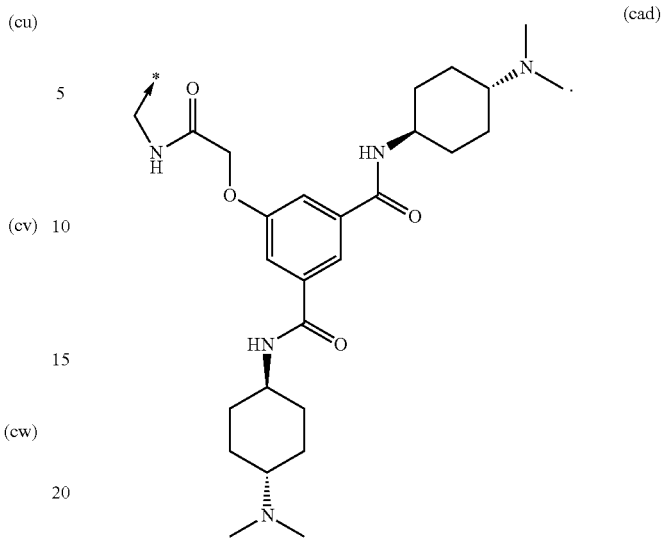

$R^4$ denotes H, F or Cl,
$Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate or p-toluenesulfonate,
z denotes 0 for negatively charged substituents $R^1$-$R^4$, 1 for uncharged substituents $R^1$-$R^4$ or 2 for positively charged substituents $R^1$-$R^4$,
and tautomers and optionally the pharmacologically acceptable acid addition salts thereof.

A further embodiment of the current invention is compounds of formula (I), or a pharmaceutically acceptable salt thereof for use as a medicament.

A further embodiment of the current invention is compounds of formula (I), or a pharmaceutically acceptable salt thereof for use in the treatment of a disease selected from among respiratory diseases or complaints and allergic diseases of the airways.

Preferred are compounds of formula (I) or a pharmaceutically acceptable salt thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins, preferably chronic bronchitis, acute bronchitis, bronchitis, chronic obstructive bronchitis (COPD), asthma (intrinsic or allergic), cystic fibrosis and pediatric asthma, preferably chronic bronchitis, COPD and cystic fibrosis.

A further embodiment of the current invention is a pharmaceutical composition comprising at least one compound according to the invention or a pharmaceutically acceptable salt thereof and a pharmaceutically acceptable carrier.

A further embodiment of the current invention are medicament combinations which contain, besides one or more compounds of a compound according to the invention, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof, preferably VX-770 and VX-809, or double or triple combinations thereof.

4. TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal bond indicates the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

If a compound of the present invention is depicted in the form of a chemical name and as a formula, in case of any discrepancy the formula shall prevail. An asterisk is may be used in sub-formulas to indicate the bond which is connected to the core molecule as defined.

For example, the term "3-carboxypropyl-group" represents the following substituent:

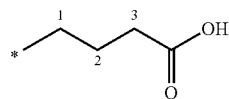

wherein the carboxy group is attached to the third carbon atom of the propyl group.

The terms "1-methylpropyl-", "2,2-dimethylpropyl-" or "cyclopropylmethyl-" group represent the following groups:

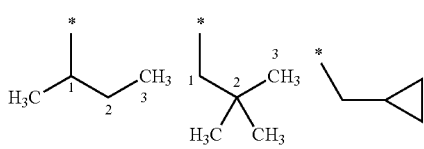

The asterisk may be used in sub-formulas to indicate the bond which is connected to the core molecule as defined.

Likewise an arrow together with an asterisk may be used in sub-formulas to indicate the bond which is connected to the core molecule as defined.

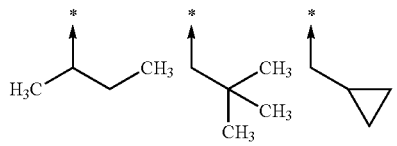

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Pro-drugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

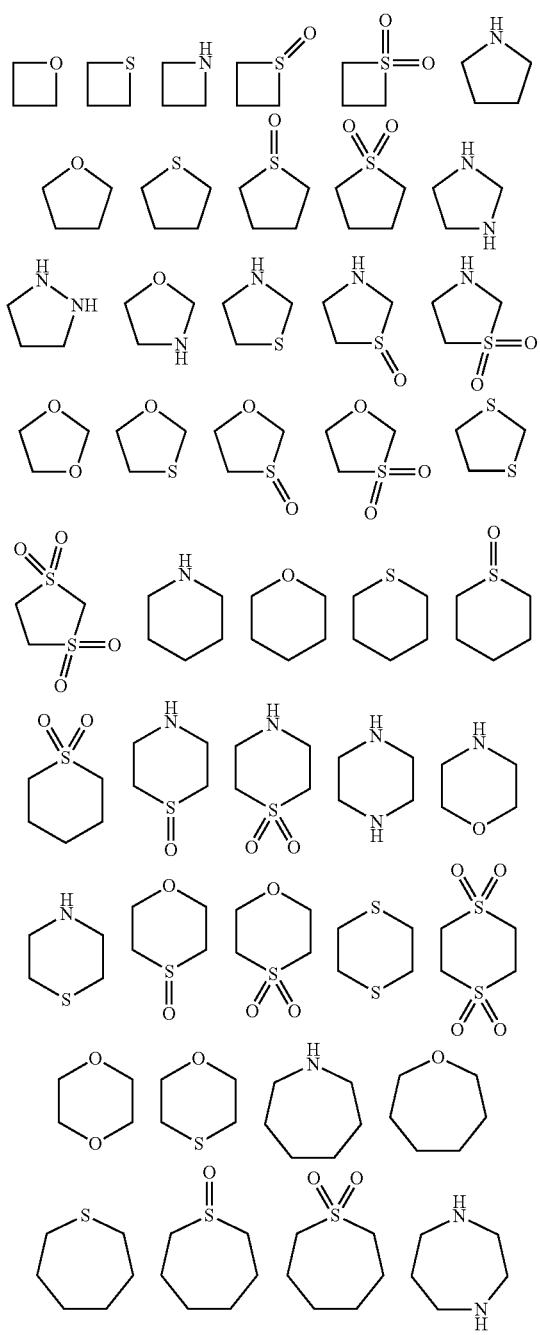
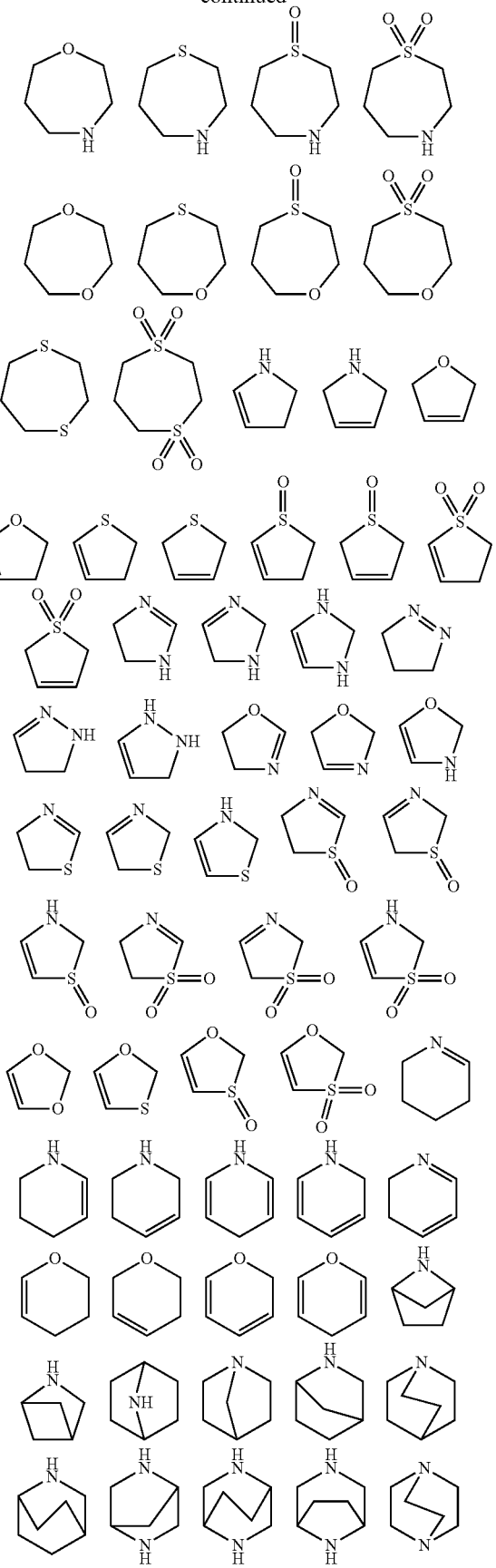

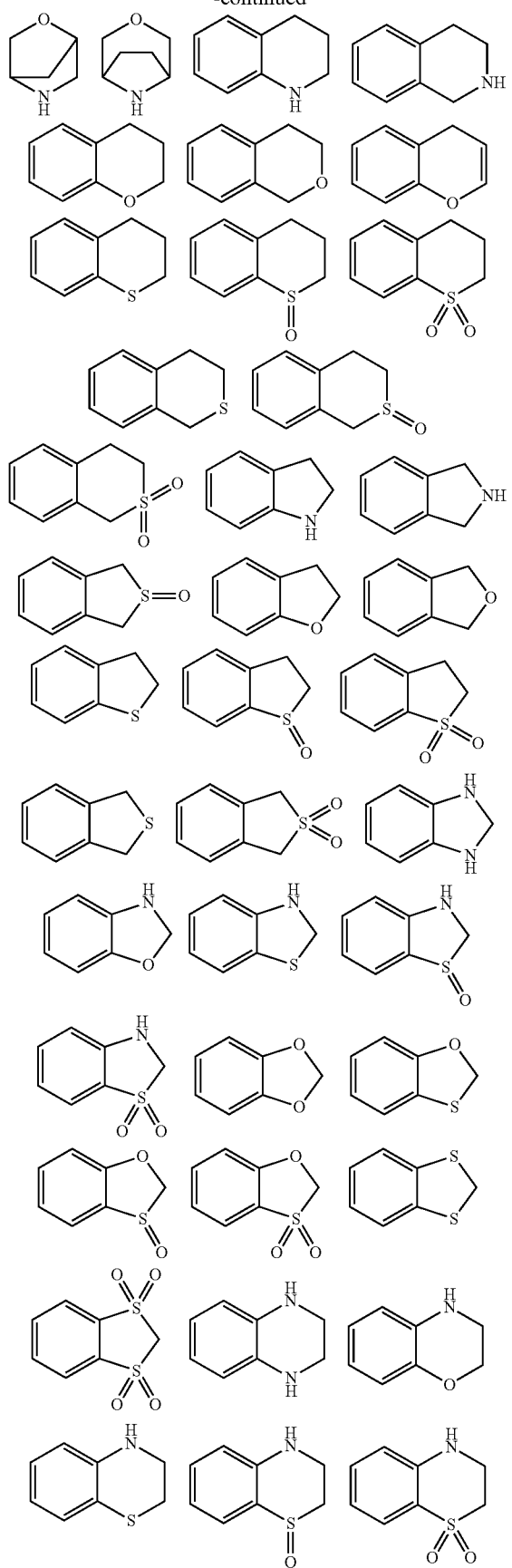

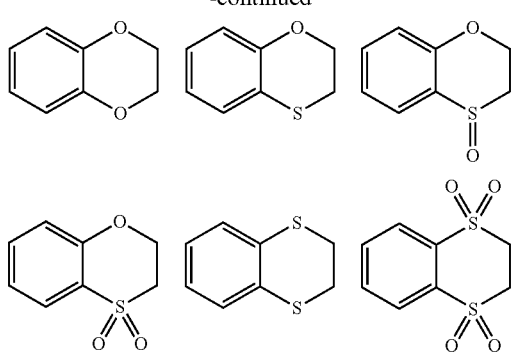

The term heteroaromatic means heteroaryl, monocyclic $C_{5-14}$-heteroaryl, or polycyclic $C_{5-14}$-heteroaryl.

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

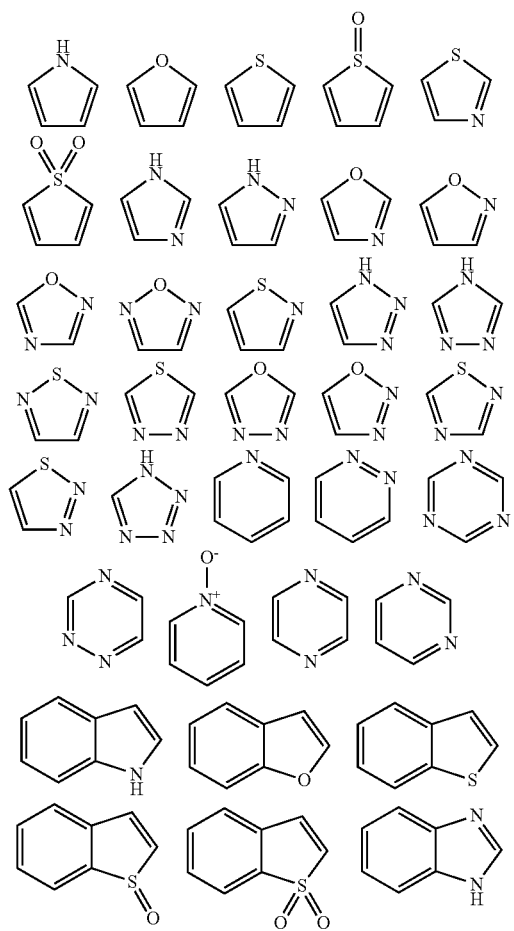

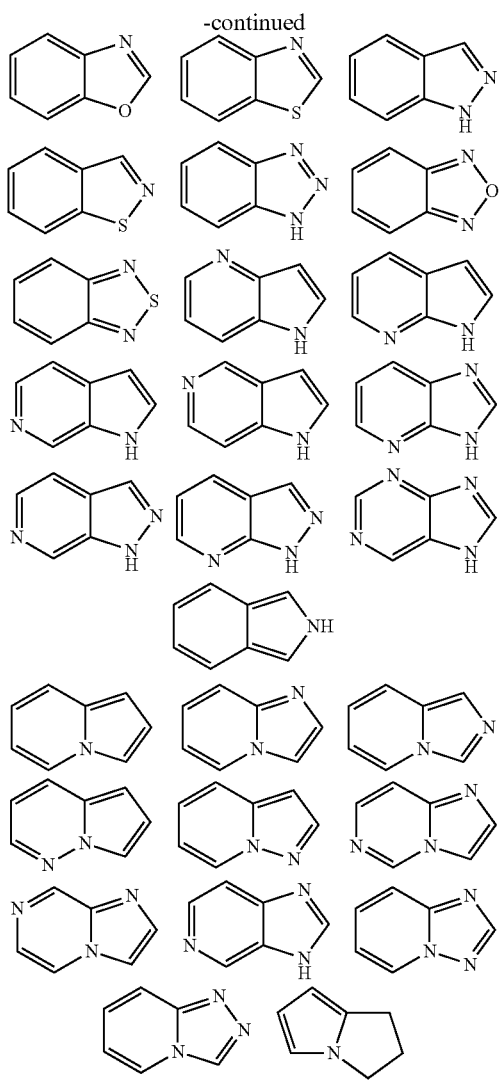

The term "monocyclic C$_{5-7}$-heterocyclyl" means a saturated or unsaturated non-aromatic monocyclic-ring systems containing one or more heteroatoms selected from N, O or S(O)$_r$, wherein r=0, 1 or 2, consisting of 5 to 7 ring atoms. The term "monocyclic C$_{5-7}$-heterocyclyl" is intended to include all the possible isomeric forms.

Thus, the term "monocyclic C$_{5-7}$-heterocyclyl" includes the following exemplary structures which are not depicted as radicals as each form may be attached through a covalent bond to any atom so long as appropriate valences are maintained:

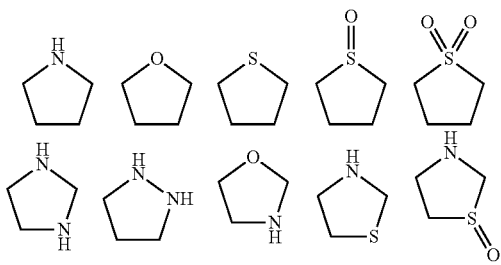

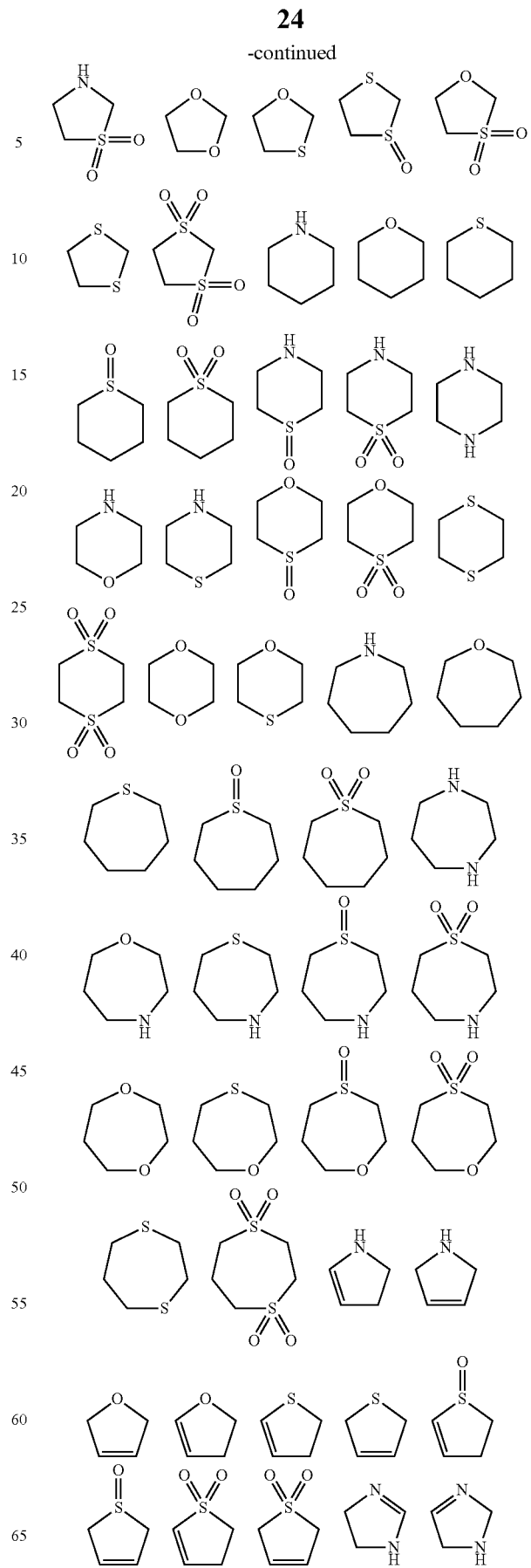

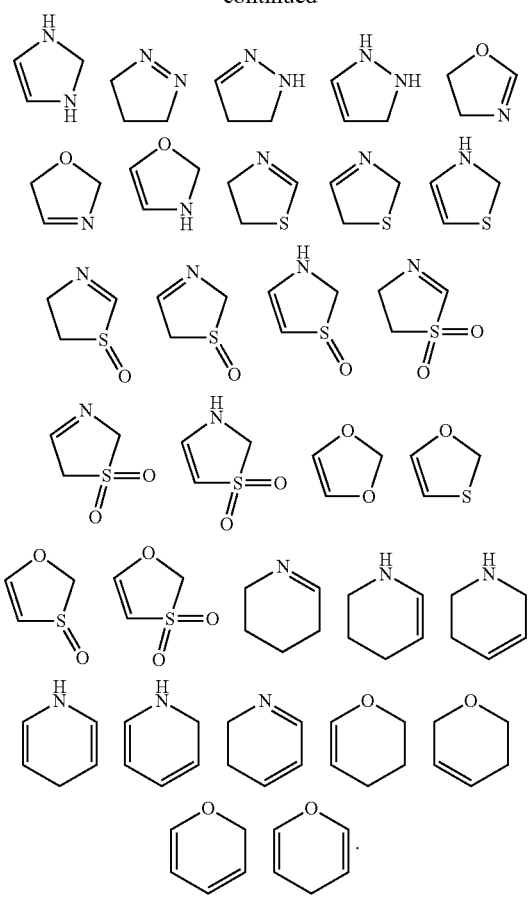

The term "monocyclic C$_{5-6}$-heteroaryl" means a monocyclic-ring systems containing one or more heteroatoms selected from N, O or S(O)$_r$, wherein r=0, 1 or 2, consisting of 5 or 6 ring atoms wherein at least one of the heteroatoms is part of aromatic ring. The term "monocyclic C$_{5-6}$-heteroaryl" is intended to include all the possible isomeric forms.

Thus, the term "monocyclic C$_{5-6}$-heteroaryl" includes the following exemplary structures which are not depicted as radicals as each form may be attached through a covalent bond to any atom so long as appropriate valences are maintained:

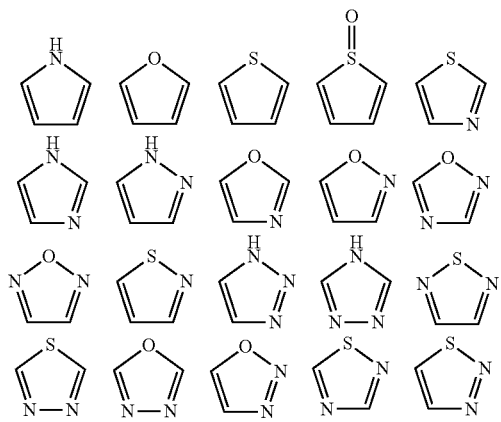

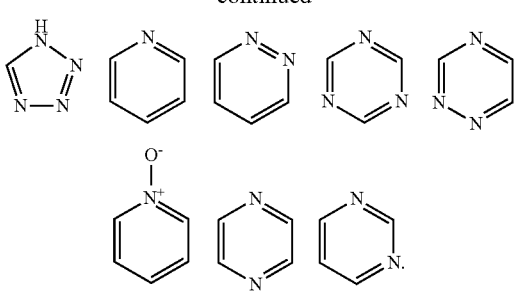

The term "bicyclic C$_{8-10}$-heterocyclyl" means a saturated or unsaturated bicyclic-ring systems including aromatic ring systems containing one or more heteroatoms selected from N, O or S(O)$_r$, wherein r=0, 1 or 2, consisting of 8 to 10 ring atoms wherein the heteroatoms is optionally part of the aromatic ring. The term "bicyclic C$_{8-10}$-heterocyclyl" is intended to include all the possible isomeric forms.

Thus, the term "bicyclic C$_{8-10}$-heterocyclyl" includes the following exemplary structures which are not depicted as radicals as each form may be attached through a covalent bond to any atom so long as appropriate valences are maintained:

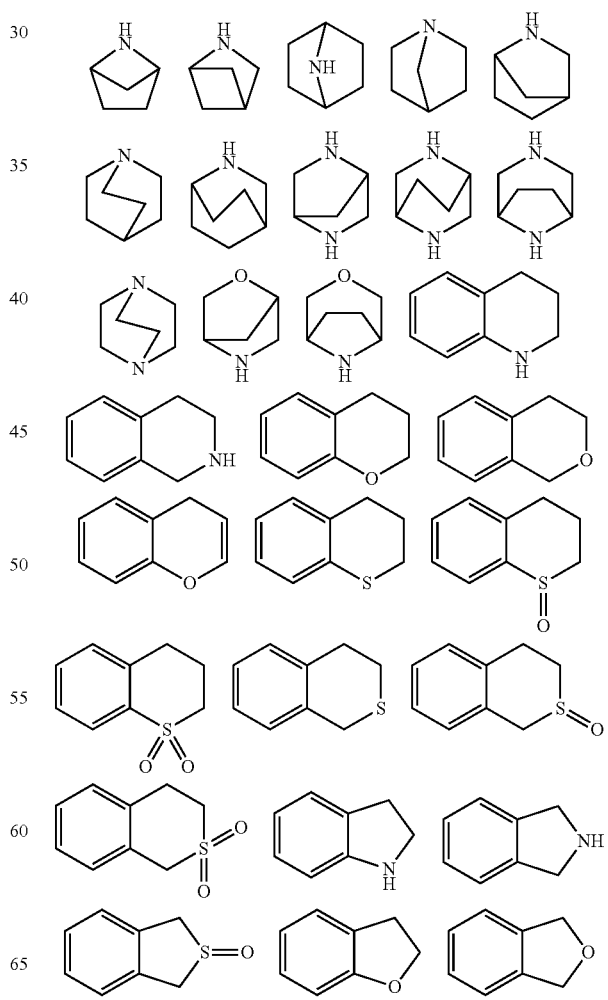

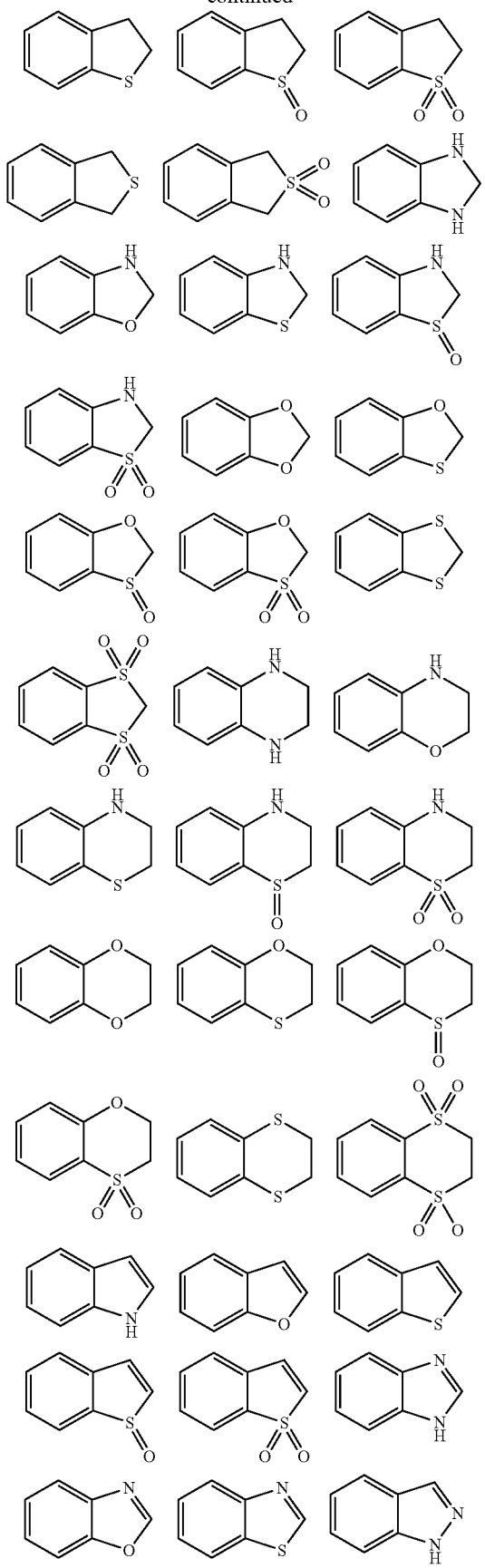
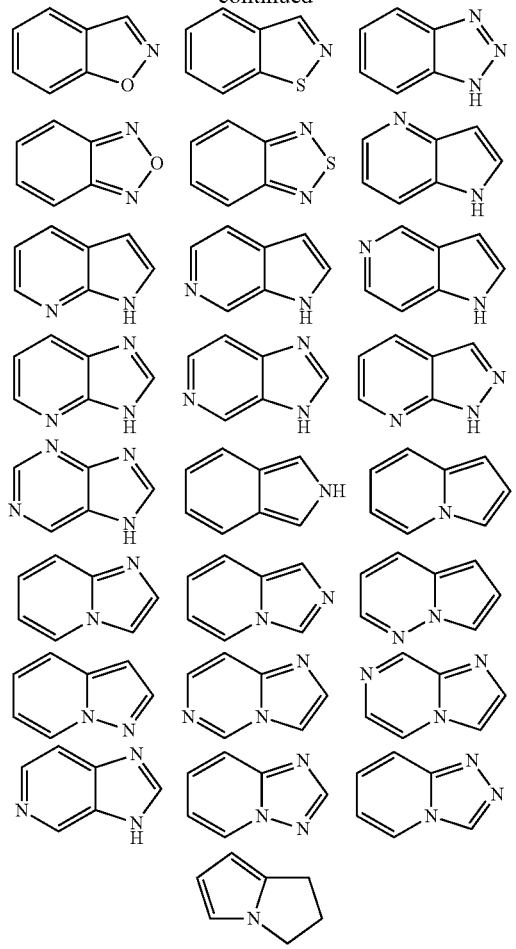

The term "annelated species of aryl or heterocyclyl" as used herein, either alone or in combination with another substituent wherein the annelated species presents as an aryl-het (a), a hetaryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1\text{-}n}$-alkyl", wherein n is an integer from 2 to n, either alone or in combination with another radical denotes an acyclic, saturated, branched or linear hydrocarbon radical with 1 to n C atoms. For example the term $C_{1\text{-}5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1\text{-}n}$-alkylene" wherein n is an integer 2 to n, either alone or in combination with another radical, denotes an acyclic, straight or branched chain divalent alkyl radical containing from 1 to n carbon atoms. For example the term $C_{1\text{-}4}$-alkylene includes $-CH_2-$, $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

The term "$C_{2\text{-}n}$-alkenyl", is used for a group as defined in the definition for "$C_{1\text{-}n}$-alkyl" with at least two carbon atoms, if at least two of those carbon atoms of said group are bonded to each other by a double bond.

The term "$C_{2\text{-}n}$-alkenylene" is used for a group as defined in the definition for "$C_{1\text{-}n}$-alkylene" with at least two carbon atoms, if at least two of those carbon atoms of said group are bonded to each other by a double bond.

The term "$C_{2\text{-}n}$-alkynyl", is used for a group as defined in the definition for "$C_{1\text{-}n}$-alkyl" with at least two carbon atoms, if at least two of those carbon atoms of said group are bonded to each other by a triple bond.

The term "$C_{2\text{-}n}$-alkynylene" is used for a group as defined in the definition for "$C_{1\text{-}n}$-alkylene" with at least two carbon atoms, if at least two of those carbon atoms of said group are bonded to each other by a triple bond.

By the term "$C_{1\text{-}6}$-alkoxy" (including those which are part of other groups) are meant branched and unbranched alkoxy groups with 1 to 6 carbon atoms and by the term "$C_{1\text{-}4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3\text{-}n}$-cycloalkyl", wherein n is an integer from 4 to n, either alone or in combination with another radical denotes a cyclic, saturated, unbranched hydrocarbon radical with 3 to n C atoms. For example the term $C_{3\text{-}7}$-cycloalkyl includes cyclopropyl, cyclobutyl, cyclopentyl, cyclohexyl and cycloheptyl.

The term "$C_{3\text{-}n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3\text{-}7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

In all cases of contradictions between structure and their naming, structure shall prevail.

5. PREFERRED EMBODIMENTS

The substituent X denotes Cl or Br, preferably Cl.
The substituent $R^1$ denotes $C_{1\text{-}4}$-alkyl-, $CH_3-O-C_{2\text{-}4}$-alkylene-, $HO-(CH_2)_n-O-C_{2\text{-}3}$-alkylene- or $HO-C_{2\text{-}6}$-alkylene-, preferably $C_{1\text{-}3}$-alkyl-, $CH_3-O-C_{2\text{-}3}$-alkylene-, $HO-(CH_2)_2-O-C_{2\text{-}3}$-alkylene- or $HO-C_{2\text{-}6}$-alkylene-, particularly preferred $C_{1\text{-}2}$-alkyl- or $CH_3-O-C_{2\text{-}3}$-alkylene-, also particularly preferred ethyl or a substituent of formula (aa)

(aa)

The substituent $R^2$ denotes $C_{1\text{-}4}$-alkyl-, $CH_3-O-C_{2\text{-}4}$-alkylene-, $HO-(CH_2)_n-O-C_{2\text{-}3}$-alkylene- or $HO-C_{2\text{-}6}$-alkylene-, preferably $C_{1\text{-}3}$-alkyl-, $CH_3-O-C_{2\text{-}3}$-alkylene-, $HO-(CH_2)_2-O-C_{2\text{-}3}$-alkylene- or $HO-C_{2\text{-}6}$-alkylene-, particularly preferred $C_{1\text{-}2}$-alkyl- or $HO-C_{2\text{-}6}$-alkylene-, also particularly preferred ethyl or a substituent of formula (ba)

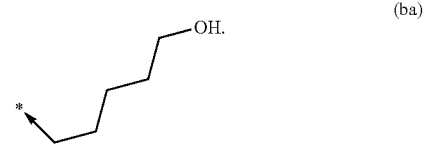

(ba)

The substituent $R^3$ denotes $HO-$, $(HO-C_{2\text{-}3}$-alkylene$)_2N-$, $(R^5O-)(R^6O-)P(O)-(CH_2)_n-O-$, $(HO-)((CH_3)_3N^+-(CH_2)_n-)P(O)-O-(CH_2)_n-O-$, $(R^5O-)(C_{1\text{-}3}$-alkyl-$)P(O)-O-(CH_2)_n-O-$, $R^7R^8N-C(O)-C_{1\text{-}2}$-alkylene-$O-$, $R^9R^{10}N-(CH_2)_n-O-$, $(CH_3)_3N^+-(CH_2)_n-O-$, $R^9R^{11}N-(CH_2)_n-O-$, $CH_3-(O-CH_2-CH_2)_m-O-$, $H-(O-CH_2-CH_2)_n-O-$, morpholino-$C(O)-$, $R^9R^{10}N-CH_2-$, $(CH_3)_3N^+-CH_2-$, 9-fluorenylmethyl-$O-C(O)-NR^9-CH_2-$, $R^9R^{10}N-CH_2-C(O)-NR^9-CH_2-$, $(CH_3)_3N^+-CH_2-C(O)-NR^9-CH_2-$, $R^9-O-C(O)-CH_2-NR^9-CH_2-$, $(R^9R^{10}N$-cyclohexyl-$NR^9-C(O)-)_2$phenyl-$O-CH_2-C(O)-NR^9-CH_2-$, tetrahydropyranyl-$O-$ or a substituent selected from the group consisting of formula (cae)

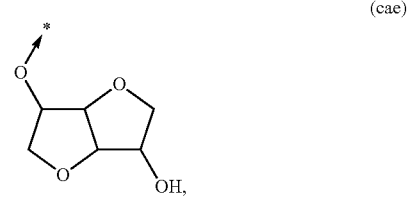

(cae)

preferably $HO-$, $(HO-C_{2\text{-}3}$-alkylene$)_2N-$, $(R^5O-)(R^6O-)P(O)-(CH_2)_n-O-$, $(HO-)((CH_3)_3N^+-$ $(CH_2)_3$—)P(O)—O—$(CH_2)_n$—O—, $R^7R^8N$—C(O)—$C_{1-2}$-alkylene-O—, $R^9R^{10}N$—$(CH_2)_n$—O—, $(CH_3)_3N^+$—$(CH_2)_2$—O—, $R^9R^{11}N$—$(CH_2)_n$—O—, $CH_3$—(O—$CH_2$—$CH_2)_n$—O—, morpholino-C(O)—, $R^9R^{10}N$—$CH_2$—, $(CH_3)_3N^+$—$CH_2$—, 9-fluorenylmethyl-O—C(O)—NH—$CH_2$—, $R^9R^{10}N$—$CH_2$—C(O)—NH—$CH_2$—, $(CH_3)_3N^+$—$CH_2$—C(O)—NH—$CH_2$—, $R^9$—O—C(O)—$CH_2$—NH—$CH_2$— or a substituent selected from the group consisting of formula (cae)-(caf)

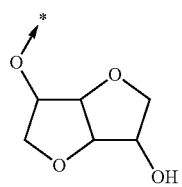

(cae)

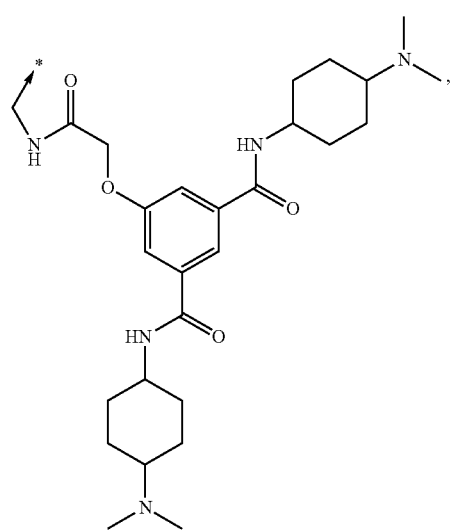

(caf)

preferably HO—, (HO—$CH_2CH_2)_2N$—, $(R^5O$—)$(R^6O$—)P(O)—$(CH_2)_n$—O—, (HO—)$((CH_3)_3N^+$—$(CH_2)_3$—)P(O)—O—$(CH_2)_n$—O—, $R^7R^8N$—C(O)—$C_{1-2}$-alkylene-O—, $R^9R^{10}N$—$(CH_2)_n$—O—, $(CH_3)_3N^+$—$(CH_2)_2$—O—, $R^9R^{11}N$—$(CH_2)_n$—O—, $CH_3$—(O—$CH_2$—$CH_2)_n$—O—, morpholino-C(O)—, $R^9R^{10}N$—$CH_2$—, $(CH_3)_3N^+$—$CH_2$—, 9-fluorenylmethyl-O—C(O)—NH—$CH_2$—, $R^9R^{10}N$—$CH_2$—C(O)—NH—$CH_2$—, $(CH_3)_3N^+$—$CH_2$—C(O)—NH—$CH_2$—, $R^9$—O—C(O)—$CH_2$—NH—$CH_2$— or a substituent selected from the group consisting of formula (cae)-(caf)

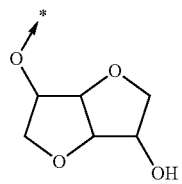

(cae)

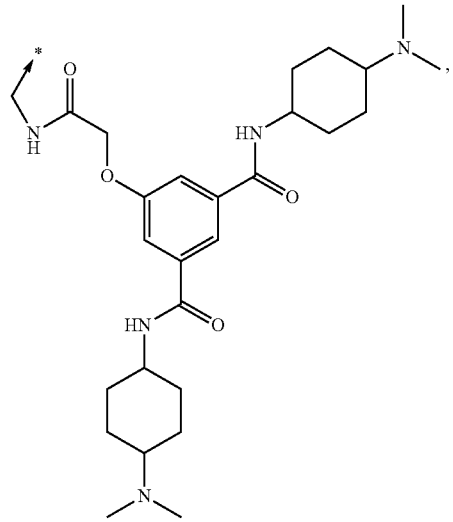

(caf)

particularly preferred is a substituent selected from the group consisting of formula (ca)-(cad)

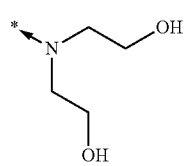

(ca)

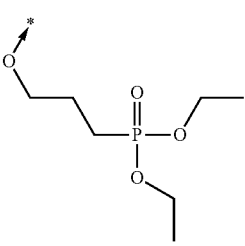

(cb)

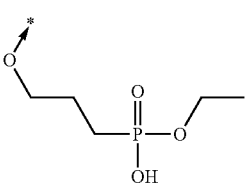

(cc)

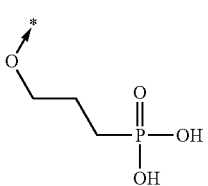

(cd)

33
-continued
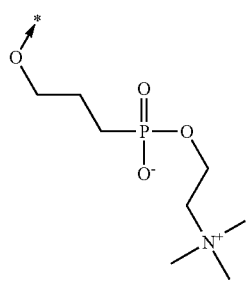
(ce)
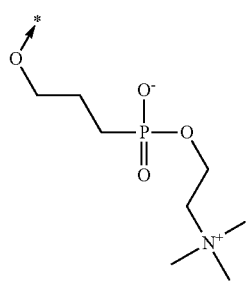
(cf)
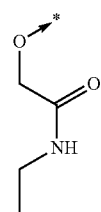
(cg)
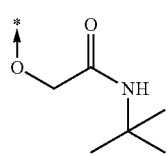
(ch)
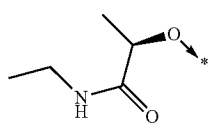
(ci)
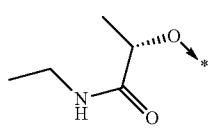
(cj)
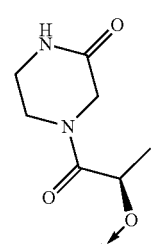
(ck)
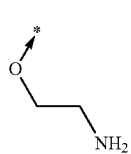
(cl)
34
-continued
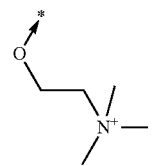
(cm)
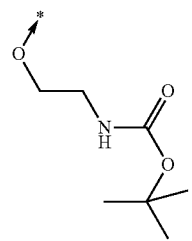
(cn)
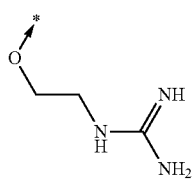
(co)
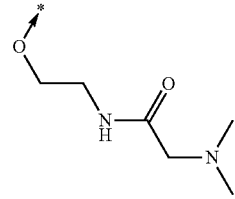
(cp)
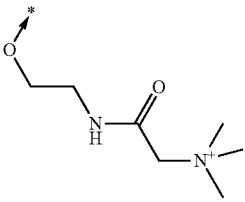
(cq)
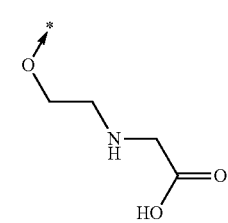
(cr)
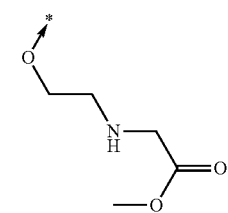
(cs)

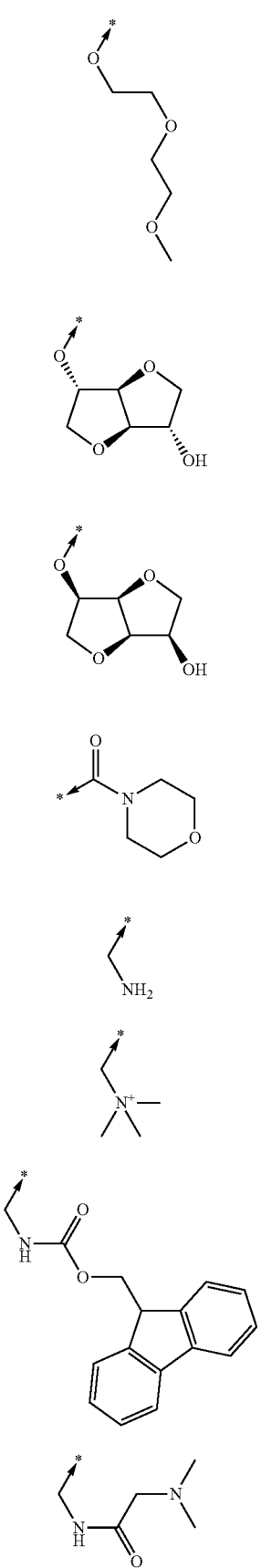
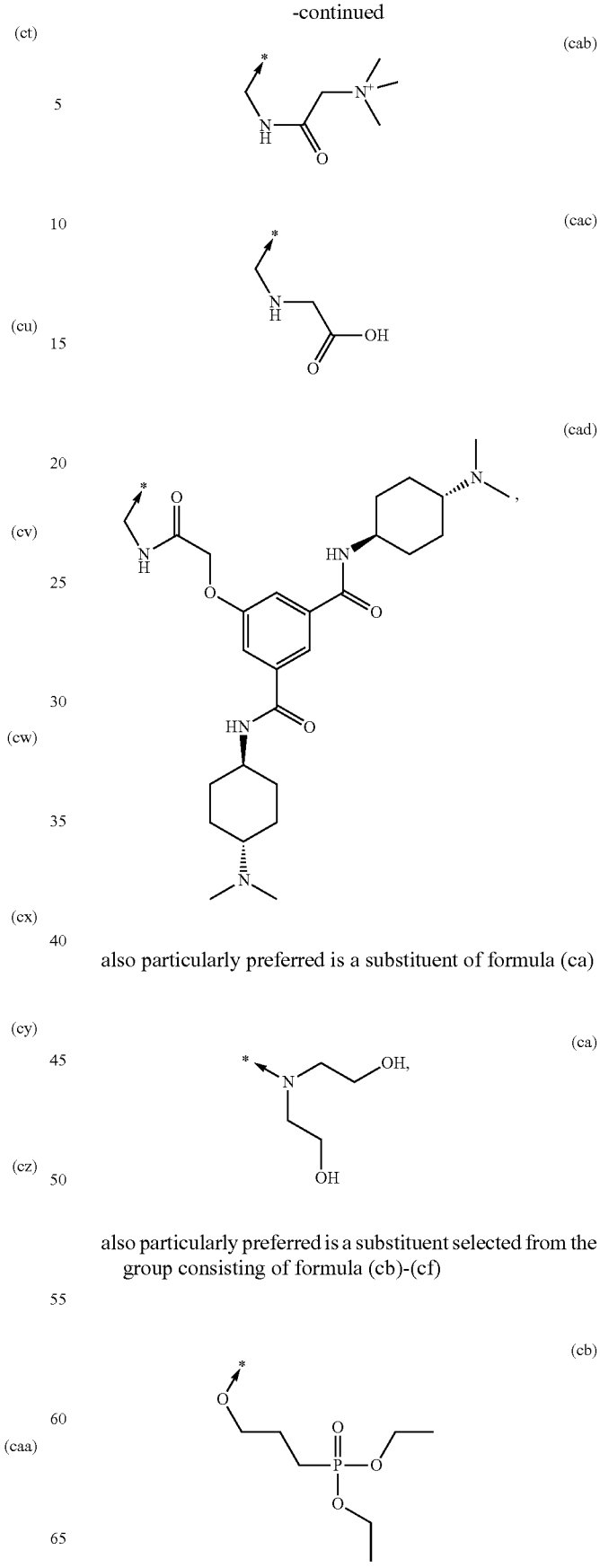
also particularly preferred is a substituent of formula (ca)
also particularly preferred is a substituent selected from the group consisting of formula (cb)-(cf)

-continued
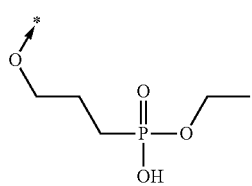
(cc)
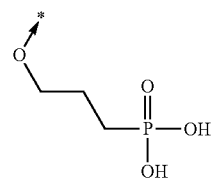
(cd)
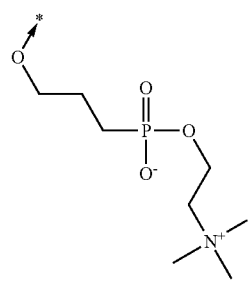
(ce)
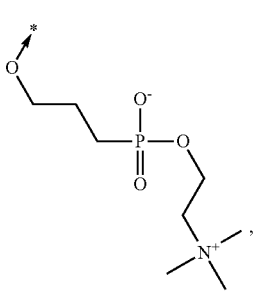
(cf)
also particularly preferred is a substituent selected from the group consisting of formula (cg)-(ck)
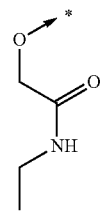
(cg)
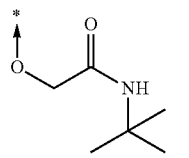
(ch)
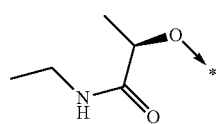
(ci)
-continued
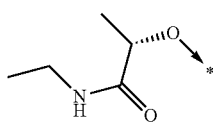
(cj)
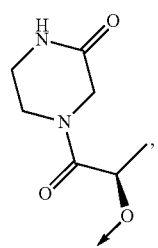
(ck)
also particularly preferred is a substituent selected from the group consisting of formula (cm), (cq), (cy), (cab)
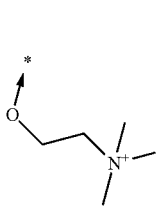
(cm)
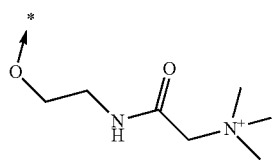
(cq)
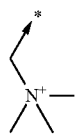
(cy)
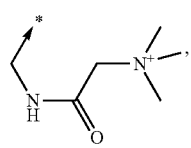
(cab)
also particularly preferred is a substituent selected from the group consisting of formula (cu)-(cv)
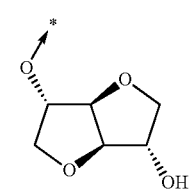
(cu)

(cv)

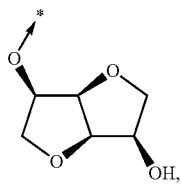

The substituent $R^4$ denotes H, halogen, or $(C_{1-4}\text{-alkyl-})NH-C(O)-$, preferably H, F or Cl, preferably F or Cl, particularly preferred F.

The substituent $R^5$ denotes H or $C_{1-3}$-alkyl-, preferably H or ethyl-.

The substituent $R^6$ denotes H, $C_{1-3}$-alkyl-, $CH_3-O-(CH_2)_n-$, tetrahydrofuryl-$CH_2-$ or $(CH_3)_3N^+-(CH_2)_n-$, preferably H, $C_{1-3}$-alkyl- or $(CH_3)_3N^+-(CH_2)_n-$, particularly preferred H or ethyl- or $(CH_3)_3N^+-(CH_2)_2-$.

The substituent $R^7$ denotes H, $C_{1-4}$-alkyl- or $(CH_3)_2P(O)-CH_2-O-(CH_2)_n-$, preferably H or $C_{1-4}$-alkyl-, particularly preferred H, ethyl- or $(CH_3)_3C-$.

The substituent $R^8$ denotes H, $C_{1-4}$-alkyl- or $(CH_3)_2P(O)-CH_2-O-(CH_2)_n-$, preferably H or $C_{1-4}$-alkyl-, particularly preferred H, ethyl- or $(CH_3)_3C-$, or the substituents $R^7$, $R^8$ together with the nitrogen atom they are attached to form a 5- or 6-membered heterocycle from the group consisting of pyrrolidine, morpholine, piperazine, piperazinone, N-methylpiperazine, N-methylpiperazinone, thiomorpholine, thiomorpholine-S-oxide or thiomorpholine sulfone, preferably a 6-membered heterocycle from the group consisting of piperazinone and thiomorpholine-S-oxide, particularly preferred is a piperazinone.

The substituent $R^9$ denotes H or methyl.

The substituent $R^{10}$ denotes H or methyl.

The substituent $R^{11}$ denotes $C_{1-4}$-alkyl-$O-C(O)-$, $NH_2-C(NH)-$, $R^9R^{10}N-CH_2-C(O)-$, $(CH_3)_3N^+-CH_2-C(O)-$ or $R^9-O-C(O)-CH_2-$, preferably $(CH_3)_3C-O-C(O)-$, $NH_2-C(NH)-$, $(CH_3)_2N-CH_2-C(O)-$, $(CH_3)_3N^+-CH_2-C(O)-$ or $R^9-O-C(O)-CH_2-$.

Variable m denotes 1, 2 or 3, preferably 2.

Variable n denotes 2 or 3.

The anion $Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate or p-toluenesulfonate, preferably chloride, iodide, formiate, trifluoroacetate.

Variable z denotes 0 for negatively charged substituents $R^1-R^4$, 1 for uncharged substituents $R^1-R^4$ or 2 for positively charged substituents $R^1-R^4$, and tautomers and optionally the pharmacologically acceptable acid addition salts thereof.

Any and each other of the substituents defined above may be combined with each other.

6. PREPARATION

The following methods are suitable for preparing compounds of general formula (I).

The compounds according to the invention may be obtained using methods of synthesis which are known to one skilled in the art and described in the literature of organic synthesis. General methods for functional groups protection and deprotection steps are described e.g. in: Greene, T. W. and Wuts, P. G. M. (eds.): Protective Groups in Organic Synthesis, third edition 1999; John Wiley and Sons, Inc. Preferably the compounds are obtained analogously to the methods of preparation explained more fully hereinafter, in particular as described in the experimental section.

Compounds of general formula (I) can be prepared by standard amidation procedures from amines of general formula (II) and the approprioate 3,5-diaminopyrazine-2-carboxylic acid applying e.g. the coupling reagent HATU. Amines (II) can be prepared from N-protected precursors of general formula (III) by standard deprotection procedures. Suitable protecting groups in (III) are e.g. BOC (wherein $R^{PG}$ denotes $-NHPG$ with PG denoting tertBuOC(O)$-$) and phthaloyl (wherein $R^{PG}$ denotes phthalimide). Compounds (III) can be prepared by alkylation of benzimidazoles of general formula (IIIa) applying alkylating agents $R^1$-LG. The leaving group LG can be e.g. Br or I.

Alternatively, compounds of general formula (I) can be prepared by alkylation of benzimidazoles of general formula (Ia) applying alkylating agents $R^1$-LG. The leaving group LG can be e.g. Br or I. Compounds of general formula (Ia) can be prepared by standard amidation procedures from amines of general formula (IIa) and the approprioate 3,5-diaminopyrazine-2-carboxylic acid applying e.g. the coupling reagent HATU. Amines (IIa) can be prepared from N-protected precursors of general formula (IIIa) by standard deprotection procedures. Suitable protecting groups in (IIIa) are e.g. BOC (wherein $R^{PG}$ denotes $-NHPG$ with PG denoting tert-BuOC(O)$-$) and phthaloyl (wherein $R^{PG}$ denotes phthalimide).

Benzimidazoles (IIIa) can be prepared from phenylenediamines (IV) in a two step procedure comprising (i) amidation with N-protected glycin using e.g. the coupling reagent TBTU and (ii) ring closure under acid catalysis, e.g. in glacial acetic acid at elevated temperature. Phenylenediamines can be prepared from the respective nitroanilins (V) by standard nitro reduction conditions (e.g. catalytic hydrogenation using raney-nickel as a catalyst).

Compounds (V) can be prepared from derivatives (VI) by nucleophilic substitution of the leaving group LG (e.g. F or Cl) with a primary amine $R^2-NH_2$ as nucleophile. Alternatively, compounds (V) can be accessed from nitroanilines (Va) by either alkylation (using an alkylating agent $R^2$-LG) or reductive amination (using an appropriate aldehyde) of the aromatic amino group. Compounds (I), (Ia), (III), (IIIa) and (V) can be modified using methods of synthesis which are known to the one skilled in the art and described in the literature of organic synthesis, preferably by functional group protection or deprotection steps, esterifications, amidation, hydrogenations, or 1,3-dipolar cycloadditions. Thereby, before such a modification, the structures of $R^1$, $R^2$, $R^3$, and $R^4$ may be beyond of what is claimed hereinafter.

The skilled person will appreciate that within these general synthesis schemes, the substituents $R^1$ and $R^2$ can in principle be interchanged, meaning that $R^2$ instead of $R^1$ can be introduced in the late alkylation step applying an alkylating agent $R^2$-LG.

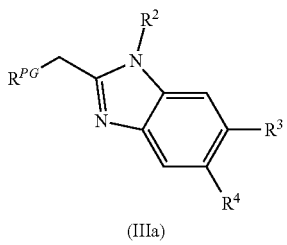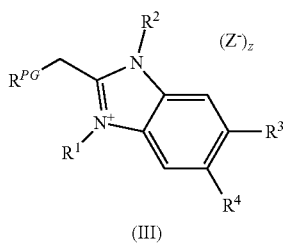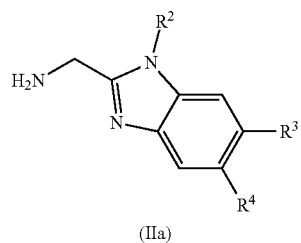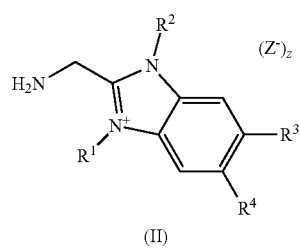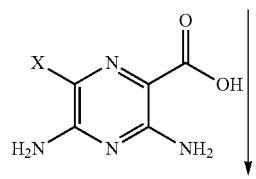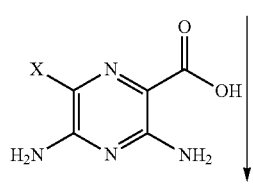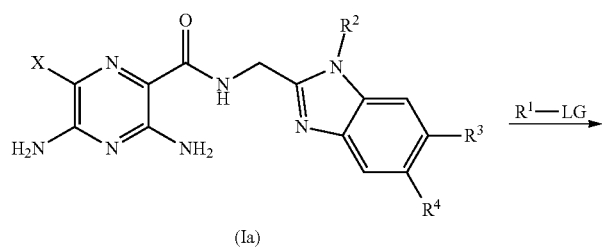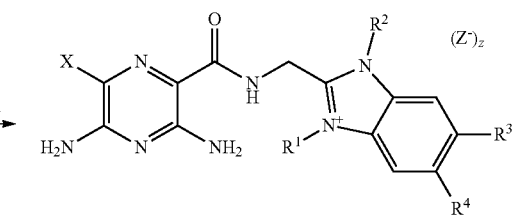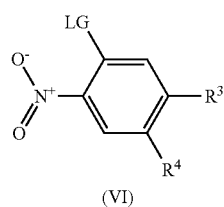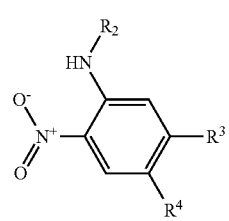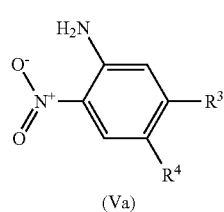

-continued

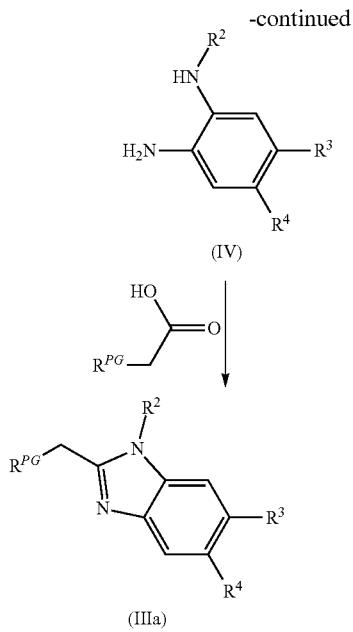

7. EXAMPLES

Other features and advantages of the present invention will become apparent from the following more detailed Examples which illustrate, by way of example, the principles of the invention.

Where no salt forms of compounds are specified, the compound may exist as a free base or a salt or a zwitterion, depending on the chemical structure, the synthesis conditions and the processes of workup and purification applied. The skilled person will appreciate that the compound is not limited to a certain salt form. Where salt forms of compounds are specified, the stoichiometry of the counterion is usually omitted. In case of multiply charged counterions the skilled person will appreciate that the resulting salt form is uncharged, leading to the corresponding stoichiometry. The skilled person will appreciate that the compound is not limited to the mono salt form and that it may exist as a disalt, trisalt or other compound:counterion stoichiometries. Furthermore, the skilled person will appreciate that such compound may unexpectedly exist as a salt with a different counterion, depending on the synthesis conditions and the processes of workup and purification applied. Solely for the purpose of yield determination, an estimate of the nature of the counterion and of compound:counterion stoichiometry is made (as indicated by the formula given).

7.1 Synthesis of Intermediates

Intermediate A.1

3,5-Diamino-6-chloropyrazine-2-carboxylic acid

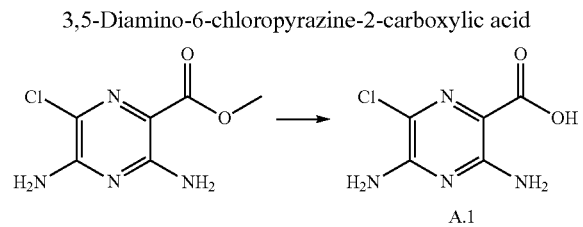

A mixture of methyl 3,5-diamino-6-chloropyrazine-2-carboxylate (100 g; 494 mmol), methanol (1 l) and NaOH (6 mol/l in water; 240 ml; 1.44 mol) is refluxed for 3 h. The mixture is allowed to cool to r.t. and then neutralized by addition of hydrochloric acid (6 mol/l in water; approx. 240 mL). Water (200 ml) is added. The precipitate formed is filtered off with suction, washed with water and dried at 60° C.

$C_5H_5ClN_4O_2$ ESI Mass spectrum: m/z=189 [M+H]+; m/z=187 [M−H]−

Intermediate A.2

3,5-Diamino-6-bromopyrazine-2-carboxylic acid

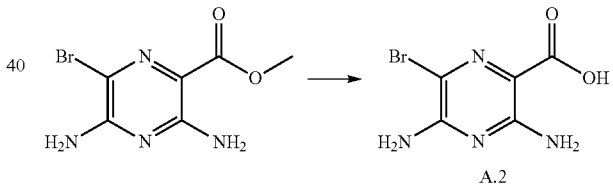

A.2 is prepared from methyl 3,5-diamino-6-bromopyrazine-2-carboxylate (which is prepared from methyl 3,5-diamino-6-chloropyrazine-2-carboxylate as described in J. Med. Chem., 10, (1967), 66-75) analogously to the procedure described for the synthesis of intermediate A.1.

Intermediate B.1

1-(tert-Butylcarbamoyl)prop-1-en-2-yl 3,5-diamino-6-chloropyrazine-2-carboxylate

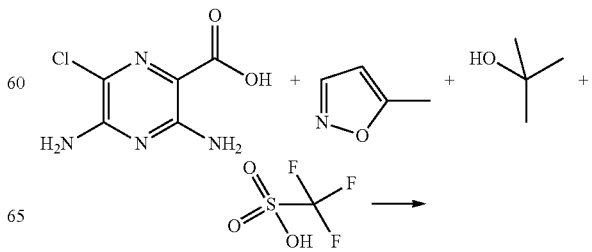

-continued

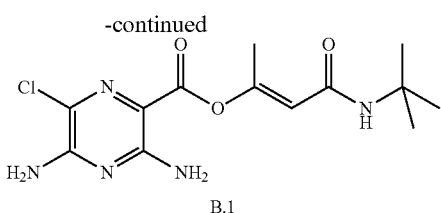

B.1

Stage 1:

A mixture of tert-butanol (21.0 mL; 226 mmol) and 5-methylisoxazole (18.0 mL; 221 mmol) is cooled with an ice-bath. Trifluoromethanesulphonic acid (20.0 mL; 221 mmol) is added dropwise with continued cooling. The resulting mixture is stirred for 1 h without further cooling.

Stage 2:

To a solution or suspension of 3,5-diamino-6-chloropyrazine-2-carboxylic acid (Intermediate A.1; 14.0 g; 74.2 mmol) and triethylamine (31.0 mL; 222 mmol) in DMF (100 mL) is added the mixture prepared in stage 1. The resulting mixture is stirred for 4 h at r.t. Ice-water is added with stirring. The precipitate formed is filtered off with suction, washed with water and dried at 65° C. to yield the title compound.

$C_{13}H_{18}ClN_5O_3$ ESI Mass spectrum: m/z=328 [M+H]+; m/z=326 [M−H]−

TLC (Silica; DCM/MeOH 9:1): $R_f$=0.4

Intermediate I.1

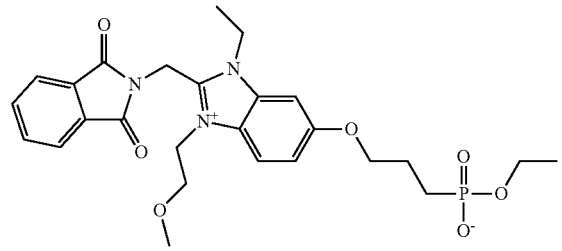

I.1

A mixture of intermediate II.1 (1.20 g; 1.79 mmol), lithium bromide (1.55 g; 17.9 mmol) and DMF (10 ml) is stirred over night at 100° C. Volatiles are evaporated and the residue is purified by RP-HPLC (Sunfire; water/ACN, modifier: TFA).

$C_{26}H_{32}N_3O_7P$ ESI Mass spectrum: m/z=530 [M+H]+

Intermediate II.1

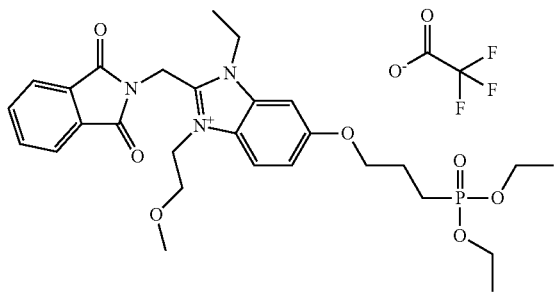

II.1

A mixture of benzimidazole intermediate VI.3 (3.00 g; 6.01 mmol), 2-bromoethyl methyl ether (5.00 ml; 52.9 mmol) and ACN (15 ml) is stirred at 120° C. for 5 h. Volatiles are evaporated and the residue is purified by RP-HPLC (Sunfire; water/ACN, modifier: TFA).

$C_{28}H_{37}N_3O_7P×C_2F_3O_2$ ESI Mass spectrum: m/z=558 [M]+

HPLC analytics: RT=0.74 min (HPLC method 2)

The following intermediates are prepared accordingly from the respective benzimidazole and the respective alkyl halide as indicated. Due to conditions applied, the syntheses may yield a free base, a TFA salt or other salt forms which can be applied equally to the syntheses of example compounds described below.

| Example | Structure | Benzidazole applied | Alkyl halide applied | Synthesis comment |
|---|---|---|---|---|
| II.2 | 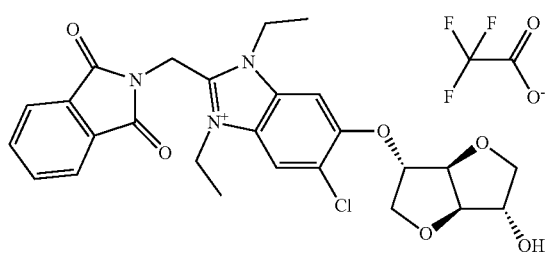 | VI.1 | Iodoethane | |
| II.3 | 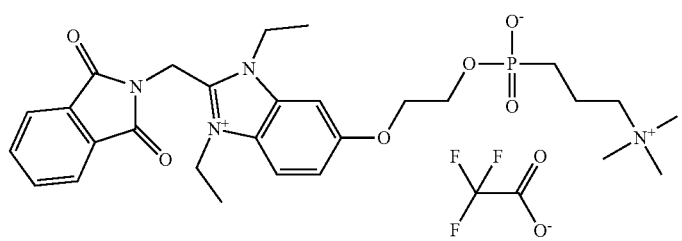 | XXXI.1 | Iodoethane | |

| Example | Structure | Benzidazole applied | Alkyl halide applied | Synthesis comment |
|---|---|---|---|---|
| II.4 | 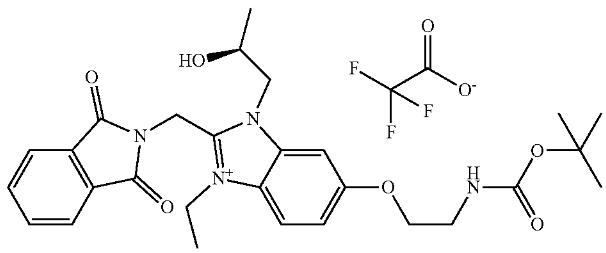 | VI.8 | Iodoethane | |
| II.5 | 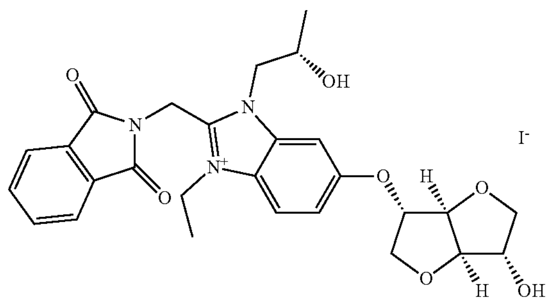 | VI.10 | Iodoethane | |

Intermediate III.1

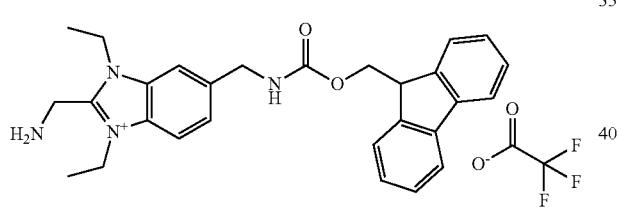

Intermediate XV.1 (1.10 g; 1.29 mmol) in TFA (10% in DCM; 20 ml) is stirred at r.t. for 3 h. The solvent is evaporated to yield the title compound as a crude product that is further reacted without purification.

$C_{28}H_{31}N_4O_2 \times C_2F_3O_2$

Intermediate III.2

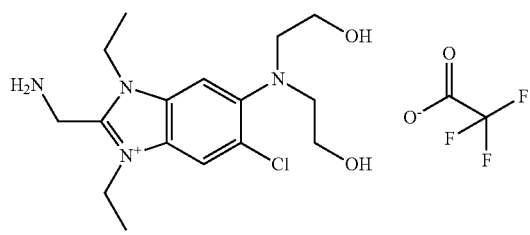

The title compound is prepared from intermediate XX.2 analogously to the procedure described for the synthesis of intermediate III.1.

$C_{16}H_{26}ClN_4O_2 \times C_2F_3O_2$ ESI Mass spectrum: m/z=341 [M]+

Intermediate IV.1

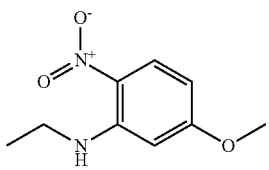

A mixture of 2-fluoro-4-methoxy-1-nitro-benzene (17.3 g; 0.10 mol) and ethylamine (2M in THF; 180 ml; 360 mmol) is stirred for 1 h at 90° C. (microwave heating). The mixture is diluted with water and extracted with ethyl acetate. The organic layer is separated, dried and evaporated.

$C_9H_{12}N_2O_3$ ESI Mass spectrum: m/z=197 [M+H]+

The following intermediates are prepared accordingly from the respective amine and the respective aryl halide as indicated. Due to conditions applied, the syntheses may yield a free base, a TFA salt or other salt forms which can be applied equally to the syntheses of example compounds described below.

| Example | Structure | Amine applied | Aryl halide applied | Synthesis comment |
|---------|-----------|---------------|---------------------|-------------------|
| IV.2 | 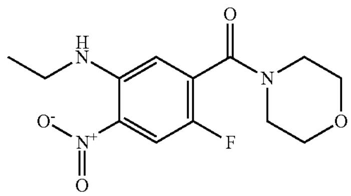 | | see footnote a | Reaction at r.t. for 6 h; extraction with DCM |
| IV.3 | 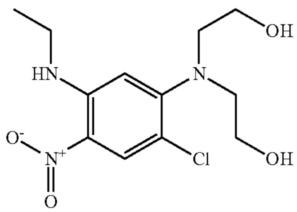 | | | See footnote b |
| IV.4 | 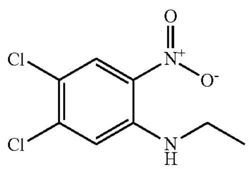 | | | Addition of $K_2CO_2$ (2.0 eq) |
| IV.5 | 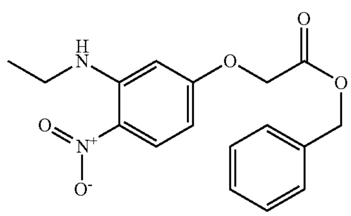 | | VII.2 | Addition of $K_2CO_2$ (2.5 eq) |
| IV.6 | 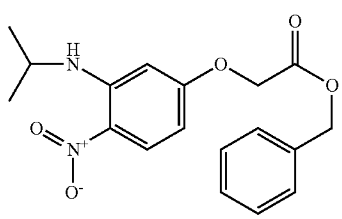 | | VII.2 | Addition of $K_2CO_2$ (2.5 eq) |
| IV.7 | 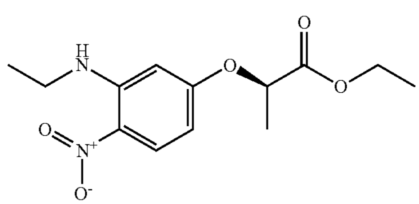 | | XXVIII.1 | Addition of $K_2CO_2$ (2.5 eq); solvent ist DMF |
| IV.8 | 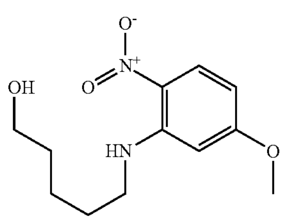 | | | Addition of $K_2CO_2$ (1.3 eq); solvent ist DMF |

-continued

| Example | Structure | Amine applied | Aryl halide applied | Synthesis comment |
|---|---|---|---|---|
| IV.9 | 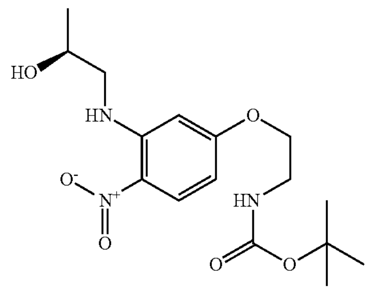 | | VII.3 | Reaction at 80° C. overnight; extraction with DCM |
| IV.10 | 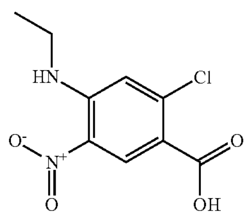 | | | Reaction in water at r.t. |
| IV.11 | | | | Reaction in methyl-THF at r.t.; 1 eq of amine and one eq. of K₂CO₃ | a: prepared from 2,5-Difluoro-4-nitro-benzoyl chloride and morpholine (2 eq.) in DCM.
b: reaction at r.t. for 2 h. 1.1 eq. of amine applied. Purification by silica gel chromatography (DCM/methanol 2% –> 6%)

Intermediate V.1

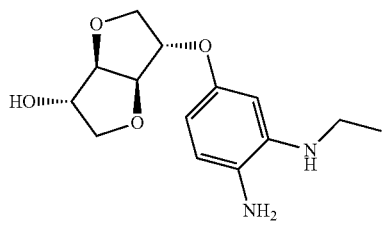

V.1

Intermediate XVI.3 (2.07 g; 4.76 mmol) in methanol (40 ml) is hydrogenated in a Parr apparatus (r.t., 50 psi hydrogen; catalyst: Pd/C 5%; 0.4 g). The catalyst is filtered off under nitrogen and the filtrate is applied directly to the next reaction step as described there.

The following intermediates are prepared accordingly from the respective nitro-benzene as indicated. Due to conditions applied, the syntheses may yield a free base, a TFA salt or other salt forms which can be applied equally to the syntheses of example compounds described below.

| Example | Structure | Nitro-benzene applied | Synthesis comment |
|---|---|---|---|
| V.2 | 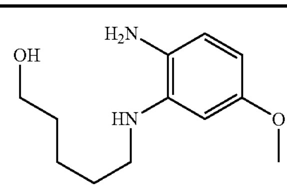 | IV.8 | |

-continued

| Example | Structure | Nitrobenzene applied | Synthesis comment |
|---|---|---|---|
| V.3 | 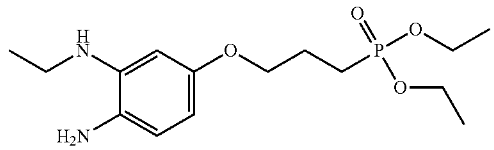 | VIII.1 | Solvent is THF |
| V.4 | 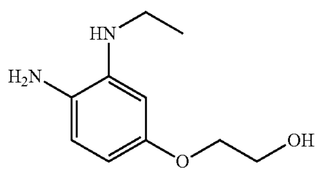 | See footnote a | Solvent is ethanol |
| V.5 | 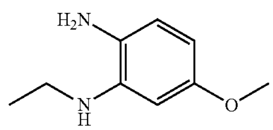 | IV.1 | |
| V.6 | 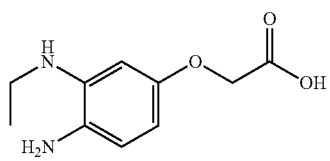 | IV.5 | Solvent is ethanol |
| V.7 | 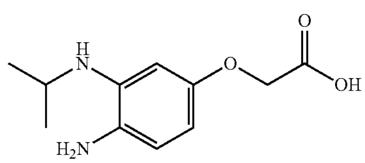 | IV.6 | Solvent is ethanol and HCl (aq. solution; 1.3M) |
| V.8 | 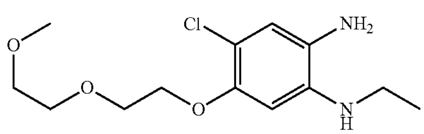 | XXV.1 | |
| V.9 | 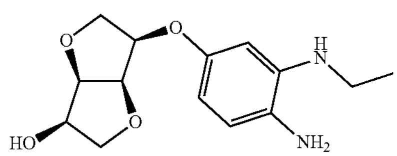 | XVI.2 | After 2 days fresh catalyst is added, further reaction for 2.5 days |
| V.10 | 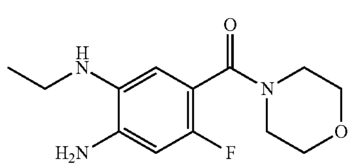 | IV.2 | Solvent is ethanol |
| V.11 | 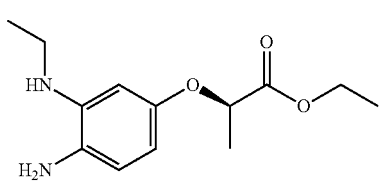 | IV.7 | Solvent is ethanol |

| Example | Structure | Nitrobenzene applied | Synthesis comment |
|---|---|---|---|
| V.12 | 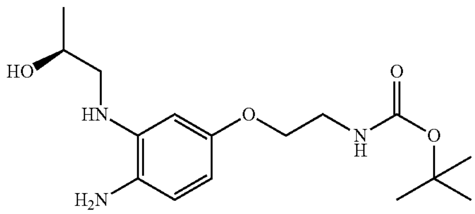 | IV.9 | Catalyst is Raney-Ni |
| V.13 | 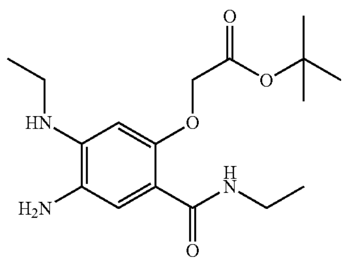 | VII.4 | |
| V.14 | | XVI.4 | Solvent is THF; catalyst is Raney-Ni | a: the starting material N-ethyl-2-nitro-5-(hydroxyethoxy)-anilin is prepared from 2,4-difluorobenzene, ethylamine and ethylene glycol analogously to intermediate XXXIII.1

Intermediate VI.1

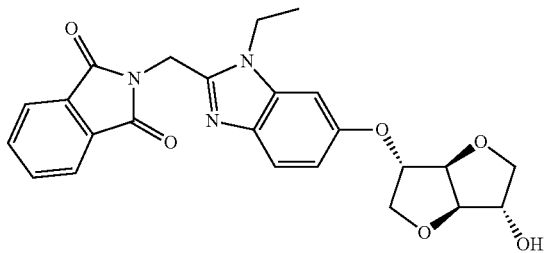

VI.1

The diaminobenzene intermediate V.1 (1.20 g; 4.28 mmol) is added to a preincubated (15 min) mixture of N-phthaloylglycine (0.882 g; 4.3 mmol), TBTU (1.50 g; 4.67 mmol) and TEA (0.80 ml; 5.77 mmol) and DMF (40 ml). The mixture is stirred at r.t. for 3 h, poured on aq. Sodium carbonate. The precipitate is filtered off, dried, and taken up in glacial acetic acid (40 ml) and refluxed for 1 h. The mixture is evaporated. The residue is purified by silica gel chromatography (DCM/methanol 2%→6%) to yield the title compound.

$C_{24}H_{23}N_3O_6$ ESI Mass spectrum: m/z=450 [M+H]+

The following intermediates are prepared accordingly from the respective diaminobenzenes as indicated. Due to conditions applied, the syntheses may yield a free base, a TFA salt or other salt forms which can be applied equally to the syntheses of example compounds described below.

| Example | Structure | Diaminobenzene applied | Synthesis comment |
|---|---|---|---|
| VI.2 | 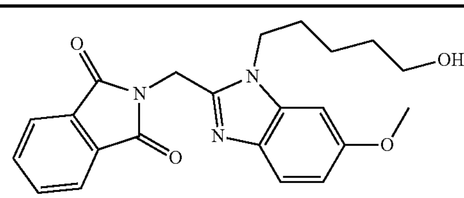 | V.2 | |

-continued

| Example | Structure | Diamino-benzene applied | Synthesis comment |
|---------|-----------|-------------------------|-------------------|
| VI.3 | 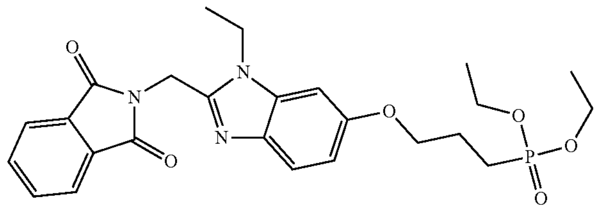 | V.3 | |
| VI.4 | 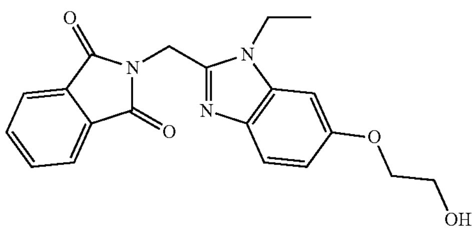 | V.4 | |
| VI.5 | 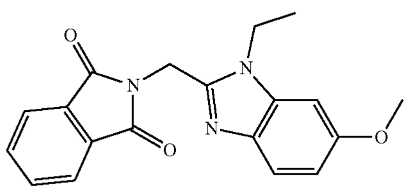 | V.5 | |
| VI.6 | 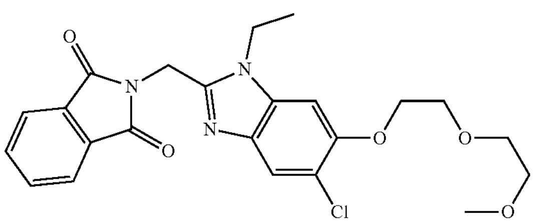 | V.8 | |
| VI.7 | 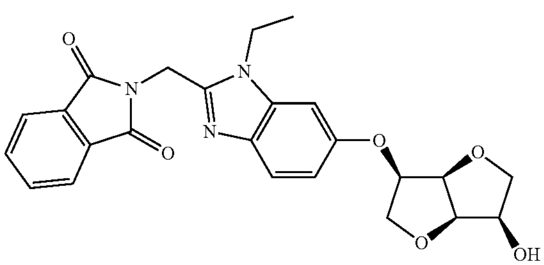 | V.9 | |
| VI.8 | | V.12 | Before chromatographic purification, the crude product is stirred in BOC$_2$O/diethyl ether for 1h at RT, evaporated. |

-continued

| Example | Structure | Diaminobenzene applied | Synthesis comment |
|---|---|---|---|
| V1.9 | 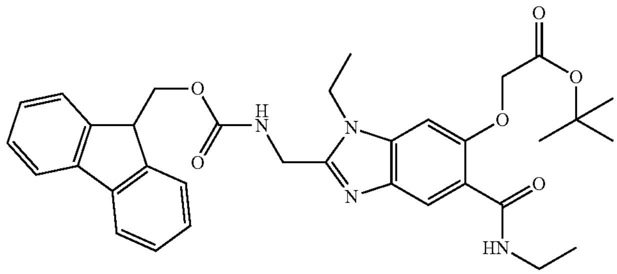 | V.13 | N-fluorenylmethoxycarbonyl-glycin applied instead of N-phthaloylglycine |
| V1.10 | Chiral | V.14 | Ring closing step performed in HCl (4M in dioxane) |

Intermediate VII.1

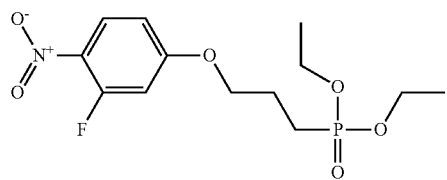

VII.1

A mixture of 3-fluoro-4-nitrophenol (2.56 g; 16.30 mmol), diethyl(3-bromopropyl)-phosphonate (3.26 ml; 16.98 mmol) and potassium carbonate (2.48 g; 17.9 mmol) in ACN (20 ml) is stirred for 4 h at 80° C. After cooling to r.t. the insoluble material is filtered off and discarded. The mother liquor is evaporated.

$C_{13}H_{19}FNO_6P$ ESI Mass spectrum: m/z=336 [M+H]+

The following intermediates are prepared accordingly from the respective nitrophenols and alkyl halides as indicated. Due to conditions applied, the syntheses may yield a free base, a TFA salt or other salt forms which can be applied equally to the syntheses of example compounds described below.

| Example | Structure | Nitrophenol applied | Alkyl halide applied | Synthesis comment |
|---|---|---|---|---|
| VII.2 | 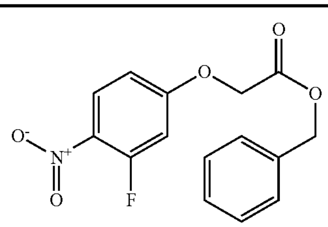 | | | Solvent is DMF, purification by extraction with water |
| VII.3 | 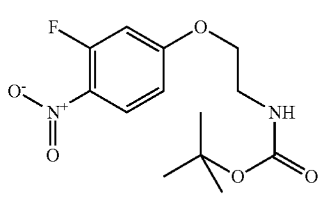 | | | Reaction in acetone; purification by silica gel chromatography (DCM/cyclohexane) |

-continued

| Example | Structure | Nitrophenol applied | Alkyl halide applied | Synthesis comment |
|---|---|---|---|---|
| VII.4 | 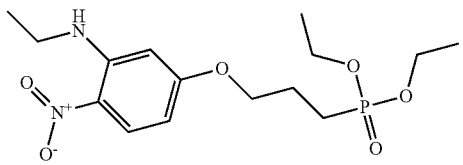 | XXVII.2 | 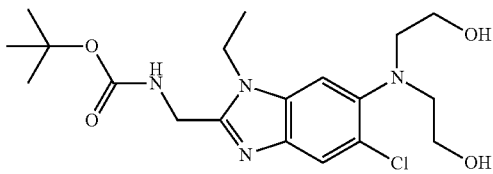 | Reaction in DMF at r.t. over night |

Intermediate VIII.1

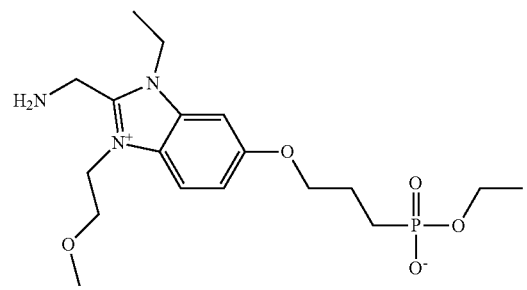

VIII.1

A mixture of intermediate VII.1 (23.58 g; 63.30 mmol) and ethyl amine (2 M in THF; 80.0 ml; 160 mmol) is stirred at 90° C. for 1 h (microwave heating). The mixture is diluted with ethyl acetate and washed with water. The organic layer is separated, dried and evaporated.

$C_{15}H_{25}N_2O_6P$ ESI Mass spectrum: m/z=361 [M+H]+
HPLC analytics: RT=0.69 min (HPLC method 1)

Intermediate IX.1

IX.1

To a mixture of intermediate IV.3 (500 mg; 1.65 mmol) and tert-butyl N-(2-oxoethyl)carbamate (265 mg; 1.67 mmol) in ethanol (15 ml) is added dropwise a solution of sodium dithionite (1.50 g; 7.32 mmol) in water (10 ml). The mixture is stirred at 50° C. for 5 h. Ethyl acetate is added and the mixture is extracted with aq. Sodium carbonate. The organic layer is separated, dried with sodium sulphate and evaporated. The residue is purified by silica gel chromatography (DCM/methanol 3%→6%) to yield the title compound.

$C_{19}H_{29}ClN_4O_4$ ESI Mass spectrum: m/z=413 [M+H]+

Intermediate X.1

X.1

A mixture of intermediate I.1 (0.860 g; 1.34 mmol) and hydrazine hydrate (0.195 mL; 4.09 mmol) in methanol (20 mL) is stirred at 60° C. over night. After cooling to r.t., precipitates are filtered off. The mother liquor is evaporated to yield the title compound.

$C_{18}H_{30}N_3O_5P$ ESI Mass spectrum: m/z=400 [M+]

The following intermediates are prepared accordingly from the respective protected amine as indicated. Due to conditions applied, the syntheses may yield a free base, a TFA salt or other salt forms which can be applied equally to the syntheses of example compounds described below.

| Example | Structure | Protected amine applied | Synthesis comment |
|---|---|---|---|
| X.2 | 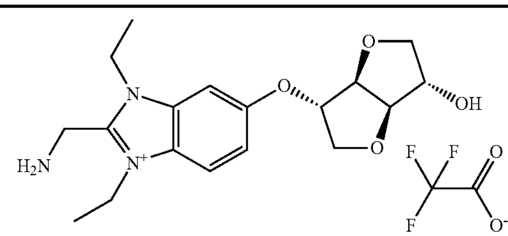 | II.2 | |

-continued

| Example | Structure | Protected amine applied | Synthesis comment |
|---------|-----------|-------------------------|-------------------|
| X.3 | 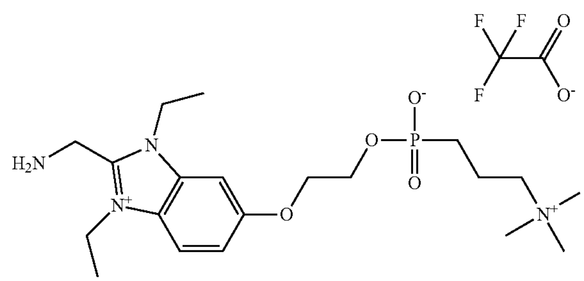 | II.3 | |
| X.4 | 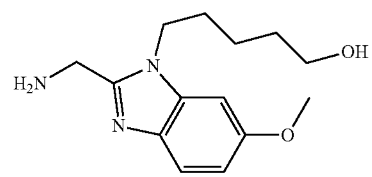 | VI.2 | |
| X.5 | 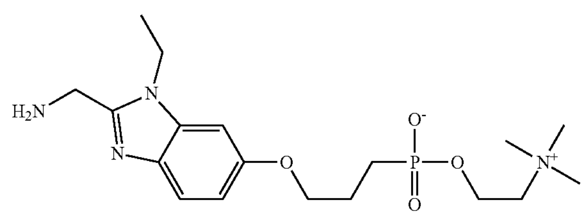 | XXIX.1 | Product precipitates during reaction |
| X.6 | 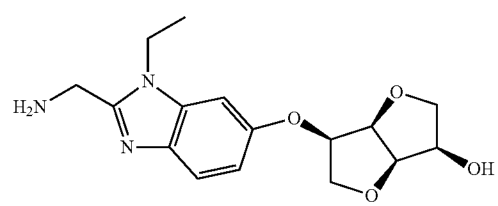 | VI.7 | |
| X.7 | 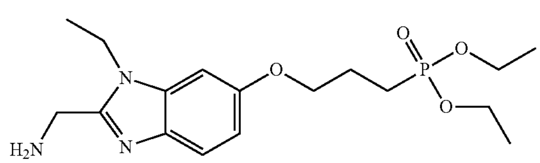 | VI.3 | |
| X.8 | 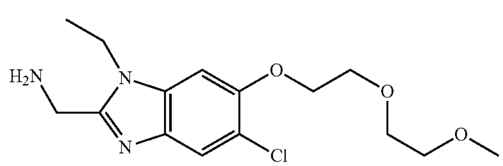 | VI.6 | |
| X.9 | 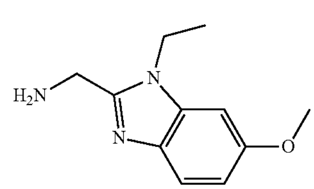 | VI.5 | |

| Example | Structure | Protected amine applied | Synthesis comment |
|---|---|---|---|
| X.10 | 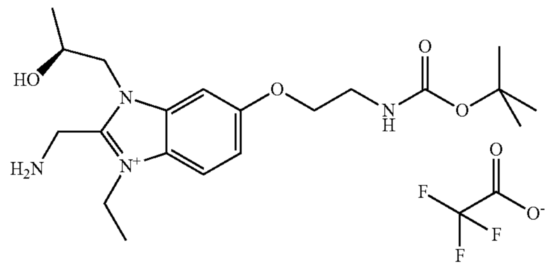 | II.4 | |
| X.11 | 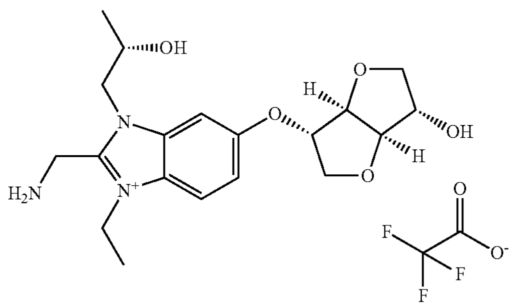 | II.5 | |

Intermediate XI.1

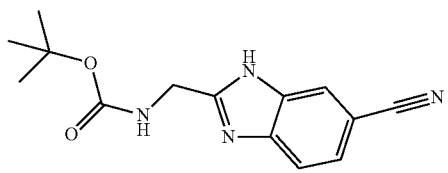

XI.1

A mixture of tert-butoxycarbonylamino-acetic acid (4.14 g; 23.66 mmol), TBTU (7.60 g; 23.66 mmol) and TEA (4.68 mL; 33.80 mmol) in DCM (80 mL) is stirred at r.t. for 30 min. 3,4-Diaminos benzonitrile (3.00 g; 22.5 mmol) is added. After stirring over night at r.t. the mixture is diluted with DCM and washed with NaOH (aq. solution; 1 M). The organic layer is separated and evaporated. The residue is stirred in diethyl ether, filtered off and dried. The resulting amide intermediate is taken up in glacial acetic acid (40 ml) and stirred at r.t. for 3 days. Additional acetic acid (25 ml) is added and stirred over night. The mixture is evaporated.

$C_{14}H_{16}N_4O_2$ ESI Mass spectrum: m/z=273 [M+H]+

Intermediate XII.1

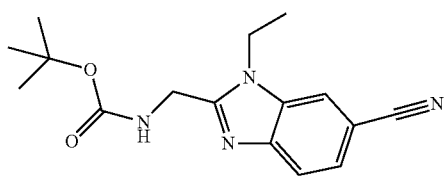

XII.1

A mixture of intermediate XI.1 (4.00 g; 13.22 mmol) and LiHMDS (in THF; 1M; 13.9 ml; 13.9 mmol) in THF 30 ml) is stirred at r.t. for 15 min. Ethyl iodide (1.28 mL; 15.86 mmol) is added and the mixture is stirred at 50° C. over night. The mixture is evaporated and the residue is purified by silica gel column chromatography (gradient: DCM/methanol 0-2%).

$C_{16}H_{20}N_4O_2$ ESI Mass spectrum: m/z=299 [M−H]−

Regioisomeric mixture (1:1)

Intermediate XIII.1

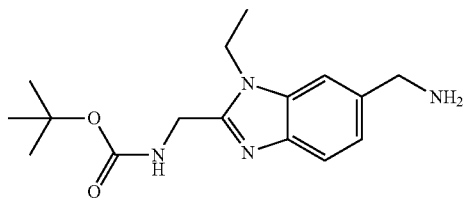

XIII.1

Intermediate XII.1 (2.50 g; 8.32 mmol) in methanol/ammonia (200 ml) is hydrogenated in a Parr apparatus (r.t.; 3 bar hydrogen; catalyst: 1.20 g Raney-Nickel). The catalyst is filtered off and the solvent is evaporated.

$C_{16}H_{24}N_4O_2$ HPLC analytics: RT=0.32 min (HPLC method 1)

Intermediate XIV.1

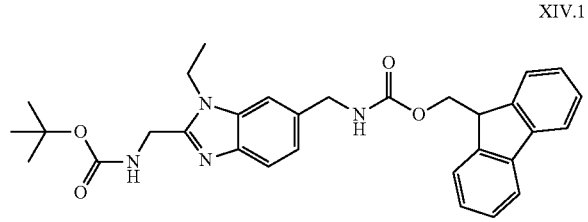

XIV.1

A mixture of Intermediate XIII.1 (2.13 g; 7.00 mmol), 9-fluorenylmethyl chloroformate (1.99 g; 7.70 mmol) and potassium carbonate (1.06 g; 7.70 mmol) in THF (60 ml) and dioxane (60 ml) is stirred at r.t. for 3 h. The solvent is evaporated. The residue is taken up in DCM and washed with water. The organic layer is separated, dried and evaporated to yield the title compound as a crude product that is further reacted without purification.

$C_{31}H_{34}N_4O_4$ ESI Mass spectrum: m/z=527 [M+H]+

Intermediate XV.1

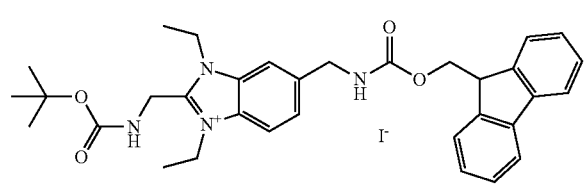

A mixture of Intermediate XIV.1 (2.00 g; 3.80 mmol) and ethyl iodide (4.89 ml; 60.76 mmol) in THF (10 mL) is stirred at 120° C. for 1.25 h in a microwave. The solvent is evaporated to yield the title compound as a crude product that is further reacted without purification.

$C_{33}H_{39}N_4O_4 \times I$

Intermediate XVI.1

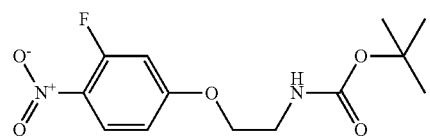

A mixture of 3-fluoro-4-nitro-phenol (25.29 g; 0.16 mol), N-(2-bromoethyl)carbaminic acid (1,1)dimethyl)ethyl ester (36.08 g; 0.16 mol) and potassium carbonate (24.48 g; 0.18 mol) in acetone is refluxed for 8 h. The mixture is evaporated and the residue is purified by silica gel chromatography (eluent: DCM/methanol 100/1).

$C_{13}H_{17}FN_2O_5$

Intermediate XVI.2

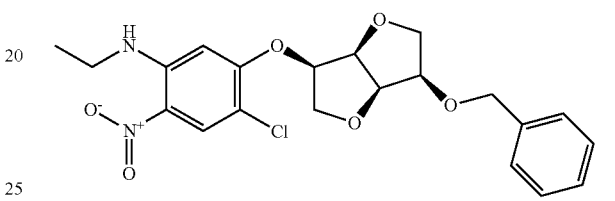

A mixture of aryl halide intermediate IV.4 (1.0 g; 4.25 mmol), the alcohol (3R,3AR,6R,6AR)-6-benzyloxy-2,3,3A,5,6,6A-hexahydrofuro[3,2b]furan-3-ol and sodium hydride (55% in mineral oil; 223 mg; 5.10 mmol) in DMF (20 ml) is stirred at r.t. for 3 h. The mixture is evaporated. The residue is taken up in DCM and washed with water. The organic layer is separated, dried and evaporated.

$C_{21}H_{23}ClN_2O_6$ ESI Mass spectrum: m/z=435 [M+H]+

The following intermediates are prepared accordingly from the respective aryl halide and the respective alcohol as indicated. Due to conditions applied, the syntheses may yield a free base, a TFA salt or other salt forms which can be applied equally to the syntheses of example compounds described below.

| Example | Structure | Aryl halide applied | alcohol applied | Synthesis comment |
|---|---|---|---|---|
| XVI.3 | 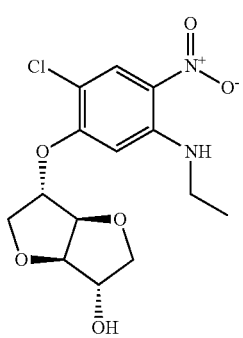 | 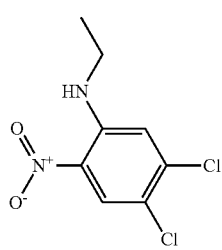 | 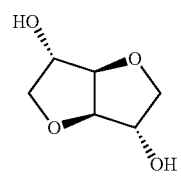 (D-Isoidide) | Crude product purified by silica gel column chromatography (DCM/methanol 2% → 4%) |

| Example | Structure | Aryl halide applied | alcohol applied | Synthesis comment |
|---|---|---|---|---|
| XVI.4 | 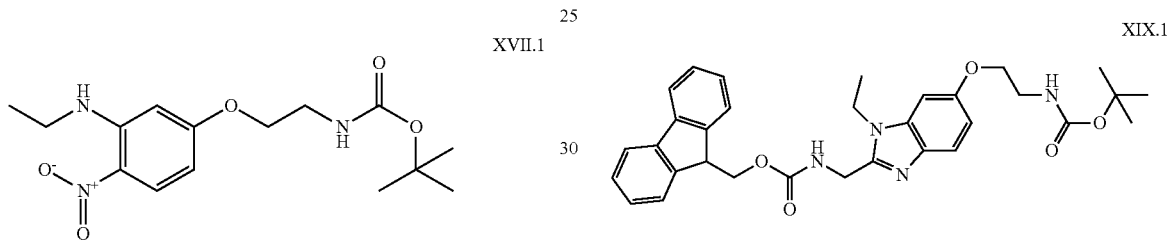 (D-Isoidide) | IV.11 | HO, O, OH | Reaction at 70° C. over night; purification by silica gel chromatography (DCM/ MeOH 0 → 8%) |

Intermediate XVII.1

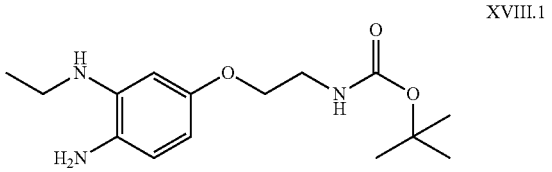
XVII.1

A mixture of Intermediate XVI.1 (19.1 g; 63.6 mmol), ethylamine (2 M in THF; 47.7 ml; 95.4 mmol) and potassium carbonate (14.0 g; 102 mmol) in THF (300 ml) is stirred at 50° C. for 2 h and at r.t. for 3 days. Insolubles are filtered off and discarded, the mother liquor is evaporated. The residue is taken up in DCM and washed with water. The organic layer is separated, dried and evaporated.

$C_{15}H_{23}N_3O_5$ ESI Mass spectrum: m/z=326 [M+H]+

Intermediate XVIII.1

XVIII.1

Intermediate XVII.1 (13.3 g; 40.9 mmol) in methanol (500 ml) is hydrogenated in a Parr apparatus (r.t.; 3 bar hydrogen; catalyst: 1.30 g Pd/C 10%). The catalyst is filtered off and the solvent is evaporated.

$C_{15}H_{25}N_3O_3$

Intermediate XIX.1

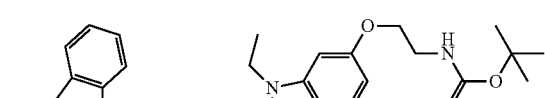
XIX.1

A mixture of Intermediate XVIII.1 (12.00 g; 40.63 mmol), (9H-fluoren-9-ylmethoxycarbonylamino)-acetic acid (12.08 g; 40.63 mmol), the coupling reagent HATU (16.99 g; 44.69 mmol) and DIPEA (13.91 mL; 81.25 mmol) in DMF (50 ml) is stirred at r.t. for 1 h. The mixture is evaporated. The residue is taken up in glacial acetic acid (50 mL) and stirred at 60° C. for 3 h. The solvent is evaporated. The residue is taken up in DCM and washed with water and $NaHCO_3$ (sat. aq. solution). The organic layer is separated, dried and evaporated. The residue is purified by silica gel chromatography (eluent: DCM/methanol 40/1).

$C_{32}H_{36}N_4O_5$ ESI Mass spectrum: m/z=557 [M+H]+
HPLC analytics: RT=0.63 min (HPLC method 3)

Intermediate XX.1

XX.1

A mixture of intermediate XIX.1 (9.60 g; 17.3 mmol) and ethyl iodide (20.7 ml; 259 mmol) in THF (90 ml) is stirred at 120° C. for 2 h (microwave heating). The mixture is evaporated and the residue is purified by silica gel chromatography (eluent: DCM/methanol 30/1). The residue is stirred in diethyl ether, filtered off and dried.

$C_{34}H_{41}N_4O_5 \times I$ ESI Mass spectrum: m/z=585 [M+]

The following intermediates are prepared accordingly from the respective benzimidazole and the respective alkyl halide as indicated. Due to conditions applied, the syntheses may yield a free base, a TFA salt or other salt forms which can be applied equally to the syntheses of example compounds described below.

| Example | Structure | Benzimidazole applied | Alkyl halide applied | Synthesis comment |
|---|---|---|---|---|
| XX.2 | 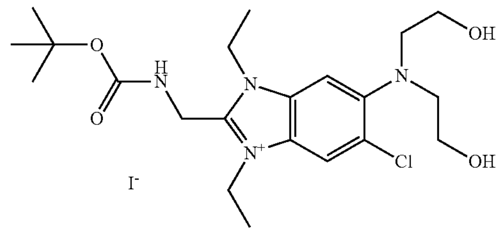 | IX.1 | Iodoethane | |
| XX.3 | 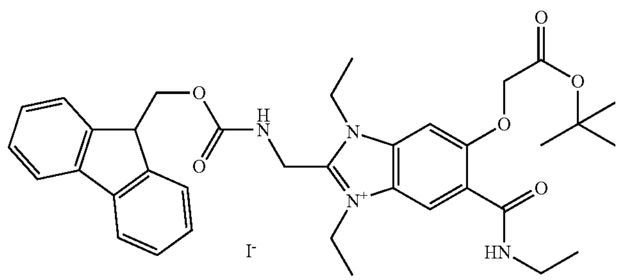 | VI.9 | Iodoethane | Precpipated product is filtered off and washed with diethyl ether |

Intermediate XXI.1

XXI.1

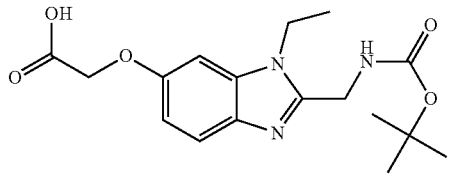

To a mixture of Intermediate V.6 (38.6 g; 126 mmol) and tert-butyl N-(2-oxoethyl)carbamate (9.00 g; 56.6 mmol) in water (50 mL) and DMF (100 mL) glacial acetic acid (10 ml) was added and the mixture was stirred at r.t. over night. Additional tert-butyl N-(2-oxoethyl)carbamate (9.00 g; 56.6 mmol) is added. After stirring for 2 h the insoluble material is filtered off and the filtrate is evaporated. The residue is stirred in ACN, filtered off, washed with ACN and dried. The mother liquor is evaporated and the residue is again stirred in less ACN. The precipitate is filtered off and dried. Both obtained solids are combined.

$C_{17}H_{23}N_3O_5$ ESI Mass spectrum: m/z=350 [M+H]+

HPLC analytics: RT=3.08 min (HPLC method 5)

The following intermediates are prepared accordingly from the respective diaminobenzenes as indicated. Due to conditions applied, the syntheses may yield a free base, a TFA salt or other salt forms which can be applied equally to the syntheses of example compounds described below.

| Example | Structure | Diaminobenzene applied | Synthesis comment |
|---|---|---|---|
| XXI.2 | 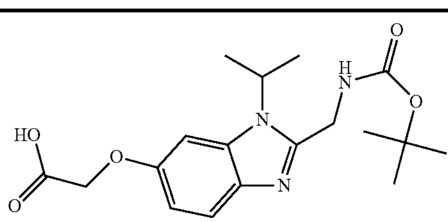 | V.7 | |

-continued

| Example | Structure | Diamino-benzene applied | Synthesis comment |
|---------|-----------|-------------------------|-------------------|
| XXI.3 | 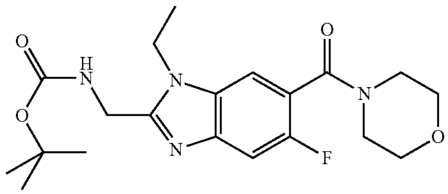 | V.10 | Product precipitates and is successively washed with\ water and diethyl ether, then dried at 50° C. |
| XXI.4 | 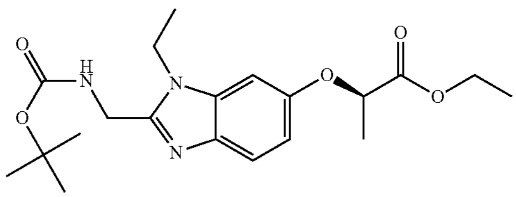 | V.11 | Product purified by silica gel chromatography (cyclohexane/ ethyl acetate 0% → 70%) |

Intermediate XXII.1

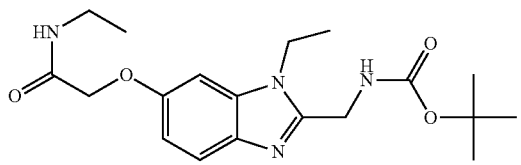

XXII.1

A mixture of the acid intermediate XXI.1 (200 mg; 0.52 mmol), TBTU (215 mg; 0.67 mmol) and N-methylmorpholine (177 mg; 1.75 mmol) in DMF (20 ml) is stirred at r.t. for 1 h. Ethylamine hydrochloride (46.2 mg; 0.57 mmol) is added. After stirring for 2 h the mixture is evaporated. The residue is taken up in ethyl acetate and washed with water and NaHCO$_3$ (sat. aq. solution). The organic layer is separated, dried and evaporated to yield the title compound as a crude product that ist further reacted without purification.

$C_{19}H_{28}N_4O_4$

The following intermediates are prepared accordingly from the respective amines and acids as indicated. Due to conditions applied, the syntheses may yield a free base, a TFA salt or other salt forms which can be applied equally to the syntheses of example compounds described below.

| Example | Structure | Amine applied | Acid applied | Synthesis comment |
|---------|-----------|---------------|--------------|-------------------|
| XXII.2 | 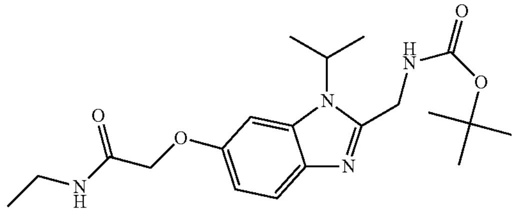 | ClH H$_2$N— | XXI.2 | |
| XXII.3 | 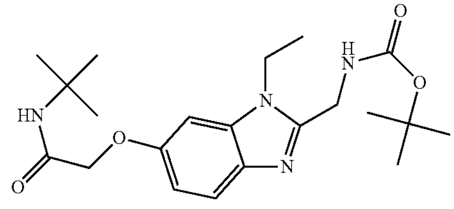 | H$_2$N— | XXI.1 | |
| XXII.4 | 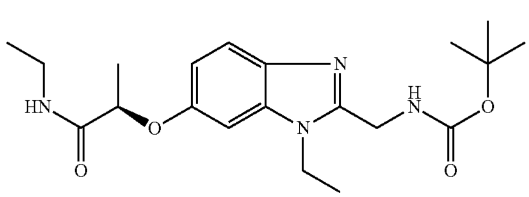 | ClH H$_2$N— | XXVII.1 | |

-continued

| Example | Structure | Amine applied | Acid applied | Synthesis comment |
|---------|-----------|---------------|--------------|-------------------|
| XXII.5 | 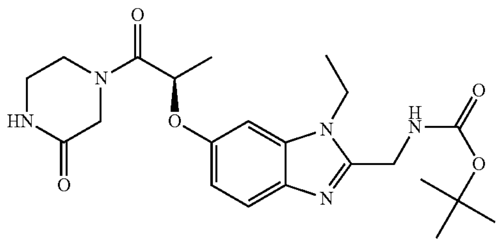 | XXVII.1 | | |
| XXII.6 | 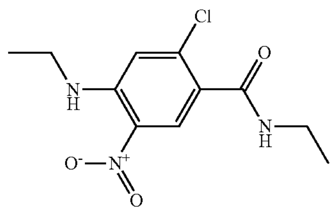 | Ethylamine (2M in THF) | IV.10 | HATU applied as coupling reagent |

Intermediate XXIII.1

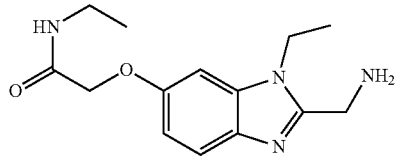

XXIII.1

A mixture of Intermediate XXII.1 (210 mg; 0.50 mmol) and TFA (193 µl; 2.51 mmol) in DCM is stirred at r.t. until TLC indicates complete conversion. The solvent is evaporated. The residue is taken up in methanol and purified by cation exchange chromatography (SCX cartridge; elution with methanolic ammonia).

$C_{19}H_{28}N_4O_4$

The following intermediates are prepared accordingly from the respective protected amine as indicated. Due to conditions applied, the syntheses may yield a free base, a TFA salt or other salt forms which can be applied equally to the syntheses of example compounds described bell) low.

| Example | Structure | protected starting material applied | Synthesis comment |
|---------|-----------|-------------------------------------|-------------------|
| XXIII.2 | 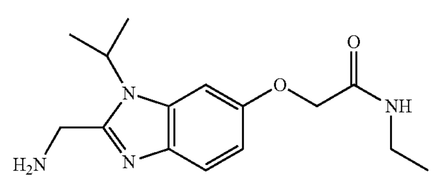 | XXII.2 | HCl/dioxane instead of TFA/DCM |
| XXIII.3 | 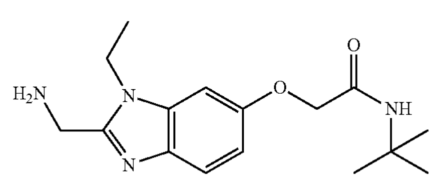 | XXII.3 | HCl/dioxane instead of TFA/DCM |
| XXIII.4 | 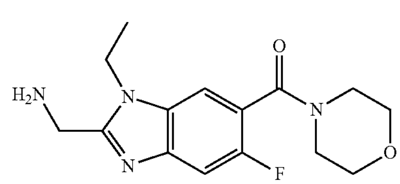 | XXI.3 | Footnote a |

| Example | Structure | protected starting material applied | Synthesis comment |
|---|---|---|---|
| XXIII.5 | ![structure] | XXII.4 | |
| XXIII.6 | ![structure] | XXII.5 | HCl/dioxane instead of TFA/DCM |
| XXIII.7 | ![structure] | XXIV.12 | Reaction 5h at 70° C.; no chromatographic purification | a HCl/dioxane instead of TFA/DCM; product precipitates upon dilution with diethyl ether.

Intermediate XXIV.1

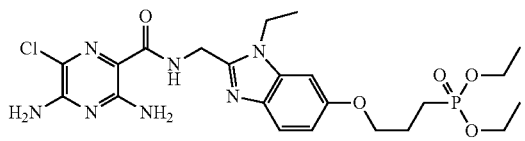

XXIV.1

A mixture of Intermediate X.7 (2.75 g; 7.44 mmol), Intermediate A.1 (1.40 g; 7.44 mmol), HATU (2.92 g; 7.44 mmol) and TEA (2.09 ml; 14.9 mmol) in DMF (15 ml) is stirred at r.t. over night. The mixture is poured on ice water and the resulting precipitate is filtered off, washed with water and dried.

$C_{22}H_{31}ClN_7O_5P$ ESI Mass spectrum: m/z=540 [M+H]+
HPLC analytics: RT=0.68 min (HPLC method 2)

The following intermediates of general formula XXIV.A are prepared accordingly from the respective amines as indicated. Due to conditions applied, the syntheses may yield a free base, a TFA salt or other salt forms which can be applied equally to the syntheses of example compounds described below.

XXIV.A

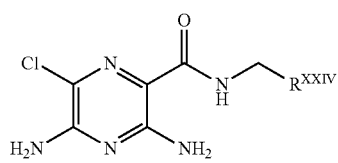

| Example | $R^{XXIV}$ | Amine applied | Synthesis comment |
|---|---|---|---|
| XXIV.2 | ![structure] | X.4 | |

XXIV.A

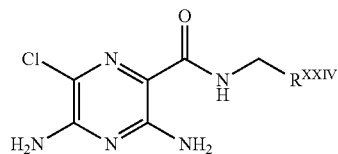

| Example | $R^{XXIV}$ | Amine applied | Synthesis comment |
| --- | --- | --- | --- |
| XXIV.3 | | X.9 | Mixture diluted with Na—HCO$_3$ (sat. aq. solution) to achive precipitation |
| XXIV.4 | | XXIII.1 | Purification by RP-HPLC (modifier: TFA) |
| XXIV.5 | | XXIII.2 | Purification by RP-HPLC (modifier: TFA) |
| XXIV.6 | | X.8 | Extraction with NaHCO$_3$ (sat. aq. solution/DCM; followed by RP-HPLC (column: SunFire C18; water-ACN; modifier TFA) |
| XXIV.7 | | X.6 | Extraction with NaHCO$_3$ (sat. aq. solution/DCM; followed by RP-HPLC (column: SunFire C18; water-ACN; modifier TFA) |
| XXIV.8 | | XXIII.3 | Purification by trituration with 1. diethyl ether/ethanol/water and 2. ACN/water |
| XXIV.9 | | XXIII.5 | Purification by RP-HPLC (water/ACN; modifier: TFA) |

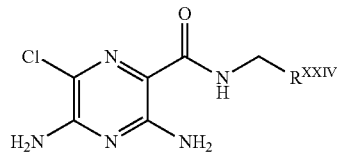

| Example | R<sup>XXIV</sup> | Amine applied | Synthesis comment |
|---|---|---|---|
| XXIV.10 | | X.5 | Purification by RP-HPLC (water/ACN; modifier: TFA) |
| XXIV.11 | | XXIII.6 | Purification by RP-HPLC (water/ACN; modifier: TFA) |
| XXIV.12 | | XXXVIII.2 | Purification by silica gel chromatography (DCM/methanol 98:2 → 96:4) |

Intermediate XXV.1

Intermediate XXVI.1

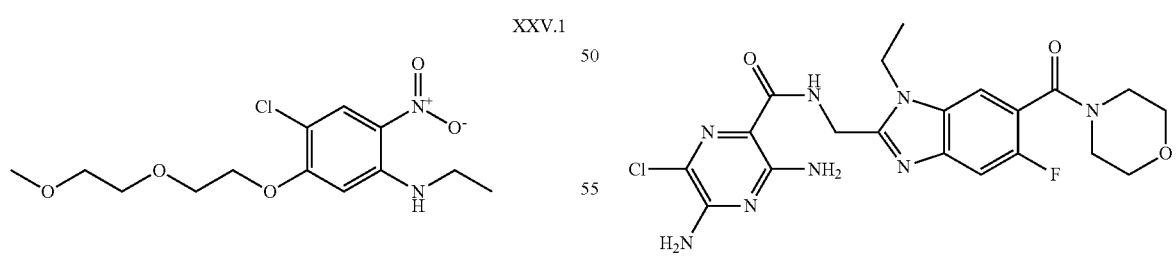

A mixture of intermediate IV.4 (1.00 g; 4.25 mmol), diethylene glycol monomethyl ether (520 mg; 4.33 mmol) and sodium hydride (55% in mineral oil; 204 mg; 4.68 mmol) in DMF (10 ml) is stirred at r.t. over night. Volatiles are evaporated and the residue is taken up in DCM and washed with water. The organic layer is separated, dried and evaporated. The residue is purified by silica gel chromatography (gradient: DCM/methanol 1-4%).

$C_{13}H_{19}ClN_2O_5$ ESI Mass spectrum: m/z=319 [M+H]+

To a mixture of intermediate XXIII.4 (200 mg; 0.583 mmol), intermediate B.1 (191 mg; 0.583 mmol), THF (5.0 ml) and DCM (3.0 ml) is added sodium hydroxide (1 M aqueous solution; 2.50 ml; 2.50 mmol). The mixture is stirred at r.t. for 18 h. The precipitate formed is filtered off, washed successively with a small volume of diethyl ether and then water and dried. The crude product is taken to the next reaction step without further purification.

$C_{20}H_{22}ClFN_8O_3$ ESI Mass spectrum: m/z=477 [M+H]+

Intermediate XXVII.1

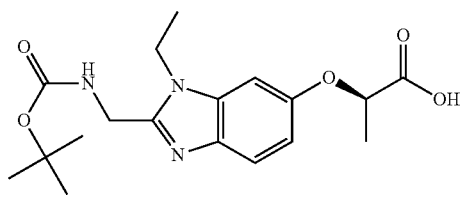

XXVII.1

A mixture of the ester intermediate XXI.4 (1.08 g; 2.57 mmol), sodium hydroxide (32% aqueous solution; 0.247 ml; 2.57 mmol), THF (10 ml), water (6 ml) and methanol (1 ml) is stirred at r.t. for two h. The mixture is acidified by addition of citric acid, diluted with water. The precipitate is filtered off, washed with water and dried.

$C_{18}H_{25}N_3O_5$ ESI Mass spectrum: m/z=364 [M+H]+

HPLC analytics: RT=3.33 min (HPLC method 5)

The following intermediates are prepared accordingly from the respective starting material as indicated. Due to conditions applied, the syntheses may yield a free acid, a hydrochloride or other salt forms which can be applied equally to the syntheses of example compounds described below.

| Example | Structure | starting mterial applied | Synthesis comment |
|---|---|---|---|
| XXVII.2 | 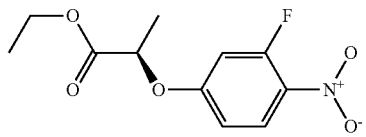 | XXII.6 | Reaction in 2N NaOH for 3 days at 90° C. Acidified with 4N HCl, extracted with DCM, evaporated. |

Intermediate XXVIII.1

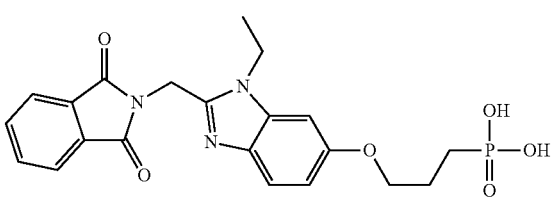

XXVIII.1

To a mixture of diisopropyl azodicarboxylate (689 µl; 3.50 mmol), triphenylphosphine (1.00 g; 3.82 mmol) and THF (10 ml), cooled to 0° C., are added 3-fluoro-4-nitrophenol (500 mg; 3.18 mmol) and (S)-ethyllactate (363 µl; 3.18 mmol). The mixture is stirred at r.t. for 2 h, then volatiles are removed. The crude product is purified by silica gel chromatography (cyclohexane/ethyl acetate 0%→20%).

$C_{11}H_{12}FNO_5$ Mass spectrum: m/z=257 [M]+

Intermediate XXIX.1

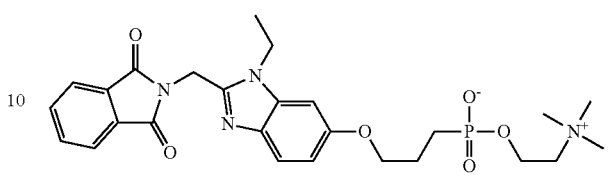

XXIX.1

A mixture of intermediate XXX.1 (1.84 g; 4.15 mmol), choline chloride (2.90 g; 20.7 mmol), EDC is (1.62 g; 8.30 mmol) and DMF (30 ml) is stirred at 50° C. for 3 days. Insolubles are filtered off and discarded, the filtrate is evaporated and purified by RP-HPLC (Sunfire; water/ACN, modifier: ammonia).

$C_{26}H_{35}N_4O_7P$ ESI Mass spectrum: m/z=529 [M+H]+

Intermediate XXX.1

XXX.1

A mixture of intermediate VI.3 (3.00 g; 6.01 mmol), bromotrimethylsilane (3.14 ml; 24.0 mmol), triethylamine (3.80 ml; 27.0 mmol) and THF (30 ml) is stirred at 50° C. over night. Insolubles are removed by filtration, the filtrate is evaporated and then taken up in warm ACN (20 ml). Water (10 ml) is added dropwise, the precipitate formed is filtered off with suction and dried at 50° C.

$C_{21}H_{22}N_3O_6P$ ESI Mass spectrum: m/z=442 [M-H]-

HPLC analytics: RT=0.59 min (HPLC method 2)

Intermediate XXXI.1

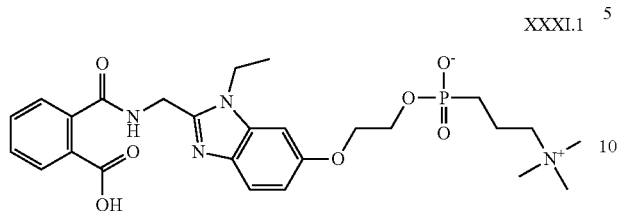

XXXI.1

A mixture of intermediate XXXII.1 (1.82 g; 3.60 mmol), lithium bromide (1.56 g; 18.0 mmol), trimethylamine (4.2 M in ethanol; 10.0 ml; 42.0 mmol) and methanol (20 ml) is stirred at 50° C. for 3 days. Water (20 ml) is added, insolubles are filtered off and discarded, and the filtrate is evaporated. The residue is purified by RP-HPLC (Sunfire; water/ACN, modifier: TFA) to yield the title compound.

$C_{26}H_{35}N_4O_7P$ ESI Mass spectrum: m/z=547 [M+H]+

Intermediate XXXII.1

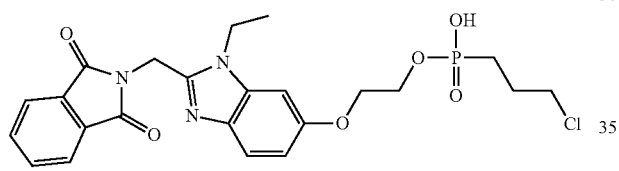

XXXII.1

A mixture of intermediate VI.4 (1.50 g; 4.11 mmol), 3-chloropropylphosphonic acid (0.651 g; 4.11 mmol), Dicyclohexyl carbodiimide (1.69 g; 8.21 mmol) and DMAP (50 mg; 0.411 mmol) in THF (20 ml) is stirred at 50° C. over night. Water is added and the mixture is stirred for further 20 min. The precipitate is filtered off and discarded, and the filtrate is evaporated to yield the crude title compound.

$C_{23}H_{25}ClN_3O_6P$ ESI Mass spectrum: m/z=506 [M+H]+

HPLC analytics: RT=0.54 min (HPLC method 10)

Intermediates XXXIII

| Intermediate | Structure | Synthesis described in: |
|---|---|---|
| XXXIII.1 | 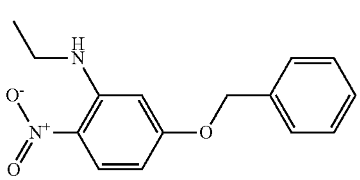 | US2012/149899 |

Intermediate XXXIV.1

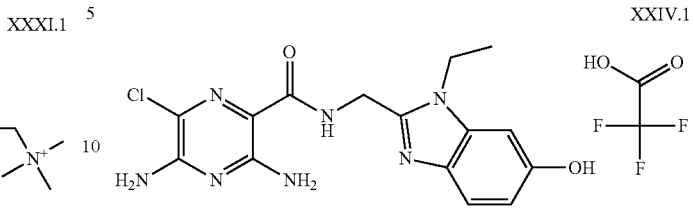

XXIV.1

To a solution of intermediate XXIV.3 (1.60 g; 4.26 mmol) in DCM (20 ml) is added boron tribromide (1 M in DCM; 21.3 ml; 21.3 mmol). The mixture is stirred ar r.t. over night, extracted with water. The aqueous phase is separated, evaporated to dryness. The residue is purified by RP-HPLC (Sunfire; water/ACN, modifier: TFA) to yield the title compound.

$C_{15}H_{16}ClN_7O_2$ ESI Mass spectrum: m/z=362 [M+H]+

Intermediate XXXIV.2

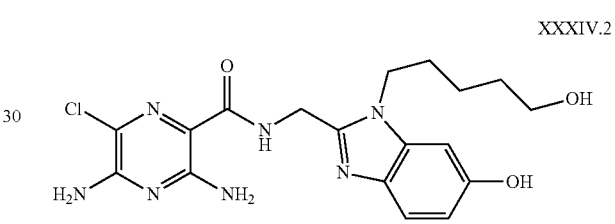

XXXIV.2

Intermediate XXXIV.2 is prepared from intermediate XXIV.2 according to the procedure described for intermediate XXXIV.1.

$C_{18}H_{22}ClN_7O_3$ ESI Mass spectrum: m/z=420 [M+H]+

HPLC analytics: RT=0.54 min (HPLC method 2)

Intermediate XXXV.1

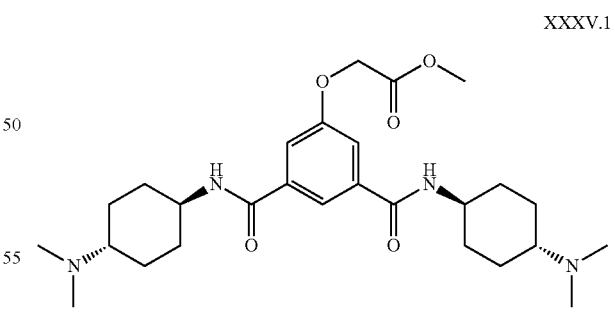

XXXV.1

A mixture of intermediate XXXVII.1 (3.30 g; 10.4 mmol), HATU (11.8 g; 31.2 mmol), triethylamine (10.0 ml; 72.1 mmol) and DMF (25 ml) is stirred for 45 min at r.t., then trans-N,N-dimethyl-1,4-diaminocyclohexane (4.43 g; 31.2 mmol) is added. The mixture is stirred for 45 min, then insolubles are filtered off, and the filtrate is evaporated to dryness. The crude intermediate is purified by RP-HPLC (column: SunFire C18; water-ACN; modifier TFA).

$C_{27}H_{42}N_4O_5$ ESI Mass spectrum: m/z=503 [M+H]+

Intermediate XXXVI.1

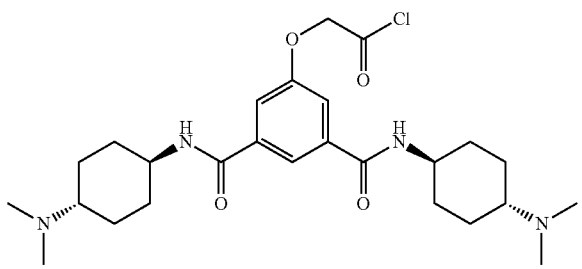

Stage 1

A mixture of intermediate XXXV.1 (1.20 g; 1.56 mmol) and NaOH (4M in water; 1.4 ml; 5.5 mmol) in methanol is stirred at 50° C. for 2 h. The mixture is neutralized by addition of aq. HCl, then evaporated to dryness. The residue is stirred in a mixture of DMF (10 ml), ACN (10 ml) and a small volume of water. The precipitate is filtered off and dried at 70° C.

Stage 2:

The product of stage 1 is stirred in thionyl chloride for 1 h at r.t. The mixture is evaporated to dryness, taken up in diethyl ether and evaporated to dryness again. The resulting acid chloride is further reacted without purification.

Intermediate XXXVII.1

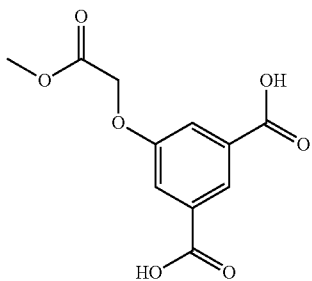

Stage 1:

A mixture of 5-hydroxy-isophthalic acid dimethyl ester (10.0 g; 47.6 mmol), bromoacetic acid tert-butyl ester (10.2 g; 52.3 mmol), potassium carbonate (7.23 g; 52.3 mmol) and acetone (200 ml) is stirred at 50° C. over night. Insolubles are filtered off and discarded. The filtrate is evaporated to dryness to yield the crude triester intermediate.

Stage 2:

To a mixture of intermediate from stage 1 (21.4 g) and methanol (150 ml) is added at 50° C. KOH (4 M aq. Solution; 165 m). The mixture is stirred at 70° C. for 16, then hydrochloric acid (4M aq. Solution; 165 ml) is added dropwise. The precipitate is filtered off with suction and dried at 70° C. to yield the crude triacid intermediate.

Stage 3:

A mixture of intermediate from stage 2 (10.0 g) and hydrochlorid acid (1.25 M in methanol; 125 ml) is stirred at r.t. for 1 h. Volatiles are evaporated and the residue is taken up in DMF (50 ml). The precipitate is filtered off and to the filtrate is added water. Further precipitate is again filtered off and the combined precipitates are dried at 70° C. to yield the title compound.

Intermediate XXXVIII.1

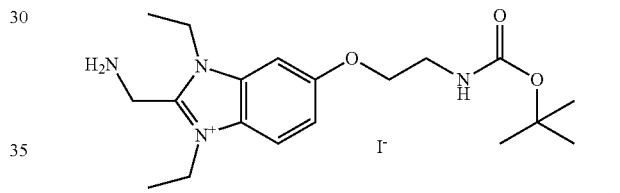

A mixture of intermediate XX.1 (8.20 g; 11.51 mmol) and piperidine (11.4 ml; 115 mmol) in THF (90 ml) is stirred at r.t. for 2 days. The precipitate is filtered off, washed with diethyl ether and dried.

$C_{19}H_{31}N_4O_3 \times I$ ESI Mass spectrum: m/z=363 [M+]

The following intermediate is prepared accordingly from the respective protected amine as indicated. Due to conditions applied, the syntheses may yield a free base, an iodide salt or other salt forms which can be applied equally to the syntheses of example compounds described below.

| Example | Structure | protected starting material applied | Synthesis comment |
|---|---|---|---|
| XXXVIII.2 | ![structure] | XX.3 | Purification by silica gel chromatography (DCM/methanol 8:2) |

7.2 Synthesis of Examples

Example 1.1

1.1

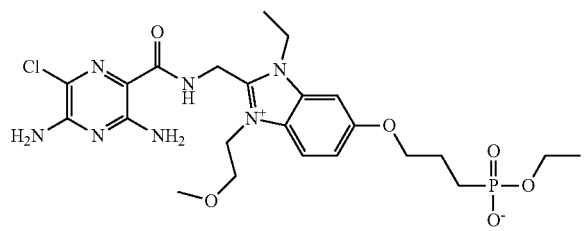

A mixture of 3,5-diamino-6-chloro-pyrazine-2-carboxylic acid (Intermediate A.1; 57 mg; 0.30 mmol), the amine intermediate X.1 (0.25 g; 0.31 mmol) the coupling reagent TBTU (0.106 g; 0.33 mmol) and TEA (126 µl; 0.90 mmol) in DMF (2.0 ml) is stirred at r.t. over night. Further 3,5-diamino-6-chloro-pyrazine-2-carboxylic acid (Intermediate A.1; 57 mg; 0.30 mmol), TBTU (0.106 g; 0.33 mmol) and TEA (126 µl; 0.90 mmol) in DMF (2.0 ml—all components premixed for 15 min) is added and the mixture is stirred at r.t. for further 2 h. The mixture is purified by RP-HPLC (column: SunFire C18; water-ACN; modifier TFA) to yield the title compound.

$C_{23}H_{33}ClN_7O_6P \times 2TFA$ ESI Mass spectrum: m/z=570 $[M+H]^+$

HPLC analytics: RT=0.68 min (HPLC method 2).

The following compounds of general formula 1.A are prepared accordingly applying the respective amine as indicated. Due to conditions applied, the procedures may yield a chloride salt, a TFA salt or bis-TFA salt, a zwitterion or other salt forms.

1.A

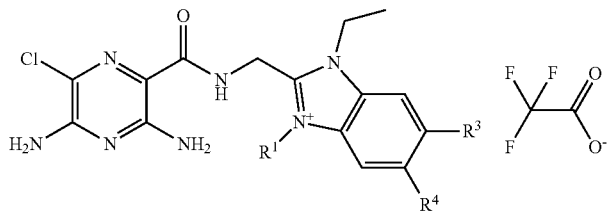

| Example | R¹ | R³ | R⁴ | Amine applied | Synthesis comment | ESI mass spectrum | HPLC retention time (min) | HPLC method |
|---|---|---|---|---|---|---|---|---|
| 1.2 | * ⌐⌐ | * ⌐⌐—NH—C(=O)—O—CH(fluorenyl) | H | III.1 | | 625 (M)⁺ | 0.59 | 1 |
| 1.3 | * ⌐⌐ | * —N(CH₂CH₂OH)₂ | Cl | III.2 | See footnote a, b | 511 (M)⁺ | 0.60 | 2 |
| 1.4 | * ⌐⌐ | * —O—CH₂CH₂—NH—C(=O)—O—tBu | H | XXXVIII.1 | See footnote b, c | 533 (M)⁺ | 0.73 | 2 |
| 1.5 | * ⌐⌐ | * (isosorbide-OH) | Cl | X.2 | See footnote d | 552 (M)+ | 0.63 | 2 |

-continued

1.A

| Example | R¹ | R³ | R⁴ | Amine applied | Synthesis comment | ESI mass spectrum | HPLC retention time (min) | HPLC method |
|---|---|---|---|---|---|---|---|---|
| 1.6 | (ethyl branched) | O-P(=O)(O-)-O-CH₂CH₂-N⁺(CH₃)₃ | H | X.3 | | 597 (M)+ | 0.52 | 2 |
| 1.7 | (S)-HOCH(CH₃)CH₂- | H | O-CH₂CH₂-NH₂ | X.10 | See footnote e | 463 (M)+ | 0.48 | 3 |
| 1.8 | (S)-HOCH(CH₃)CH₂- | H | isosorbide-O- | X.11 | | 548 (M)+ | 0.43 | 11 | a use of DIPEA instead of TEA.
b The mixture is extracted with NaHCO₃ (sat. aq. solution) and DCM/MeOH. The organic layer is separated, dried and evaporated. The residue is purified by RP-HPLC (column: SunFire C18; water-ACN; modifier TFA).
c The residue is purified by silica gel chromatography (DCM/MeOH → 30/1).
d HATU used as coupling reagent instead of TBTU.
e Subsequent BOC-deprotection by stirring at r.t. for 1 h in CAN/Dioxane/HCl.

Example 2.1

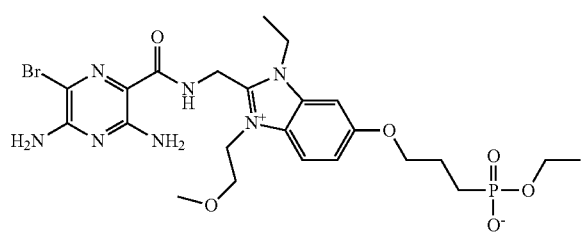

2.1

The 6-bromopyrazinecarboxamide derivative is prepared as described for example 1.1 starting from intermediate A.2 instead of A.1.

C₂₃H₃₃BrN₇O₆P ESI Mass spectrum: m/z=614 [M+H]⁺

HPLC analytics: RT=0.69 min (HPLC method 2)

Example 3.1

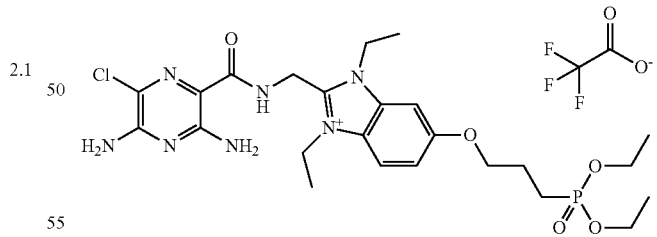

3.1

A mixture of Intermediate XXIV.1 (0.50 g; 0.93 mmol) and ethyl iodide (0.74 mL; 9.26 mmol) in ACN (10 ml) is stirred for 2 h at 120° C. (microwave heating, closed vessel). The mixture is purified by RP-HPLC (column: SunFire C18; water-ACN; modifier TFA) to yield the title compound.

C₂₄H₃₆ClN₇O₅P×TFA ESI Mass spectrum: m/z=568 [M+]
HPLC analytics: RT=0.71 min (HPLC method 2).

The following compounds of general formula 3.A are prepared accordingly using the respective alkyl halide benzimidazole as indicated. Due to conditions applied, the procedures may yield a chloride salt, a TFA salt or bis-TFA salt, a zwitterion or other salt forms.

3.A

Structure: Chloro-diamino-pyrazine-carboxamide linked via -NH-CH2- to a benzimidazolium (with R1, R2 on nitrogens, R3 and R4 on benzene ring), with trifluoroacetate counterion.

| Example | R¹ | R² | R³ | R⁴ | Alkyl halide applied | Benzi-midazole applied | Synthesis comment: see footnote(s) | ESI mass spectrum | HPLC retention time (min) | HPLC method |
|---|---|---|---|---|---|---|---|---|---|---|
| 3.2 | * (ethyl) | * (ethyl) | *-O-CH₂CH₂-O-CH₃ | Cl | EtI | XXIV.6 | a | 526 (M)⁺ | 0.71 | 2 |
| 3.3 | * (ethyl) | * (ethyl) | *-O-CH(CH₃)-C(O)-N(piperazinone) | H | EtI | XXIV.11 | d | 544 (M)⁺ | 3.23 | 8 |
| 3.4 | * (ethyl) | * (isopropyl) | *-O-CH₂-C(O)-NH-Et | H | EtI | XXIV.5 | d | 489 (M)⁺ | 3.42 | 5 |
| 3.5 | * (ethyl) | * (ethyl) | *-O-CH(CH₃)-C(O)-NH-Et | H | EtI | XXIV.9 | | 489 (M)⁺ | 3.41 | 5 |
| 3.6 | * (ethyl) | * (ethyl) | *-O-CH(CH₃)-C(O)-NH-Et | H | EtI | See footnote m | c | 489 (M)⁺ | 3.42 | 5 |
| 3.7 | * (ethyl) | —(CH₂)₄—OH | —OH | H | EtI | XXXIV.2 | | 448 (M)⁺ | 0.59 | 2 |
| 3.8 | CH₃— | * (ethyl) | *-O-CH₂CH₂-O-CH₃ | Cl | CH₃I | XXIV.6 | | 512 (M)⁺ | 0.73 | 4 |
| 3.9 | Me— | * (ethyl) | —OH | H | CH₃I | XXXIV.1 | | 376 (M)⁺ | 0.34 | 3 |
| 3.10 | * (ethyl) | * (ethyl) | —OH | H | EtI | XXXIV.1 | | 390 (M)⁺ | 0.37 | 3 |

-continued

3.A

| Example | R¹ | R² | R³ | R⁴ | Alkyl halide applied | Benzi-midazole applied | Synthesis comment: see footnote(s) | ESI mass spectrum | HPLC retention time (min) | HPLC method |
|---|---|---|---|---|---|---|---|---|---|---|
| 3.11 | * | * | (phosphocholine group) | H | I-ethyl | XXIV.10 | | 597 (M)⁺ | 0.60 | 2 |
| 3.12 | * | * | (morpholine carbonyl) | F | I-ethyl | XXVI.1 | e | 505 (M)⁺ | 0.63 | 9 |
| 3.13 | methoxyethyl | * | (diethyl phosphonate propyl ether) | H | Br-ethoxyethyl | XXVI.1 | f | 598 (M)⁺ | 0.71 | 2 |
| 3.14 | * | * | (ethylamino acetoxy) | H | Br-ethyl | XXIV.4 | g | 475 (M)⁺ | 3.32 | 5 |
| 3.15 | * | * | (isosorbide ether) | H | I-ethyl | XXIV.7 | h | 518 (M)⁺ | 0.36 | 3 |
| 3.16 | * | * | (tert-butylamino acetoxy) | H | I-ethyl | XXIV.8 | b | 475 (M)⁺ | 3.32 | 5 | a Reaction time: 5 days at 130° C.
b Additional solvent DMF. Purification by HPLC (modifier: NH₄COOH). Counterion expected to be formate.
c synthesis of example 3.6 as described for the optical antipode example 3.5 but starting from (R)-ethyllactate.
d Purification by HPLC (modifier: HCOOH). Counterion expected to be formate.
e Purification by HPLC (modifier: NH₄COOH). Counterion expected to be formate.
f Reaction time: 5h at 120° C.
g Purification by RP-HPLC (modifier: NH₃). Counterion expected to be iodide.
h Reaction time: 1 day at 130° C. The mixture is further purified by a preparative TLC.

Example 4.1

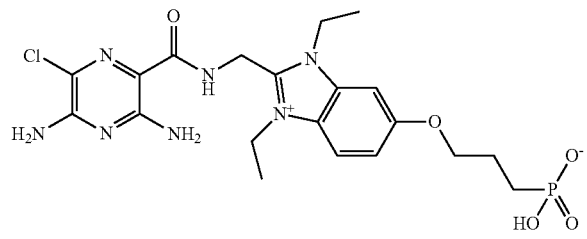

A mixture of Example 3.1 (60.0 mg; 0.09 mmol) and bromotrimethylsilane (0.15 ml; 1.15 mmol) in DMF (2 ml) is stirred at r.t. for 2 h. The mixture is purified by RP-HPLC (column: SunFire C18; water-ACN; modifier TFA) to yield the title compound.

$C_{20}H_{27}ClN_7O_5P$ ESI Mass spectrum: m/z=512 [M+H]$^+$
HPLC analytics: RT=0.32 min (HPLC method 7)

Example 5.1

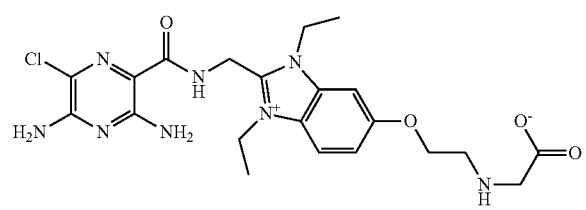

A mixture of example 9.1 (50.0 mg; 0.08 mmol) and NaOH (aq. solution; 1M; 230 µl; 0.24 mmol) in MeOH (2 ml) is stirred at r.t. over night. The mixture is neutralised with HCl (aq. solution; 1 M; 230 µl; 0.24 mmol) and evaporated. The residue is stirred in DCM and a small volume of MeOH. Insolubles are filtered off and discarded. The mother liquor is evaporated to yield the title compound.

$C_{21}H_{27}ClN_8O_4$ ESI Mass Spectrum: m/z=491 [m+h]$^+$
HPLC analytics: RT=0.52 min (HPLC method 2).

Example 5.2

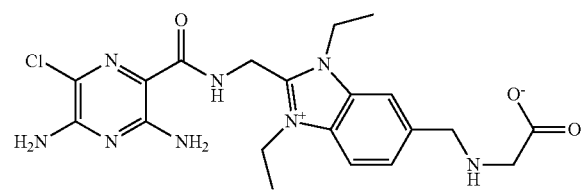

Stage 1:
A mixture of example 6.1 (100 mg; 0.11 mmol), bromo-acetic acid tert-butyl ester (15.8 µl; 0.11 mmol) and TEA (67.0 µl; 0.48 mmol) in DMF (5 ml) is stirred at r.t. for 15 min. Additional bromo-acetic acid tert-butyl ester (1 eq) and TEA (60 µl) is added. After stirring for 2 h additional bromo-acetic acid tert-butyl ester (2 eq) is added. After 2 h of stirring the mixture is purified by RP-HPLC (column: SunFire C18; water-ACN; modifier TFA) to yield the tert-butyl ester of the title compound.

$C_{24}H_{34}ClN_8O_3 \times C_2F_3O_2$ ESI Mass spectrum: m/z=517 [M]$^+$

Stage 2:
A mixture of the intermediate from stage 1 (40.0 mg; 0.06 mmol) and TFA (25% in DCM; 2 ml) is stirred at r.t. over night. The product is purified by RP-HPLC (column: SunFire C18; water-ACN; modifier TFA) to yield the title compound.

$C_{20}H_{25}ClN_8O_3$ ESI Mass spectrum: m/z=461 [M+H]$^+$
HPLC analytics: RT=0.34 min (HPLC method 1).

Example 6.1

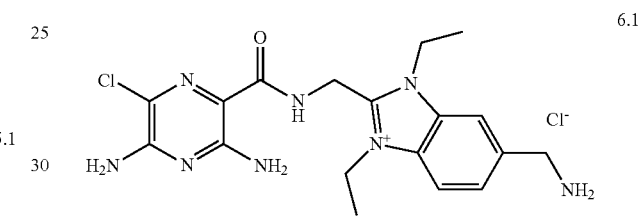

A mixture of example 1.2 (80.0 mg; 0.11 mmol) and piperidine (113 µl; 1.15 mmol) in THF (5 ml) is stirred at r.t. over night. The mixture is purified by RP-HPLC (column: SunFire C18; water-ACN; modifier TFA). The product is taken up in HCl/ethyl acetate and the solvent is evaporated to yield the title compound.

$C_{11}H_{24}ClN_8O \times Cl$ ESI Mass spectrum: m/z=403 [M]$^+$
HPLC analytics: RT=0.48 min (HPLC method 2).

Example 6.2

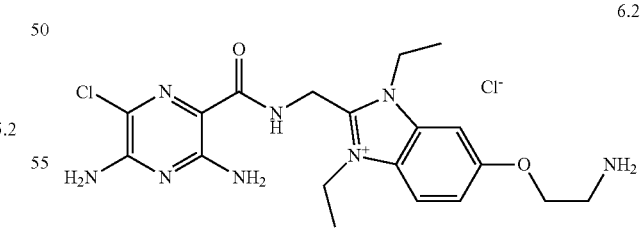

A mixture of example 1.4 (1.20 g; 1.82 mmol) and TFA (20% in DCM; 20 ml) is stirred at r.t. for 1 h. The mixture is purified by RP-HPLC (column: SunFire C18; water-ACN; modifier TFA). The product is taken up in HCl/MeOH and the solvent is evaporated to yield the title compound.

$C_{19}H_{26}ClN_8O_2 \times Cl$ ESI Mass spectrum: m/z=433 [M]$^+$
HPLC analytics: RT=0.51 min (HPLC method 2).

Example 6.3

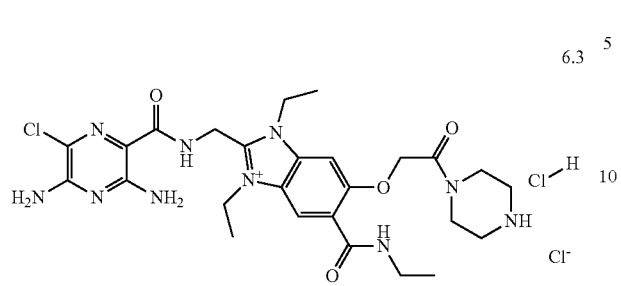

A mixture of example 7.4 (90 mg; 0.112 mmol) and HCl (4M in dioxane; 0.5 ml) is stirred at r.t. over night. The mixture is evaporated, taken up in HCl/methanol and evaporated again to yield the title compound.

$C_{26}H_{36}ClN_{10}O_4 \times Cl \times HCl$ ESI Mass spectrum: m/z=587 [M]$^+$ HPLC analytics: RT=0.67 min (HPLC method 2)

Example 7.1

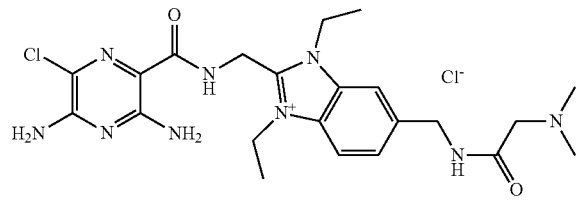

A mixture of the amine example 6.1 (100 mg; 0.11 mmol), the coupling reagent TBTU (69.0 mg; 0.21 mmol) and TEA (74.7 µl; 0.54 mmol) in ACN (3 ml) is stirred at r.t. for 10 min. The acid N,N-dimethyl glycine (27.7 mg; 0.27 mmol) in ACN (2 ml) is added and the mixture is stirred over night. Insolubles are filtered off and discarded. The evaporated filtrate is purified by RP-HPLC (column: SunFire C18; water-MeOH; modifier TFA). The product is taken up in HCl/ethyl acetate and the solvent is evaporated to yield the title compound.

$C_{22}H_{31}ClN_9O_2 \times Cl$ ESI Mass spectrum: m/z=488 [M+H]$^+$
HPLC analytics: RT=0.33 min (HPLC method 1).

The following compounds of general formula 7.A are prepared accordingly using the respective amines and acids as indicated. Due to conditions applied, the procedures may yield a free base, a hydrochloride or dihydrochloride salt, a TFA salt or bis-TFA salt, a zwitterion or other salt forms.

7.A

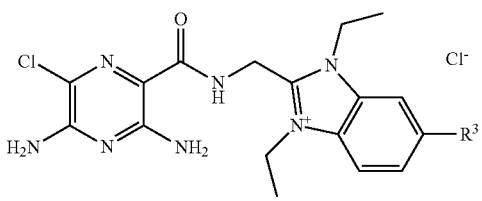

| Example | R$^3$ | R$^4$ | Amine applied | Acid applied | Synthesis comment | ESI mass spectrum | HPLC retention time (min) | HPLC method |
|---|---|---|---|---|---|---|---|---|
| 7.2 | ![structure] | H | 6.2 | ![structure] | Coupling reagent: HATU | 873 (M)$^+$ | 0.33 | 1 |
| 7.3 | ![structure] | * | N—Methyl—piperazine | XXIII.7 | Coupling reagent: HATU | 601 (M)$^+$ | 0.68 | 2 |
| 7.4 | ![structure] | * | N—BOC—piperazine | XXIII.7 | Coupling reagent: HATU | 687 (M)$^+$ | 0.88 | 2 |

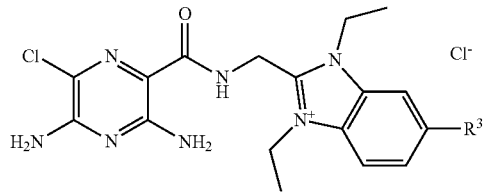

| Example | R[3] | R[4] | Amine applied | Acid applied | Synthesis comment | ESI mass spectrum | HPLC retention time (min) | HPLC method |
|---|---|---|---|---|---|---|---|---|
| 7.5 | (structure) | * | Ethylamine | XXIII.7 | Coupling reagent: HATU; solvent: DMF | 546 (M)+ | 0.76 | 2 |

Example 8.1

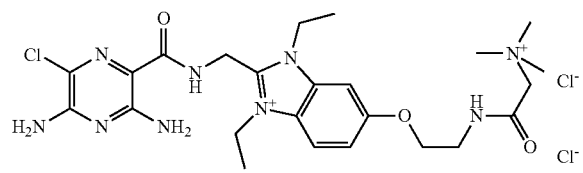

A mixture of example 7.2 (50.0 mg; 0.07 mmol), methyl iodide (41.0 µl; 0.66 mmol) and potassium carbonate (22.7 mg; 0.16 mmol) in ACN (3 ml) is stirred in a sealed flask for 30 min at 50° C. Insolubles are filtered off and discarded. The mother liquor is purified by RP-HPLC (column: SunFire C18; water-ACN; modifier TFA). The product is taken up in HCl/MeOH and the solvent is evaporated to yield the title compound.

$C_{24}H_{36}ClN_9O_3 \times 2Cl$ ESI Mass spectrum: m/z=266 $[M]^{2+}$

HPLC analytics: RT=0.55 min (HPLC method 2)

The following compounds of general formula 8.A are prepared accordingly using the respective amine as indicated. Due to conditions applied, the procedures may yield a chloride salt, a TFA salt or bis-TFA salt, a zwitterion or other salt forms.

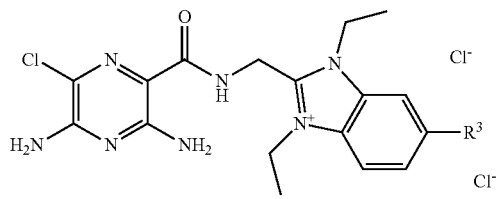

| Example | R[3] | Amine applied | Synthesis comment | ESI mass spectrum | HPLC retention time (min) | HPLC method |
|---|---|---|---|---|---|---|
| 8.2 | (structure) | 7.1 | | 502 (M − H)+ | 0.53 | 2 |
| 8.3 | (structure) | 6.1 | | | 0.49 | 1 |
| 8.4 | (structure) | 6.2 | | 238 (M)++ | 0.53 | 2 |

Example 9.1

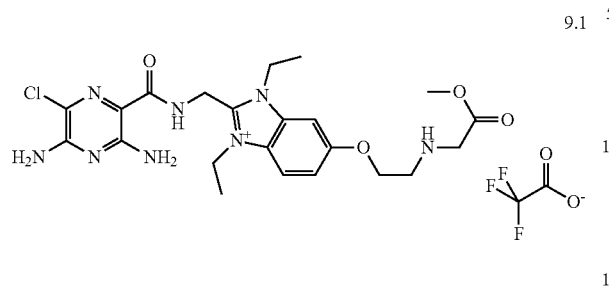

Example 10.1

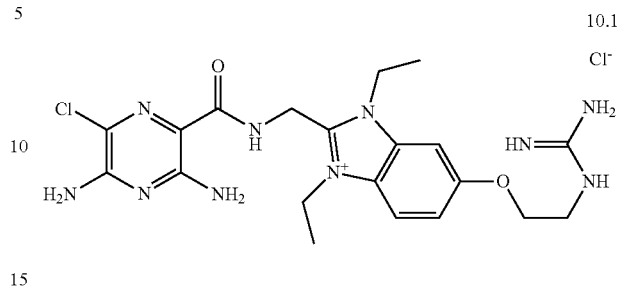

A mixture of example 6.2 (250.0 mg; 0.42 mmol), methyl bromoacetate (40.9 µl; 0.42 mmol) and potassium carbonate (144.6 mg; 1.05 mmol) in DMF (5 mL) is stirred at r.t. for 5 h. Insolubles are filtered off and discarded. The mother liquor is purified by RP-HPLC (column: SunFire C18; water-ACN; modifier TFA) to yield the title compound.

$C_{22}H_{30}ClN_8O_4 \times C_2F_3O_2$ ESI Mass spectrum: m/z=505 $[M]^+$

HPLC analytics: RT=0.52 min (HPLC method 2).

A mixture of example 6.2 (60.0 mg; 0.10 mmol), 1H-1,2,4-triazole-1-carboxamidine hydrochloride (15.3 mg; 0.10 mmol) and TEA (45.8 µl; 0.33 mmol) in DCM (5 ml) is stirred at r.t. over night. The mixture is purified by RP-HPLC (column: SunFire C18; water-ACN; modifier TFA). The residue is taken up in HCl/MeOH and the solvent is evaporated to yield the title compound.

$C_{20}H_{28}ClN_{10}O_2 \times Cl$ ESI Mass spectrum: m/z=475 $[M]^+$

HPLC analytics: RT=0.54 min (HPLC method 2).

Example 11.1

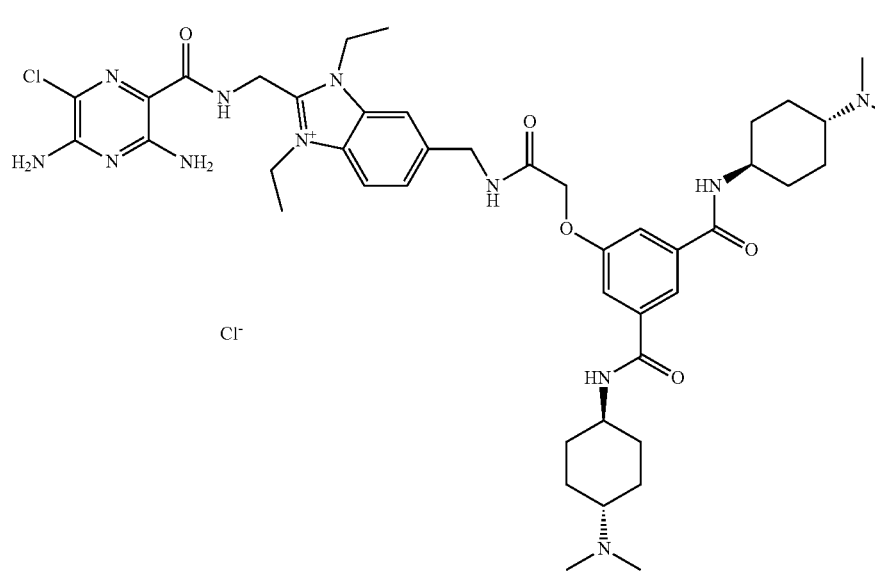

To an ice-cold solution of intermediate XXXVI.1 (52 mg; 0.103 mmol) in DCM (20 ml) is added dropwise a solution of example 6.1 and triethylamine (71 µl; 0.513 mmol) in ACN/THF 1:1 (6 ml). The mixture is stirred over night without further cooling, then evaporated to dryness. The residue is purified by RP-HPLC (column: SunFire C18; water-ACN; modifier TFA). The residue is taken up in HCl/MeOH and the solvent is evaporated to yield the title compound.

$C_{44}H_{62}ClN_{12}O_5 \times Cl$ ESI Mass spectrum: m/z=873 $[M]^+$

HPLC analytics: RT=0.33 min (HPLC method 1).

8. ANALYTICAL METHODS AND PREPARATIVE CHROMATOGRAPHY

As a rule, $^1$H-NMR and mass spectra have been obtained for the compounds prepared. Mass peaks given (e.g. (M+H)+, (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel from Millipore (MATREX™, 35-70 my) is used.

Preparative Thin Layer Chromatography (TLC):

Preparative TLC plates from Merck (PLC Silica gel 60 $F_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to yield the purified compound.

Preparative HPLC:

Stationary phase: XBridge C18; 10 μm or SunFire C18; 10 μm (both from waters, www.waters.com).

Analytical HPLC/MS Methods

The HPLC retention times given are measured under the following parameters.

HPLC Method 1

| Column: SunFire C18, 2.1 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

HPLC Method 2

| Column: SunFire, 3 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method 3

| Column: XBridge BEH C18, 2.1 × 30 mm, 1.7 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

HPLC Method 4

| Column: SunFire C18, 4.6 × 30 mm, 3.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 98 | 2 | 2.5 | 60 |
| 1.50 | 0 | 100 | 2.5 | 60 |
| 1.80 | 0 | 100 | 2.5 | 60 |

HPLC Method 5

| Column: | Atlantis dC18 5 μm 4.6 × 50 mm, Temp 35° C. |
|---|---|
| Mobile phase: | A = H2O 90% + 10% CH3CN + CF3COOH 0.05% |
| | B = CH3CN 90% + 10% H2O |

| Time in min | % A | % B | flow rate in ml/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

HPLC Method 6

| Column: SunFire C18, 4.6 × 30 mm, 3.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 98 | 2 | 2.5 | 60 |
| 1.50 | 0 | 100 | 2.5 | 60 |
| 1.80 | 0 | 100 | 2.5 | 60 |

HPLC Method 7

| Column: SunFire C18, 2.1 × 50 mm, 2.5 μm (Waters) | | | | |
|---|---|---|---|---|
| Gradient time [min] | % Sol [H2O, 0.1% TFA] | % Sol [ACN, 0.08% TFA] | Flow [ml/min] | Temp [° C.] |
| 0.00 | 95 | 5 | 1.5 | 60 |
| 0.75 | 0 | 100 | 1.5 | 60 |
| 0.85 | 0 | 100 | 1.5 | 60 |

HPLC Method 8

| Column: | Synergi Hydro RP100A, 2.5 μm, 3 × 50 mm |
|---|---|
| Mobile phase: | A = H2O 90% + 10% CH3CN + NH4COOH 5 mM |
| | B = CH3CN 90% + H2O 10% |

| Time in min: | % A | % B | Flow rate in mL/min |
|---|---|---|---|
| 0.00 | 100 | 0 | 1.2 |
| 4.00 | 0 | 100 | 1.2 |
| 5.30 | 0 | 100 | 1.2 |
| 5.50 | 100 | 0 | 1.2 |
| 6.00 | 100 | 0 | 1.2 |

HPLC Method 9

| Column: | BEH C18 1.7 μm 2.1 × 50 mm, Temp 35° C. | | |
|---|---|---|---|
| Mobile phase: | A = H2O 90% + CH3CN 10% + NH4COOH 5 mM | | |
| | B = CH3CN 90% + H2O 10% | | |

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

HPLC Method 10

| Column: XBridge C18, 3 × 30 mm, 2.5 μm (Waters) | | | | |
|---|---|---|---|---|
| Gradient/Solvent Time [min] | % Sol [H2O, 0.1% NH3] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method 11

| Column: Sunfire C18_3.0 × 30 mm, 2.5 μm (Waters) | | | | |
|---|---|---|---|---|
| Gradient/Solvent Time [min] | % Sol [H2O 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

The following abbreviations are used above and hereinafter:
ACN Acetonitrile
BOC tert-Butoxycarbonyl
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
Eq. Molar equivalent
ESI Electrospray ionization
h hour
HATU O-(7-Azabenzotriazol-1-yl)-N,N,N',N'-tetramethyluronium hexafluorophosphate
HCl Hydrochloric acid
KOH Potassium hydroxide
l litre
LiHMDS Lithium bis(trimethylsilyl)amide
M mol/l
Min minutes
Mp melting point
NaOH Sodium hydroxide
n.d. not determined
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluronium-tetrafluoroborate
TEA Triethylamine
TFA Trifluoroacetic acid
THF Tetrahydrofurane
TLC Thin Layer Chromatography
TMS Trimethylsilyl

arrow and asterisk indicate the binding site, i.e. the point of attachment (here: atom "A") within a chemical entity (here exemplified by the group "A-R")

9. PHARMACOLOGICAL TEST METHOD

Ussing Chamber:

Mouse kidney M-1 cells were cultivated in DMEM containing 5% FCS and 5 μM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package LabView for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as $IC_{50}$.

With the example compounds given above, the following $IC_{50}$ values were determined in the Ussing Chamber assay:

| Example | 1.1 | 1.2 | 1.3 | 1.4 | 1.5 | 1.6 | 1.7 | 1.8 | 2.1 | 3.1 | 3.2 | 3.3 |
|---|---|---|---|---|---|---|---|---|---|---|---|---|
| $IC_{50}$ [nM] | 11 | 9 | 2 | 0.4 | 1 | 3 | 2 | 1 | 16 | 3 | 0.5 | 1 |
| Example | 3.4 | 3.5 | 3.6 | 3.7 | 3.8 | 3.9 | 3.10 | 3.11 | 3.12 | 3.13 | 3.14 | 3.15 |
| $IC_{50}$ [nM] | 1 | 0.5 | 1 | 1 | 0.4 | 1 | 0.2 | 3 | 0.4 | 2 | 0.3 | 3 |
| Example | 3.16 | 4.1 | 5.1 | 5.2 | 6.1 | 6.2 | 6.3 | 7.1 | 7.2 | 7.3 | 7.4 | 7.5 |
| $IC_{50}$ [nM] | 0.4 | 11 | 5 | 1 | 1 | 1 | 4 | 2 | 2 | 7 | 14 | 13 |
| Example | 8.1 | 8.2 | 8.3 | 8.4 | 9.1 | 10.1 | 11.1 | | | | | |
| $IC_{50}$ [nM] | 0.4 | 5 | 2 | 1 | 2 | 0.3 | 2 | | | | | |

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-toapical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2 \times 10^5$ cells/1 cm$^2$ area) are seeded on filter inserts (Costar transwell polycarbonate filters, 0.4 μm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KC, 1 mM MgSO4, 1.8 mM CaCl2, 4.17 mM NaHCO3, 1.19 mM Na2HPO4×7H2O, 0.41 mM NaH2PO4×H2O, 15 mM HEPES, 20 mM glucose, 0.25% BSA, pH 7.4) to prepare the transport solutions (10 μM compound, final DMSO<=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenished by HTP-4 buffer. The compound concentration in the samples is measured by HPLC-MS/MS or scintillation counting. The permeability coefficient (Papp) and efflux ratio are calculated according to:

Papp [cm/s]=(concentration receiver [nM]*volume receiver [mL]/time interval [sec])*(1/filter area)*(1/donor concentration [nM])

With example compounds given above, the following permeability values were determined in the CALU-3 cells assay:

| Example | 1.1 | 1.5 | 1.7 | 2.1 | 3.5 | 3.7 | 3.8 | 3.12 | 7.1 |
|---|---|---|---|---|---|---|---|---|---|
| Papp, AB [$10^{-6}$ cm/s] | 0.1 | 0.3 | 0.03 | 0.2 | 1 | 0.7 | 0.2 | 0.1 | <0.9 |
| Papp, BA [$10^{-6}$ cm/s] | 0.03 | 0.1 | 0.05 | 0.08 | 0.4 | 0.3 | 0.2 | 0.2 | 0.2 |

10. INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmacologically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation 1 capsule contains:

| | |
|---|---|
| active substance | 0.5 mg |
| lactose for inhalation | 5.0 mg |
| | 5.5 mg |

Preparation:

The active substance is mixed with lactose for inhalation. The mixture is packed into capsules in a capsule-making machine (weight of the empty capsule approx. 50 mg).

weight of capsule: 55.5 mg

The invention claimed is:

1. A compound of formula (I),

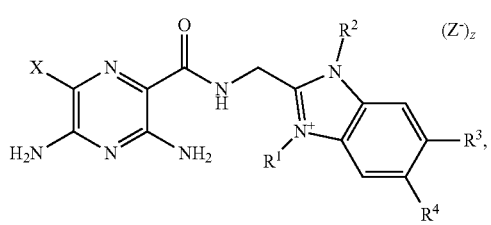

characterized in that
X denotes Cl or Br,
$R^1$ and $R^2$ denote independently $C_{1-4}$-alkyl-, $CH_3$—O—$C_{2-4}$-alkylene-, HO—$(CH_2)_n$—O—$C_{2-3}$-alkylene- or HO—$C_{2-6}$-alkylene-,
$R^3$ denotes (HO—$C_{2-3}$-alkylene)$_2$N—, $(R^5O—)(R^6O—)$P(O)—$(CH_2)_n$—O—, (HO—)$((CH_3)_3N^+—(CH_2)_n—)$P(O)—O—$(CH_2)_n$—O—, $(R^5O—)(C_{1-3}$-alkyl-)P(O)—O—$(CH_2)_n$—O—, $R^7R^8N$—C(O)—$C_{1-2}$-alkylene-O—, $R^9R^{10}N$—$(CH_2)_n$—O—, $(CH_3)_3N^+$—$(CH_2)_n$—O—, $R^9R^{11}N$—$(CH_2)_n$—O—, $CH_3$—(O—$CH_2$—$CH_2)_m$—O—, H—(O—$CH_2$—$CH_2)_m$—O—, $R^9R^{10}N$—$CH_2$—, $(CH_3)_3N^+$—$CH_2$—, 9-fluorenylmethyl-O—C(O)—$NR^9$—$CH_2$—, $R^9R^{10}N$—$CH_2$—C(O)—$NR^9$—$CH_2$—, $(CH_3)_3N^+$—$CH_2$—C(O)—$NR^9$—$CH_2$—, $R^9$—O—C(O)—$CH_2$—$NR^9$—$CH_2$—, $(R^9R^{10}N$-cyclohexyl-$NR^9$—C(O)-)$_2$phenyl-O—$CH_2$—C(O)—$NR^9$—$CH_2$—, tetrahydropyranyl-O— or
$R^3$ denotes a substituent selected from the group consisting of formula (cae)

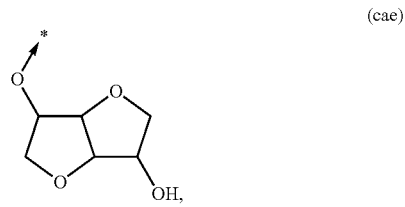

$R^4$ denotes H, halogen or $(C_{1-4}$-alkyl-)NH—C(O)—,
$R^5$ denotes H or $C_{1-3}$-alkyl-,
$R^6$ denotes H, $C_{1-3}$-alkyl-, $CH_3$—O—$(CH_2)_n$—, tetrahydrofuryl-$CH_2$— or $(CH_3)_3N^+$—$(CH_2)_n$—,
$R^7$ and $R^8$ denote independently H, $C_{1-4}$-alkyl-, $(CH_3)_2P(O)$—$CH_2$—O—$(CH_2)_n$— or,
$R^7$ and $R^8$ together with the nitrogen atom they are attached to form a 5- or 6-membered heterocycle from the group consisting of pyrrolidine, morpholine, piperazine, piperazinone, N-methylpiperazine, N-methylpiperazinone, N—BOC-piperazine, thiomorpholine, thiomorpholine-S-oxide or thiomorpholine sulfone,
$R^9$ and $R^{10}$ denote independently H or methyl,
$R^{11}$ denotes $C_{1-4}$-alkyl-O—C(O)—, $NH_2$—C(NH)—, $R^9R^{10}N$—$CH_2$—C(O)—, $(CH_3)_3N^+$—$CH_2$—C(O)— or $R^9$—O—C(O)—$CH_2$—,
m denotes 1, 2 or 3,
n denotes 2 or 3,
$Z^-$ denotes a physiologically acceptable anion selected from the group consisting of chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate,
z denotes 0 for negatively charged substituents $R^1$-$R^4$, 1 for uncharged substituents $R^1$-$R^4$ or 2 for positively charged substituents $R^1$-$R^4$,
or a tautomer or pharmacologically acceptable acid addition salt thereof.

2. The compound of formula (I) according to claim 1, characterized in that $R^1$ and $R^2$ denote independently $C_{1-3}$-alkyl-, $CH_3$—O—$C_{2-3}$-alkylene- or HO—$C_{2-6}$-alkylene-.

3. The compound of formula (I) according to claim 1, characterized in that $R^1$ denotes $C_{1-3}$-alkyl- or $CH_3$—O—$C_{2-3}$-alkylene-.

4. The compound of formula (I) according to claim 1, characterized in that $R^2$ denotes $C_{1-3}$-alkyl- or HO—$C_{2-6}$-alkylene-.

5. The compound of formula (I) according to claim 1, characterized in that
$R^3$ denotes (HO—$C_{2-3}$-alkylene)$_2$N—, $(R^5O—)(R^6O—)$P(O)—$(CH_2)_n$—O—, (HO—)$((CH_3)_3N^+—(CH_2)_3—)$P(O)—O—$(CH_2)_n$—O—, $R^7R^8N$—C(O)—$C_{1-2}$-alkylene-O—, $R^9R^{10}N$—$(CH_2)_n$—O—, $(CH_3)_3N^+$—$(CH_2)_2$—O—, $R^9R^{11}N$—$(CH_2)_n$—O—, $CH_3$—(O—$CH_2$—$CH_2)_m$—O—, $R^9R^{10}N$—$CH_2$—, $(CH_3)_3N^+$—$CH_2$—, 9-fluorenylmethyl-O—C(O)—NH—$CH_2$—, $R^9R^{10}N$—$CH_2$—C(O)—NH—$CH_2$—, $(CH_3)_3N^+$—$CH_2$—C(O)—NH—$CH_2$—, $R^9$—O—C(O)—$CH_2$—NH—$CH_2$— or
$R^3$ denotes a substituent selected from the group consisting of formula (cae)-(caf)

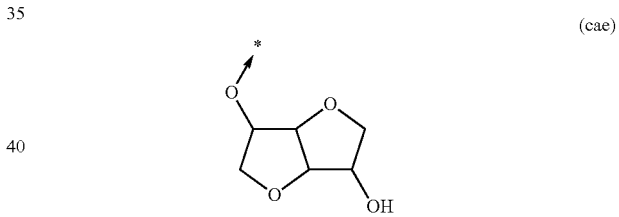

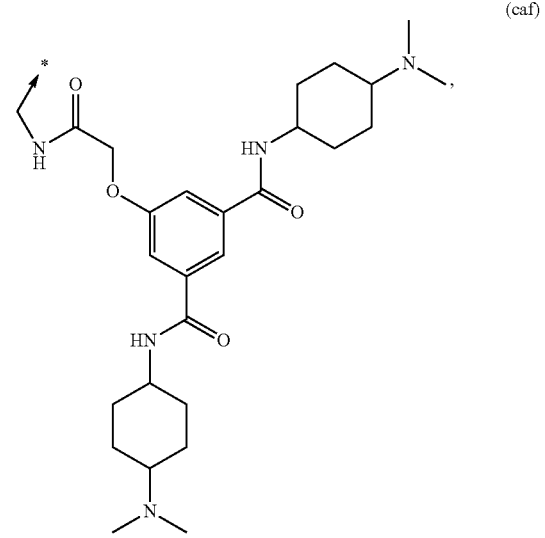

$R^5$ denotes H or $C_{1-3}$-alkyl-,
$R^6$ denotes H, $C_{1-3}$-alkyl- or $(CH_3)_3N^+$—$(CH_2)_n$—,
$R^7$, $R^8$ denote independently H, $C_{1-4}$-alkyl- or R⁷ and R⁸ together with the nitrogen atom they are attached to form a piperazinone, R⁹ and R¹⁰ denote independently H or methyl, R¹¹ denotes $C_{1-4}$-alkyl-O—C(O)—, NH₂—C(NH)—, R⁹R¹⁰N—CH₂—C(O)—, (CH₃)₃N⁺—CH₂—C(O)— or R⁹—O—C(O)—CH₂—, m denotes 1, 2 or 3, n denotes 2 or 3.

6. The compound of formula (I) according to claim 1, characterized in that R¹ denotes methyl-, ethyl- or a substituent of formula (aa)

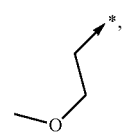
(aa)

R² denotes ethyl-, 2-propyl- or a substituent of formula (ba)

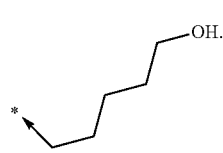
(ba)

7. The compound of formula (I) according to claim 1, characterized in that R³ denotes a substituent selected from the group consisting of formula (ca)-(cad)

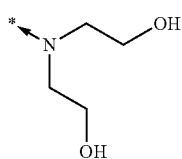
(ca)

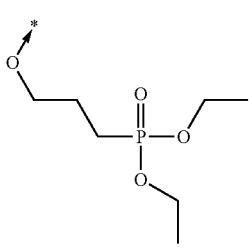
(cb)

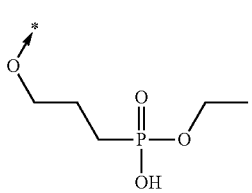
(cc)

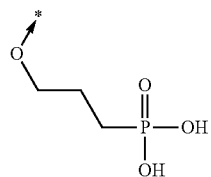
(cd)

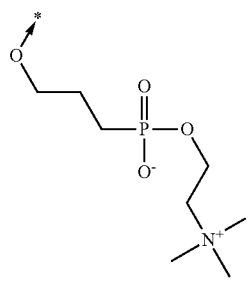
(ce)

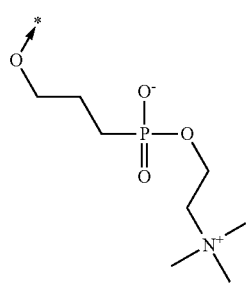
(cf)

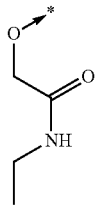
(cg)

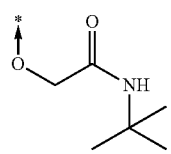
(ch)

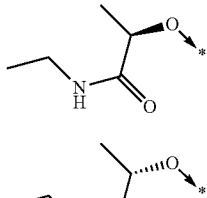
(ci)

(cj)

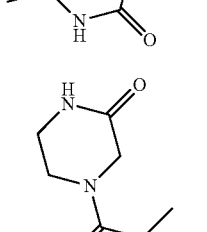
(ck)

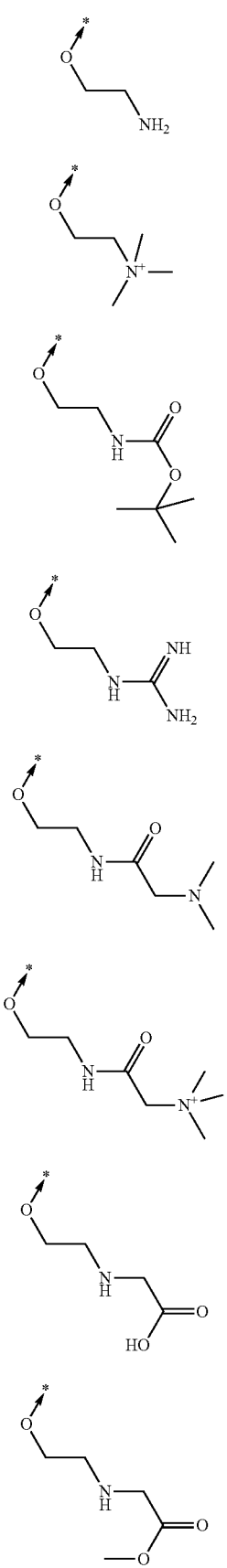
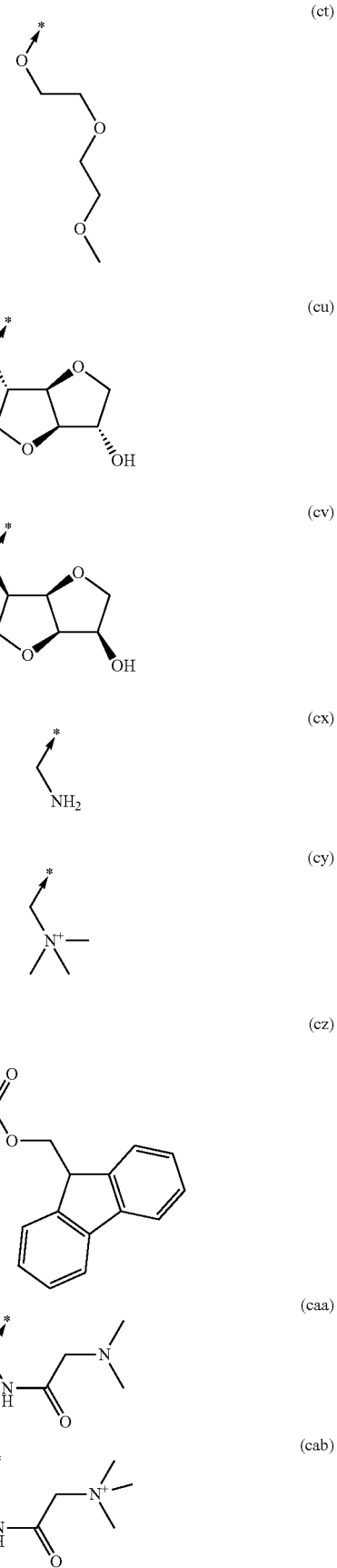

(cac)

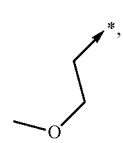

(cad)

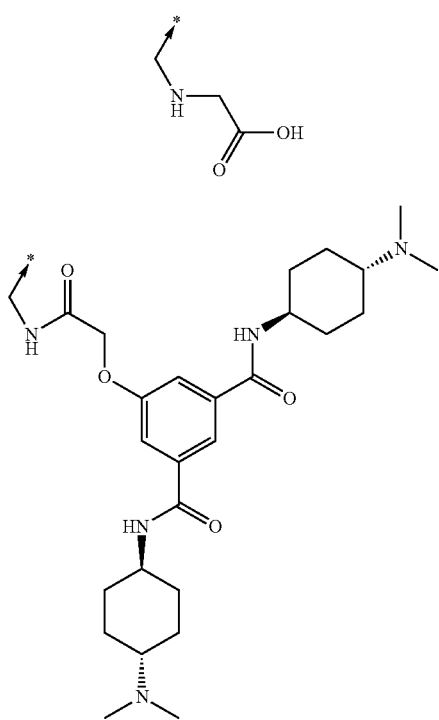

8. The compound of formula (I) according to claim 1, characterized in that
R$^4$ denotes H, F or Cl.

9. The compound of formula (I) according to claim 1, characterized in that
X denotes Cl or Br,
R$^1$ denotes methyl-, ethyl- or a substituent of formula (aa)

(aa)

R$^2$ denotes ethyl-, 2-propyl- or a substituent of formula (ba)

(ba)

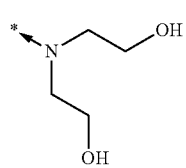

R$^3$ denotes a substituent selected from the group consisting of formula (ca)-(cad)

(ca)

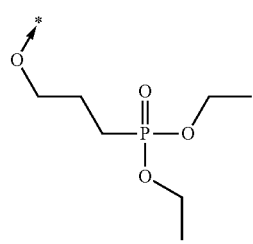

(cb)

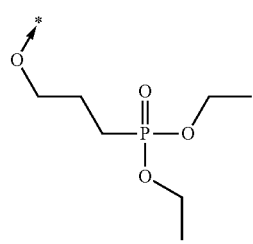

(cc)

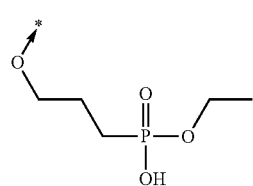

(cd)

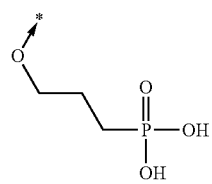

(ce)

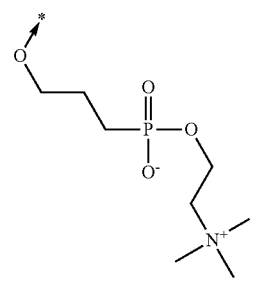

(cf)

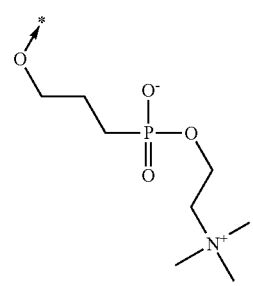

(cg)

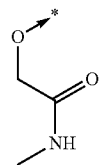

(ch)

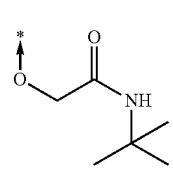

121
-continued
(ci)
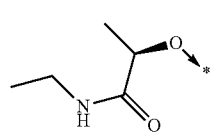
(cj)
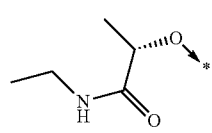
(ck)
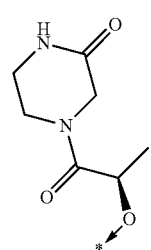
(cl)
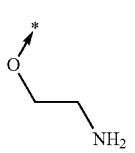
(cm)
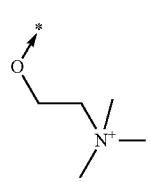
(cn)
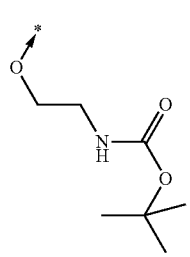
(co)
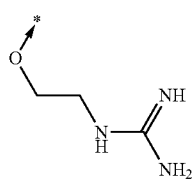
(cp)
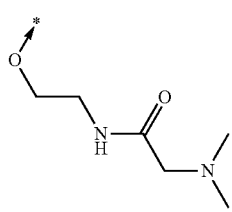
122
-continued
(cq)
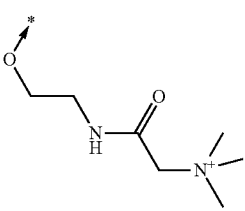
(cr)
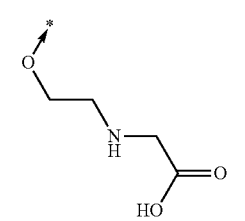
(cs)
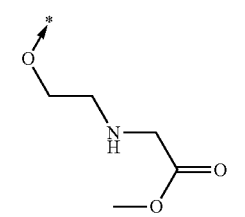
(ct)
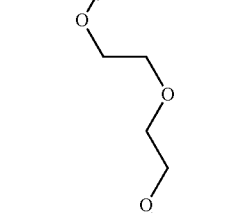
(cu)
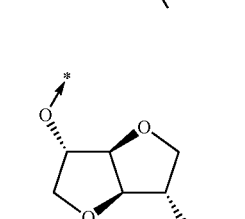
(cv)
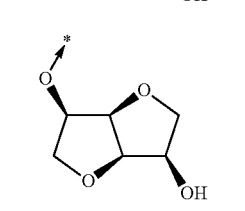
(cx)
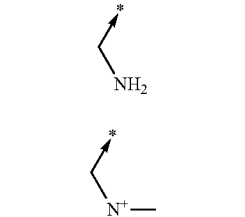
(cy)
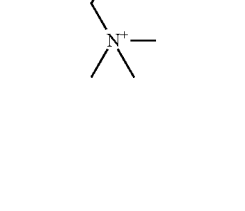

(cz)
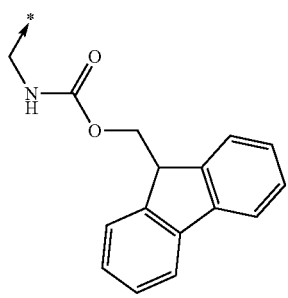

(caa)
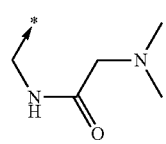

(cab)
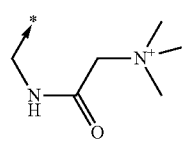

(cac)
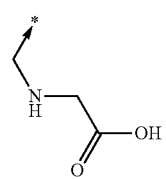

(cad)
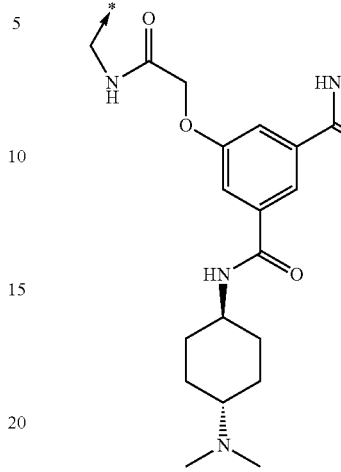

$R^4$ denotes H, F or Cl, $Z^-$ denotes a physiologically acceptable anion selected from the group consisting of chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate, z denotes 0 for negatively charged substituents $R^1$-$R^4$, 1 for uncharged substituents $R^1$-$R^4$ or 2 for positively charged substituents $R^1$-$R^4$, or a tautomer or pharmacologically acceptable acid addition salt thereof.

10. A pharmaceutical composition comprising at least one compound according to claim 1 or a pharmaceutically acceptable acid addition salt thereof and a pharmaceutically acceptable carrier.

11. The compound of formula (I) according to claim 1, selected from the group consisting of

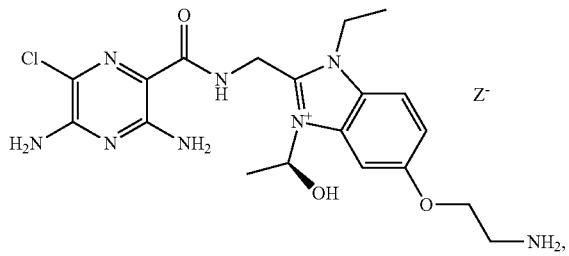

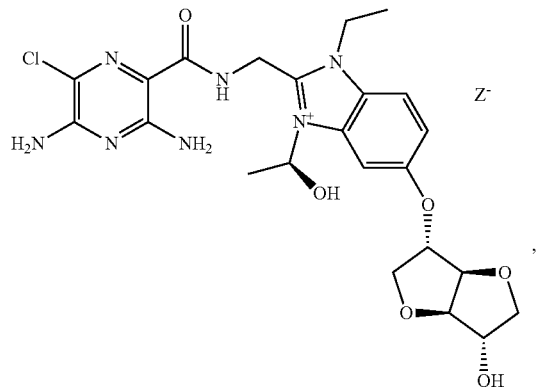

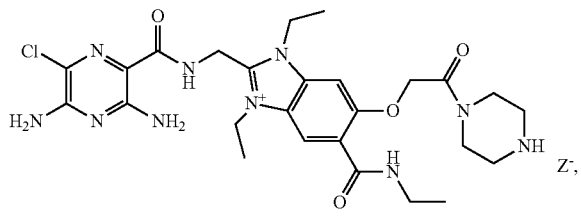

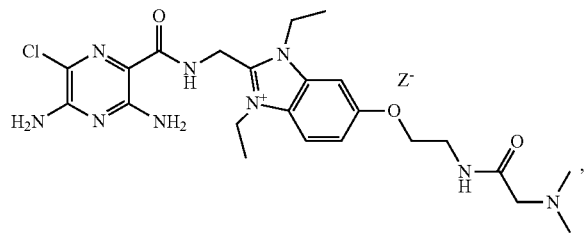

125
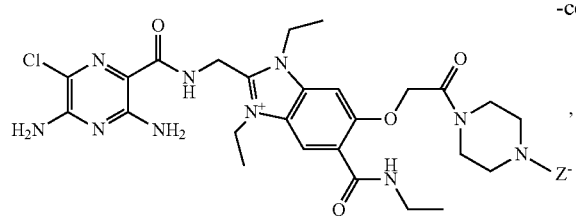
126
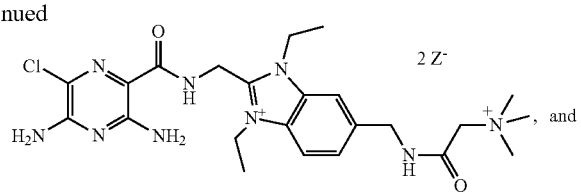
-continued
, and
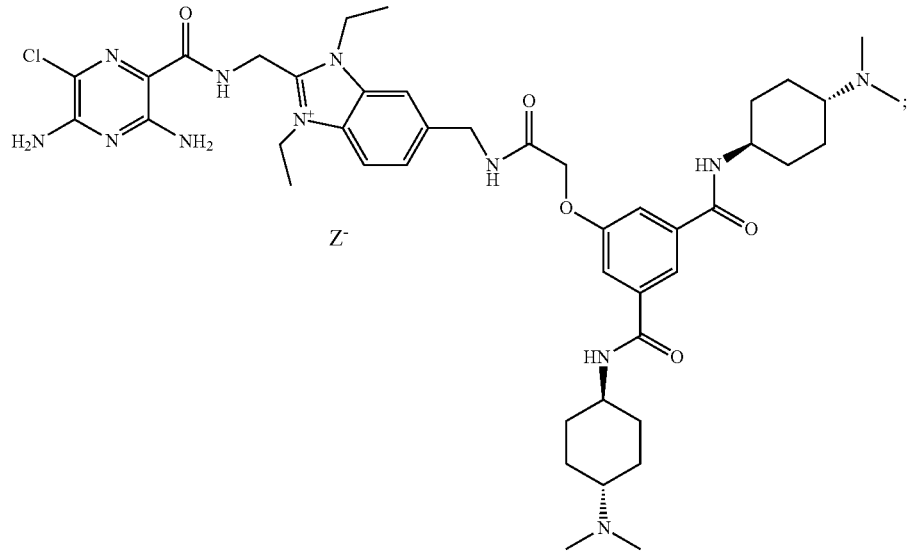
wherein Z⁻ is defined as in claim 1;
or a tautomer or pharmacologically acceptable acid addition salt thereof.
* * * * *